(12) United States Patent
Hossler et al.

(10) Patent No.: US 9,499,614 B2
(45) Date of Patent: Nov. 22, 2016

(54) METHODS FOR MODULATING PROTEIN GLYCOSYLATION PROFILES OF RECOMBINANT PROTEIN THERAPEUTICS USING MONOSACCHARIDES AND OLIGOSACCHARIDES

(71) Applicant: AbbVie, Inc., North Chicago, IL (US)

(72) Inventors: Patrick Hossler, Westborough, MA (US); Sean McDermott, Warwick, RI (US); Christopher Racicot, Auburn, MA (US); Ivan Correia, Winchester, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/209,821

(22) Filed: Mar. 13, 2014

(65) Prior Publication Data

US 2014/0271632 A1    Sep. 18, 2014

Related U.S. Application Data

(60) Provisional application No. 61/785,901, filed on Mar. 14, 2013.

(51) Int. Cl.
C07K 16/24 (2006.01)
C12P 21/08 (2006.01)
C12P 21/00 (2006.01)

(52) U.S. Cl.
CPC ............ *C07K 16/241* (2013.01); *C12P 21/005* (2013.01); *C07K 2317/41* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,925,796 A | 5/1990 | Bergh et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,047,335 A | 9/1991 | Paulson et al. |
| 5,096,816 A | 3/1992 | Maiorella |
| 5,110,913 A | 5/1992 | Coan et al. |
| 5,112,469 A | 5/1992 | Kempf et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,169,936 A | 12/1992 | Staples et al. |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,605,923 A | 2/1997 | Christensen, IV et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,730,975 A | 3/1998 | Hotamisligil et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |

(Continued)

FOREIGN PATENT DOCUMENTS

| | | |
|---|---|---|
| CN | 1299370 A | 6/2001 |
| CN | 1563090 A | 1/2005 |

(Continued)

OTHER PUBLICATIONS

"Genentech unveils production capacity hikes," in-Pharma Technologist.com Jun. 28, 2005, pp. 1-2.
"Memorandum in Support of Centocor's Motion for Summary Judgment No. 1 that all Asserted Claims Are Invalid for Lack of Written Description", dated Aug. 1, 2013 and submitted by defendant in Civil Action No. 09-40089-FDS.
"Memorandum in Support of Centocor's Motion for Summary Judgment No. 2 that All Asserted Claims are Invalid for Lack of Enablement", dated Aug. 1, 2013 and submitted by defendant in Civil Action No. 09-40089-FDS.
"Memorandum in Support of Centocor's Motion for Summary Judgment No. 4 that Claims Encompassing Non-recombinant Human Antibodies are Invalid for Failing to Meet the Requirements of 35 U.S.C. §112", dated Aug. 1, 2013 and submitted by defendant in Civil Action No. 09-40089-FDS.

(Continued)

*Primary Examiner* — David Romeo
(74) *Attorney, Agent, or Firm* — McCarter & English, LLP; Maria Laccotripe Zacharakis

(57) ABSTRACT

The present invention relates to the field of protein production, and in particular to methods and compositions for modulating glycosylation of proteins expressed in host cells.

22 Claims, 21 Drawing Sheets

(56) References Cited

U.S. PATENT DOCUMENTS

| | | |
|---|---|---|
| 5,929,212 A | 7/1999 | Jolliffe et al. |
| 5,945,098 A | 8/1999 | Sarno et al. |
| 5,945,311 A | 8/1999 | Lindhofer et al. |
| 5,976,833 A | 11/1999 | Furukawa et al. |
| 5,989,830 A | 11/1999 | Davis et al. |
| 5,994,510 A | 11/1999 | Adair et al. |
| 6,005,082 A | 12/1999 | Smeds |
| 6,015,558 A | 1/2000 | Hotamisligil et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,093,324 A | 7/2000 | Bertolini et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,171,825 B1 | 1/2001 | Chan et al. |
| 6,235,281 B1 | 5/2001 | Stenzel et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,506,598 B1 | 1/2003 | Andersen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,656,466 B1 | 12/2003 | Etcheverry et al. |
| 6,673,575 B1 * | 1/2004 | Franze .................. C07K 14/505 435/325 |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,936,441 B2 | 8/2005 | Reiter et al. |
| 6,974,681 B1 | 12/2005 | McGrew |
| 7,029,872 B2 | 4/2006 | Gerngross |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,229,432 B2 | 6/2007 | Marshall et al. |
| 7,250,165 B2 | 7/2007 | Heavner et al. |
| 7,276,239 B2 | 10/2007 | Le et al. |
| 7,297,680 B2 | 11/2007 | Opstelten et al. |
| 7,323,553 B2 | 1/2008 | Fahrner et al. |
| 7,326,681 B2 | 2/2008 | Gerngross |
| 7,332,303 B2 | 2/2008 | Schilling et al. |
| 7,390,660 B2 | 6/2008 | Behrendt et al. |
| 7,427,659 B2 | 9/2008 | Shukla et al. |
| 7,429,491 B2 | 9/2008 | Luan et al. |
| 7,449,308 B2 | 11/2008 | Gerngross et al. |
| 7,473,680 B2 | 1/2009 | DeFrees et al. |
| 7,504,485 B2 | 3/2009 | Salfeld et al. |
| 7,517,670 B2 | 4/2009 | Umana et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,612,181 B2 | 11/2009 | Wu et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,906,329 B2 | 3/2011 | Umana et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,034,906 B2 | 10/2011 | Borhani et al. |
| 8,043,863 B2 | 10/2011 | Bosques et al. |
| 8,053,236 B2 | 11/2011 | Morris et al. |
| 8,067,182 B2 | 11/2011 | Kelley et al. |
| 8,093,045 B2 * | 1/2012 | Pla .................. C07K 16/00 435/325 |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,216,851 B2 | 7/2012 | Parsons et al. |
| 8,231,876 B2 | 7/2012 | Wan et al. |
| 8,304,250 B2 | 11/2012 | Parsons et al. |
| 8,313,925 B2 | 11/2012 | Gregory et al. |
| 8,338,088 B2 | 12/2012 | Collins et al. |
| 8,361,705 B2 | 1/2013 | Parsons et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,388,965 B2 | 3/2013 | Rao et al. |
| 8,399,627 B2 | 3/2013 | Votsmeier et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,318 B2 | 6/2013 | Ravetch et al. |
| 8,470,552 B2 | 6/2013 | Croughan et al. |
| 8,512,983 B2 | 8/2013 | Gawlitzek et al. |
| 8,530,192 B2 | 9/2013 | Knudsen |
| 8,586,356 B2 | 11/2013 | Bosques et al. |
| 8,623,644 B2 | 1/2014 | Umana et al. |
| 8,629,248 B2 | 1/2014 | Umana et al. |
| 8,632,773 B2 | 1/2014 | Kasermann et al. |
| 8,652,487 B2 | 2/2014 | Maldonado |
| 8,663,945 B2 | 3/2014 | Pla et al. |
| 8,663,999 B2 | 3/2014 | Parsons et al. |
| 8,703,498 B2 | 4/2014 | Parsons et al. |
| 8,729,241 B2 | 5/2014 | Liu et al. |
| 8,753,633 B2 | 6/2014 | Salfeld et al. |
| 8,821,865 B2 | 9/2014 | Neu et al. |
| 8,852,889 B2 | 10/2014 | Prentice |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 * | 12/2014 | Pla .................. C07K 16/00 435/326 |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 8,969,024 B2 | 3/2015 | Kaymakcalan et al. |
| 9,017,687 B1 | 4/2015 | Wang et al. |
| 9,018,361 B2 | 4/2015 | Hickman et al. |
| 9,023,992 B2 | 5/2015 | Rasmussen et al. |
| 9,035,027 B2 | 5/2015 | Ghayur et al. |
| 9,062,106 B2 | 6/2015 | Bengea et al. |
| 9,067,990 B2 | 6/2015 | Wang et al. |
| 9,073,988 B2 | 7/2015 | Pla et al. |
| 9,085,618 B2 | 7/2015 | Ramasubramanyan et al. |
| 9,085,619 B2 | 7/2015 | Fraunhofer et al. |
| 9,090,688 B2 | 7/2015 | Bengea et al. |
| 9,090,867 B2 | 7/2015 | Pla et al. |
| 9,096,666 B2 | 8/2015 | Wan et al. |
| 9,096,879 B2 | 8/2015 | Khetan et al. |
| 9,102,723 B2 | 8/2015 | Wan et al. |
| 9,103,821 B2 | 8/2015 | Bosques et al. |

(56) References Cited

U.S. PATENT DOCUMENTS

| | | |
|---|---|---|
| 9,109,010 B2 | 8/2015 | Hickman et al. |
| 9,144,755 B2 | 9/2015 | Brown et al. |
| 9,150,645 B2 | 10/2015 | Subramanian et al. |
| 9,181,337 B2 | 11/2015 | Subramanian et al. |
| 9,181,572 B2 | 11/2015 | Subramanian et al. |
| 9,182,467 B2 | 11/2015 | Parsons et al. |
| 9,200,069 B2 | 12/2015 | Ramasubramanyan et al. |
| 9,200,070 B2 | 12/2015 | Ramasubramanyan et al. |
| 9,206,390 B2 | 12/2015 | Rives et al. |
| 9,234,032 B2 | 1/2016 | Pla et al. |
| 9,234,033 B2 | 1/2016 | Rives et al. |
| 9,249,182 B2 | 2/2016 | Herigstad et al. |
| 9,255,143 B2 | 2/2016 | Bengea et al. |
| 9,265,815 B2 | 2/2016 | Fraser et al. |
| 9,266,949 B2 | 2/2016 | Ramasubramanyan et al. |
| 9,273,132 B2 | 3/2016 | Wan et al. |
| 9,284,371 B2 | 3/2016 | Pla et al. |
| 9,290,568 B2 | 3/2016 | Rives et al. |
| 9,315,574 B2 | 4/2016 | Ramasubramanyan et al. |
| 9,328,165 B2 | 5/2016 | Wan et al. |
| 9,334,319 B2 | 5/2016 | Ramasubramanyan et al. |
| 9,346,879 B2 | 5/2016 | Ramasubramanyan et al. |
| 9,359,434 B2 | 6/2016 | Subramanian et al. |
| 9,365,645 B1 | 6/2016 | Bengea et al. |
| 2001/0021525 A1 | 9/2001 | Hirai et al. |
| 2002/0045207 A1 | 4/2002 | Krummen et al. |
| 2002/0119530 A1 | 8/2002 | Maiorella et al. |
| 2002/0132299 A1 | 9/2002 | Field |
| 2002/0137673 A1 | 9/2002 | Pingel et al. |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0170813 A1 | 9/2003 | Suga et al. |
| 2003/0175884 A1 | 9/2003 | Umana et al. |
| 2003/0178368 A1 | 9/2003 | van Reis |
| 2003/0203448 A1 | 10/2003 | Reiter et al. |
| 2003/0206898 A1 | 11/2003 | Fischkoff et al. |
| 2003/0211573 A1 | 11/2003 | Ryll |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0043446 A1 | 3/2004 | DeFrees et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136986 A1 | 7/2004 | Raju |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0191256 A1 | 9/2004 | Raju |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0084969 A1 | 4/2005 | Schorgendorfer et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0057638 A1 | 3/2006 | Bosques et al. |
| 2006/0083741 A1 | 4/2006 | Hoffman et al. |
| 2006/0127950 A1 | 6/2006 | Bosques et al. |
| 2006/0149042 A1 | 7/2006 | Konstantinov et al. |
| 2006/0153846 A1 | 7/2006 | Krause et al. |
| 2006/0223147 A1 | 10/2006 | Nishiya et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0275867 A1 | 12/2006 | Chotteau et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0015239 A1 | 1/2007 | Bihoreau et al. |
| 2007/0020260 A1 | 1/2007 | Presta |
| 2007/0041905 A1 | 2/2007 | Hoffman et al. |
| 2007/0054390 A1 | 3/2007 | Kelley et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0134256 A1 | 6/2007 | Lai et al. |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0212770 A1 | 9/2007 | Grillberger et al. |
| 2007/0248600 A1 | 10/2007 | Hansen et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0009040 A1 | 1/2008 | Grillberger et al. |
| 2008/0025976 A1 | 1/2008 | Le et al. |
| 2008/0058507 A1 | 3/2008 | Liu et al. |
| 2008/0095762 A1 | 4/2008 | Presta |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0206246 A1 | 8/2008 | Ravetch et al. |
| 2008/0219952 A1 | 9/2008 | Fischer et al. |
| 2008/0226635 A1 | 9/2008 | Koll et al. |
| 2008/0227136 A1* | 9/2008 | Pla .......... C07K 16/00 435/29 |
| 2008/0254514 A1 | 10/2008 | Knudsen |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0069232 A1 | 3/2009 | Callewaert et al. |
| 2009/0110679 A1 | 4/2009 | Li et al. |
| 2009/0123378 A1 | 5/2009 | Wong et al. |
| 2009/0136525 A1 | 5/2009 | Gerngross et al. |
| 2009/0142828 A1 | 6/2009 | Bucciarelli et al. |
| 2009/0148513 A1 | 6/2009 | Fraunhofer et al. |
| 2009/0151023 A1* | 6/2009 | Kuvshinov ........ C12N 15/8205 |

(56) References Cited

U.S. PATENT DOCUMENTS

| | | | |
|---|---|---|---|
| 2009/0155205 A1 | 6/2009 | Salfeld et al. | 800/294 |
| 2009/0175857 A1 | 7/2009 | Salfeld et al. | |
| 2009/0202546 A1 | 8/2009 | Harris et al. | |
| 2009/0202557 A1 | 8/2009 | Argiriadi et al. | |
| 2009/0203055 A1 | 8/2009 | Ngantung et al. | |
| 2009/0208500 A1 | 8/2009 | Joly et al. | |
| 2009/0226530 A1 | 9/2009 | Lassner et al. | |
| 2009/0239259 A1 | 9/2009 | Hsieh | |
| 2009/0253174 A1* | 10/2009 | Serber | C12P 21/06 435/69.1 |
| 2009/0258018 A1 | 10/2009 | Medich et al. | |
| 2009/0269302 A1 | 10/2009 | Salfeld et al. | |
| 2009/0271164 A1 | 10/2009 | Peng et al. | |
| 2009/0280065 A1 | 11/2009 | Willian et al. | |
| 2009/0291062 A1 | 11/2009 | Fraunhofer et al. | |
| 2009/0304682 A1 | 12/2009 | Hoffman et al. | |
| 2009/0317399 A1 | 12/2009 | Pollack et al. | |
| 2010/0003243 A1 | 1/2010 | Okun et al. | |
| 2010/0004907 A1 | 1/2010 | Kidal et al. | |
| 2010/0016557 A1 | 1/2010 | Salfeld et al. | |
| 2010/0021451 A1 | 1/2010 | Wong | |
| 2010/0034823 A1 | 2/2010 | Borhani et al. | |
| 2010/0040604 A1 | 2/2010 | Salfeld et al. | |
| 2010/0040630 A1 | 2/2010 | Elden et al. | |
| 2010/0069617 A1 | 3/2010 | Gagnon | |
| 2010/0113294 A1 | 5/2010 | Venkataraman et al. | |
| 2010/0120094 A1 | 5/2010 | Johnsen et al. | |
| 2010/0135987 A1 | 6/2010 | Hickman et al. | |
| 2010/0136025 A1 | 6/2010 | Hickman et al. | |
| 2010/0145029 A1 | 6/2010 | Gagnon | |
| 2010/0151499 A1 | 6/2010 | Collins et al. | |
| 2010/0160894 A1 | 6/2010 | Julian et al. | |
| 2010/0167313 A1 | 7/2010 | Essig et al. | |
| 2010/0172911 A1 | 7/2010 | Naso et al. | |
| 2010/0189717 A1* | 7/2010 | Kim | C07K 14/70521 424/133.1 |
| 2010/0221823 A1 | 9/2010 | McCoy et al. | |
| 2010/0255013 A1 | 10/2010 | Presta | |
| 2010/0256336 A1 | 10/2010 | Yuk et al. | |
| 2010/0278808 A1 | 11/2010 | Ravetch et al. | |
| 2010/0278822 A1 | 11/2010 | Fraunhofer et al. | |
| 2010/0279306 A1 | 11/2010 | Bosques et al. | |
| 2010/0291624 A1 | 11/2010 | Zhang et al. | |
| 2010/0292443 A1 | 11/2010 | Sabbadini et al. | |
| 2010/0297609 A1 | 11/2010 | Wells et al. | |
| 2010/0297697 A1 | 11/2010 | Ambrosius et al. | |
| 2011/0002935 A1 | 1/2011 | Wan et al. | |
| 2011/0003338 A1 | 1/2011 | Bayer et al. | |
| 2011/0039300 A1 | 2/2011 | Bayer et al. | |
| 2011/0039729 A1 | 2/2011 | Delisa et al. | |
| 2011/0053223 A1 | 3/2011 | Bayer et al. | |
| 2011/0053265 A1 | 3/2011 | Follstad et al. | |
| 2011/0054414 A1 | 3/2011 | Shang et al. | |
| 2011/0081679 A1 | 4/2011 | Jing et al. | |
| 2011/0081700 A1 | 4/2011 | Hasslacher et al. | |
| 2011/0086050 A1 | 4/2011 | Presta | |
| 2011/0086798 A1 | 4/2011 | Sethuraman et al. | |
| 2011/0097336 A1 | 4/2011 | Wu et al. | |
| 2011/0117601 A1 | 5/2011 | Haberger et al. | |
| 2011/0123544 A1 | 5/2011 | Salfeld et al. | |
| 2011/0124024 A1 | 5/2011 | Raju et al. | |
| 2011/0129468 A1 | 6/2011 | Mccue et al. | |
| 2011/0130544 A1 | 6/2011 | Ram et al. | |
| 2011/0136682 A1 | 6/2011 | Bosques et al. | |
| 2011/0171227 A1 | 7/2011 | Okun et al. | |
| 2011/0207676 A1 | 8/2011 | Callewaert et al. | |
| 2011/0213137 A1 | 9/2011 | Bosques et al. | |
| 2011/0263828 A1 | 10/2011 | Wong et al. | |
| 2011/0300151 A1 | 12/2011 | Okun et al. | |
| 2011/0318340 A1* | 12/2011 | Collin | C07K 16/00 424/133.1 |
| 2012/0014956 A1 | 1/2012 | Kupper et al. | |
| 2012/0015438 A1 | 1/2012 | Schilling et al. | |
| 2012/0039900 A1 | 2/2012 | Stuhlmuller et al. | |
| 2012/0039908 A1 | 2/2012 | Combs et al. | |
| 2012/0077213 A1 | 3/2012 | Pla et al. | |
| 2012/0093810 A1 | 4/2012 | Takada et al. | |
| 2012/0107783 A1 | 5/2012 | Julian et al. | |
| 2012/0107874 A1 | 5/2012 | Liu et al. | |
| 2012/0122076 A1 | 5/2012 | Lau et al. | |
| 2012/0122759 A1 | 5/2012 | Brown et al. | |
| 2012/0123688 A1 | 5/2012 | Ramasubramanyan et al. | |
| 2012/0129185 A1 | 5/2012 | Maksymowych et al. | |
| 2012/0134988 A1 | 5/2012 | Ravetch et al. | |
| 2012/0171123 A1 | 7/2012 | Medich et al. | |
| 2012/0177596 A1 | 7/2012 | Fischkoff et al. | |
| 2012/0177640 A1 | 7/2012 | Burg et al. | |
| 2012/0178107 A1 | 7/2012 | Salfeld et al. | |
| 2012/0183997 A1 | 7/2012 | Alley et al. | |
| 2012/0190005 A1 | 7/2012 | Schaub et al. | |
| 2012/0195885 A1 | 8/2012 | Correia et al. | |
| 2012/0201831 A1 | 8/2012 | Salfeld et al. | |
| 2012/0202974 A1 | 8/2012 | Eon-Duval et al. | |
| 2012/0213792 A1 | 8/2012 | Salfeld et al. | |
| 2012/0219564 A1 | 8/2012 | Salfeld et al. | |
| 2012/0230913 A1 | 9/2012 | Johnston et al. | |
| 2012/0238730 A1 | 9/2012 | Dong et al. | |
| 2012/0244168 A1 | 9/2012 | Salfeld et al. | |
| 2012/0251541 A1 | 10/2012 | Baurin et al. | |
| 2012/0251550 A1 | 10/2012 | Borhani et al. | |
| 2012/0258114 A1 | 10/2012 | Salfeld et al. | |
| 2012/0258496 A1 | 10/2012 | Ellwanger et al. | |
| 2012/0263731 A1 | 10/2012 | Fraunhofer et al. | |
| 2012/0264920 A1 | 10/2012 | Wang et al. | |
| 2012/0264927 A1 | 10/2012 | Parsons et al. | |
| 2012/0271041 A1 | 10/2012 | Ficko Trcek | |
| 2012/0276109 A1 | 11/2012 | Fraser et al. | |
| 2012/0276134 A1 | 11/2012 | Fraser et al. | |
| 2012/0276155 A1 | 11/2012 | Kishimoto et al. | |
| 2012/0276157 A1 | 11/2012 | Fraser et al. | |
| 2012/0276158 A1 | 11/2012 | Fraser et al. | |
| 2012/0276160 A1 | 11/2012 | Maldonado | |
| 2012/0276631 A1 | 11/2012 | Bengea et al. | |
| 2012/0277165 A1 | 11/2012 | Collins et al. | |
| 2012/0282262 A1 | 11/2012 | Okun et al. | |
| 2012/0282270 A1 | 11/2012 | Krause et al. | |
| 2012/0288494 A1 | 11/2012 | Borhani et al. | |
| 2012/0294888 A1 | 11/2012 | Kishimoto et al. | |
| 2012/0301498 A1 | 11/2012 | Altreuter et al. | |
| 2012/0301510 A1 | 11/2012 | Kishimoto et al. | |
| 2012/0308514 A1 | 12/2012 | Salfeld et al. | |
| 2012/0309056 A1 | 12/2012 | Leon et al. | |
| 2012/0329709 A1 | 12/2012 | Collins et al. | |
| 2013/0004507 A1 | 1/2013 | Fischkoff et al. | |
| 2013/0028903 A1 | 1/2013 | Wan et al. | |
| 2013/0065219 A1 | 3/2013 | Tsang et al. | |
| 2013/0084605 A1 | 4/2013 | Zhou et al. | |
| 2013/0096283 A1 | 4/2013 | Khetan et al. | |
| 2013/0115224 A1 | 5/2013 | Salfeld et al. | |
| 2013/0122011 A1 | 5/2013 | Hoffman et al. | |
| 2013/0122018 A1 | 5/2013 | Salfeld et al. | |
| 2013/0149300 A1 | 6/2013 | Hiatt et al. | |
| 2013/0156760 A1 | 6/2013 | Fraunhofer et al. | |
| 2013/0189737 A1 | 7/2013 | Kang et al. | |
| 2013/0195888 A1 | 8/2013 | Wang et al. | |
| 2013/0205604 A1 | 8/2013 | Esenwein et al. | |
| 2013/0231255 A1 | 9/2013 | Collins et al. | |
| 2013/0243786 A1 | 9/2013 | Banerjee et al. | |
| 2013/0244280 A1 | 9/2013 | Parikh et al. | |
| 2013/0245139 A1 | 9/2013 | Kozlov et al. | |
| 2013/0273059 A1 | 10/2013 | Wan et al. | |
| 2013/0280267 A1 | 10/2013 | Wan et al. | |
| 2013/0280274 A1 | 10/2013 | Subramanian et al. | |
| 2013/0309242 A1 | 11/2013 | Wan et al. | |
| 2013/0323261 A1 | 12/2013 | Wan et al. | |
| 2013/0330356 A1 | 12/2013 | Salfeld et al. | |
| 2013/0330357 A1 | 12/2013 | Salfeld et al. | |
| 2013/0336957 A1 | 12/2013 | Wang et al. | |
| 2013/0338344 A1 | 12/2013 | Ramasubramanyan et al. | |
| 2013/0344084 A1 | 12/2013 | Subramanian et al. | |
| 2014/0010820 A1 | 1/2014 | Wang et al. | |
| 2014/0045212 A1 | 2/2014 | Bosques et al. | |
| 2014/0046032 A1 | 2/2014 | Blanche et al. | |

(56) References Cited

U.S. PATENT DOCUMENTS

| | | |
|---|---|---|
| 2014/0065710 A1 | 3/2014 | Rives et al. |
| 2014/0072585 A1 | 3/2014 | Herigstad et al. |
| 2014/0087423 A1 | 3/2014 | Koncilja et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0199340 A1 | 7/2014 | Maldonado |
| 2014/0199729 A1 | 7/2014 | Srivastava et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271622 A1 | 9/2014 | Prentice |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0273057 A1 | 9/2014 | Prentice et al. |
| 2014/0274911 A1 | 9/2014 | Collins et al. |
| 2014/0274912 A1 | 9/2014 | Prentice |
| 2014/0275494 A1 | 9/2014 | Wang et al. |
| 2014/0288272 A1 | 9/2014 | Allison et al. |
| 2014/0288278 A1 | 9/2014 | Nti-gyabaah et al. |
| 2014/0296490 A1 | 10/2014 | Faid et al. |
| 2014/0301977 A1 | 10/2014 | Nadarajah et al. |
| 2014/0314745 A1 | 10/2014 | Rives et al. |
| 2014/0363845 A1* | 12/2014 | Sinacore ............... C12N 5/0018 435/69.6 |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0125905 A1 | 5/2015 | Pla et al. |
| 2015/0132320 A1 | 5/2015 | Chumsae et al. |
| 2015/0132801 A1 | 5/2015 | Ramasubramanyan et al. |
| 2015/0133639 A1 | 5/2015 | Wentz et al. |
| 2015/0139988 A1 | 5/2015 | Labkovsky et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1 | 7/2015 | Rives et al. |
| 2015/0183866 A1 | 7/2015 | Rives et al. |
| 2015/0197579 A1 | 7/2015 | Stefan et al. |
| 2015/0210735 A1 | 7/2015 | Hickman et al. |
| 2015/0259410 A1 | 9/2015 | Ramasubramanyan et al. |
| 2015/0299249 A1 | 10/2015 | Herigstad et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328333 A1 | 11/2015 | Fraser et al. |
| 2015/0329588 A1 | 11/2015 | Wang et al. |
| 2015/0335762 A1 | 11/2015 | Fraser et al. |
| 2015/0344564 A1 | 12/2015 | Hickman et al. |
| 2015/0361169 A1 | 12/2015 | Wan et al. |
| 2015/0361170 A1 | 12/2015 | Fraunhofer et al. |
| 2016/0017030 A1 | 1/2016 | Neu et al. |
| 2016/0017281 A1 | 1/2016 | Sunstrom |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0039924 A1 | 2/2016 | Zeng |
| 2016/0039925 A1 | 2/2016 | Subramanian et al. |
| 2016/0046708 A1 | 2/2016 | Subramanian et al. |
| 2016/0068881 A1 | 3/2016 | Prentice |
| 2016/0083452 A1 | 3/2016 | Hickman et al. |
| 2016/0115193 A1 | 4/2016 | Herigstad et al. |
| 2016/0115195 A1 | 4/2016 | Mendiratta et al. |
| 2016/0122384 A1 | 5/2016 | Kim et al. |
| 2016/0138064 A1 | 5/2016 | Rives et al. |
| 2016/0145331 A1 | 5/2016 | Subramanian et al. |
| 2016/0159897 A1 | 6/2016 | Zeng |
| 2016/0185848 A1 | 6/2016 | Hossler et al. |
| 2016/0186130 A1 | 6/2016 | Pla et al. |
| 2016/0194390 A1 | 7/2016 | Ramasubramanyan et al. |
| 2016/0207922 A1 | 7/2016 | Tang et al. |
| 2016/0207992 A1 | 7/2016 | Bengea et al. |
| 2016/0215319 A1 | 7/2016 | Mendiratta et al. |
| 2016/0222101 A1 | 8/2016 | Fraunhofer et al. |
| 2016/0228371 A1 | 8/2016 | Schultz et al. |
| 2016/0237149 A1 | 8/2016 | Flikweert et al. |
| 2016/0237150 A1 | 8/2016 | Subramanian et al. |

FOREIGN PATENT DOCUMENTS

| | | |
|---|---|---|
| CN | 105777895 A | 7/2016 |
| CN | 105777896 A | 7/2016 |
| CN | 105777904 A | 7/2016 |
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 230584 A1 | 8/1987 |
| EP | 0351789 A2 | 1/1990 |
| EP | 0366043 A1 | 5/1990 |
| EP | 374510 A1 | 6/1990 |
| EP | 453898 A2 | 10/1991 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 585705 A1 | 3/1994 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1176195 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1849862 A2 | 10/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2305712 A1 | 4/2011 |
| EP | 2357250 A2 | 8/2011 |
| EP | 2495307 A1 | 9/2012 |
| EP | 2500414 A1 | 9/2012 |
| EP | 2528002 A2 | 11/2012 |
| EP | 2574677 A1 | 4/2013 |
| EP | 3036254 A1 | 6/2016 |
| EP | 3036320 A1 | 6/2016 |
| GB | 2160530 A | 12/1985 |
| GB | 2279077 A | 12/1994 |
| IN | 2285/MUM/2013 A1 | 1/2015 |
| JP | 6-292592 | * 10/1994 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/04054 A1 | 4/1991 |
| WO | WO-91/09967 A1 | 7/1991 |
| WO | WO-92/01047 A1 | 1/1992 |
| WO | WO-92/11383 A1 | 7/1992 |
| WO | WO-92/16221 A1 | 10/1992 |

(56) References Cited

FOREIGN PATENT DOCUMENTS

| | | |
|---|---|---|
| WO | WO-92/16553 A1 | 10/1992 |
| WO | WO-92/17583 A1 | 10/1992 |
| WO | WO-93/06213 A1 | 4/1993 |
| WO | WO-93/11793 A1 | 6/1993 |
| WO | WO-94/02602 A1 | 2/1994 |
| WO | WO-94/08619 A1 | 4/1994 |
| WO | WO-94/20139 A1 | 9/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-9704801 A1 | 2/1997 |
| WO | WO-97/13852 A1 | 4/1997 |
| WO | WO-97/29131 A1 | 8/1997 |
| WO | WO-98-08934 A1 | 3/1998 |
| WO | WO-98/24883 A2 | 6/1998 |
| WO | WO-98/24884 A1 | 6/1998 |
| WO | WO-98/24893 A2 | 6/1998 |
| WO | WO-9823645 A1 | 6/1998 |
| WO | WO-98/50433 A2 | 11/1998 |
| WO | WO-98/58964 A1 | 12/1998 |
| WO | WO-9856418 A1 | 12/1998 |
| WO | WO-99/22764 A1 | 5/1999 |
| WO | WO-99/32605 A1 | 7/1999 |
| WO | WO-99/54342 A1 | 10/1999 |
| WO | WO-99/57134 A1 | 11/1999 |
| WO | WO-99/57246 A1 | 11/1999 |
| WO | WO-003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-02/076578 A1 | 10/2002 |
| WO | WO-02/094192 A2 | 11/2002 |
| WO | WO-02/101019 A2 | 12/2002 |
| WO | WO-03/046162 | 6/2003 |
| WO | WO-03045995 A2 | 6/2003 |
| WO | WO-03/059935 A2 | 7/2003 |
| WO | WO-03/066662 A2 | 8/2003 |
| WO | WO-03/102132 A2 | 12/2003 |
| WO | WO 2004/008100 A2 * | 1/2004 |
| WO | WO-2004008100 A2 | 1/2004 |
| WO | WO-2004009776 A2 | 1/2004 |
| WO | WO-2004/026891 A2 | 4/2004 |
| WO | WO-2004/058944 A2 | 7/2004 |
| WO | WO-2004058800 A2 | 7/2004 |
| WO | WO-2004/076485 A1 | 9/2004 |
| WO | WO-2004/097006 A1 | 11/2004 |
| WO | WO-2005042569 A1 | 5/2005 |
| WO | WO-2005-062967 A2 | 7/2005 |
| WO | WO-2005/063813 A2 | 7/2005 |
| WO | WO-2005/082483 A1 | 9/2005 |
| WO | WO-2005100584 A2 | 10/2005 |
| WO | WO-2006/014683 A2 | 2/2006 |
| WO | WO-2006/026445 A1 | 3/2006 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007-005786 A2 | 1/2007 |
| WO | WO-2007/024743 A2 | 3/2007 |
| WO | WO-2007/055916 A2 | 5/2007 |
| WO | WO-2007/070315 A2 | 6/2007 |
| WO | WO-2007/077217 A2 | 7/2007 |
| WO | WO-2007/087384 A2 | 8/2007 |
| WO | WO-2007/117490 A2 | 10/2007 |
| WO | WO-2007/117505 A2 | 10/2007 |
| WO | WO-2008/008360 A1 | 1/2008 |
| WO | WO-2008/028686 A2 | 3/2008 |
| WO | WO-2008/033517 A2 | 3/2008 |
| WO | WO-2008-057240 A2 | 5/2008 |
| WO | WO-2008/057634 A2 | 5/2008 |
| WO | WO-2008068879 A1 | 6/2008 |
| WO | WO-2008/077545 A1 | 7/2008 |
| WO | WO-2008087184 A2 | 7/2008 |
| WO | WO-2008/128230 A1 | 10/2008 |
| WO | WO-2008121616 A2 | 10/2008 |
| WO | WO-2008135498 A2 | 11/2008 |
| WO | WO-2009/027041 A1 | 1/2009 |
| WO | WO-2009/017491 A1 | 2/2009 |
| WO | WO-2009023562 A2 | 2/2009 |
| WO | WO-2009058769 A1 | 5/2009 |
| WO | WO-2009/073569 A2 | 6/2009 |
| WO | WO-2009/079382 A1 | 6/2009 |
| WO | WO-2009135656 A1 | 11/2009 |
| WO | WO-2010-048183 A1 | 4/2010 |
| WO | WO-2010036443 A1 | 4/2010 |
| WO | WO-2010043703 A1 | 4/2010 |
| WO | WO-2010/080062 A1 | 7/2010 |
| WO | WO-2010/102114 A1 | 9/2010 |
| WO | WO-2010/111633 A2 | 9/2010 |
| WO | WO-2010122460 A1 | 10/2010 |
| WO | WO-2010/129469 A1 | 11/2010 |
| WO | WO-2010127069 A1 | 11/2010 |
| WO | WO-2010/136209 A1 | 12/2010 |
| WO | WO-2010/138502 A2 | 12/2010 |
| WO | WO-2010/141039 A1 | 12/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011133902 A2 | 10/2011 |
| WO | WO 2011134919 A2 | 11/2011 |
| WO | WO-2012/014183 A1 | 2/2012 |
| WO | WO-2012019160 A1 | 2/2012 |
| WO | WO-2012030512 A1 | 3/2012 |
| WO | WO-2012/046255 A2 | 4/2012 |
| WO | WO-2012050175 A1 | 4/2012 |
| WO | WO-2012051147 A1 | 4/2012 |
| WO | WO-2012/065072 A2 | 5/2012 |
| WO | WO-2012/068134 A1 | 5/2012 |
| WO | WO-2012062810 A2 | 5/2012 |
| WO | WO-2012/078376 A1 | 6/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO 2013/006461 A1 * | 1/2013 |
| WO | WO-2013-011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013/021279 A2 | 2/2013 |
| WO | WO-2013-066707 A2 | 5/2013 |
| WO | WO-2013/067301 A1 | 5/2013 |
| WO | WO-2013/095966 A1 | 6/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-164837 A1 | 11/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |
| WO | WO-2013-186230 A1 | 12/2013 |
| WO | WO-2014/018747 A2 | 1/2014 |

(56) References Cited

FOREIGN PATENT DOCUMENTS

| | | |
|---|---|---|
| WO | WO-2014/039903 A2 | 3/2014 |
| WO | WO-2014/052360 A2 | 4/2014 |
| WO | WO-2014/096672 A1 | 6/2014 |
| WO | WO-2014/099636 A1 | 6/2014 |
| WO | WO-2014/125374 A2 | 8/2014 |
| WO | WO-2014-149935 A1 | 9/2014 |
| WO | WO-2014/150655 A1 | 9/2014 |
| WO | WO-2014/151878 A2 | 9/2014 |
| WO | WO-2014/158231 A1 | 10/2014 |
| WO | WO-2014/159488 A1 | 10/2014 |
| WO | WO-2014/159494 A1 | 10/2014 |
| WO | WO-2014/159499 A1 | 10/2014 |
| WO | WO-2014/179601 A2 | 11/2014 |
| WO | WO-2014-196780 A1 | 12/2014 |
| WO | WO-2014/207763 A1 | 12/2014 |
| WO | WO-2015/004679 A1 | 1/2015 |
| WO | WO-2015/007912 A1 | 1/2015 |
| WO | WO-2015/051293 A2 | 4/2015 |
| WO | WO-2015/073884 A2 | 5/2015 |
| WO | WO-2016/007764 A1 | 1/2016 |
| WO | WO-2016/102383 A1 | 6/2016 |

OTHER PUBLICATIONS

"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS.

"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS.

"Plaintiffs' Memorandum in Support of Their Motion for Partial Summary Judgment", dated Aug. 1, 2013 and submitted by plaintiff in Civil Action No. 09-40089-FDS.

"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams. et al. J. Am. Acad. Dermatol 2004;51 :660-2.

Altamirano, C., et al., "Strategies for fed batch cultivation of t-PA producing CHO cells: substitution of glucose and glutamine and rational design of culture medium", *J. Biotechn*. 110:171-179, 2004.

Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

Avgerinos et al. (GAb '04 Abstracts—GE Healthcare Life Sciences, France Oct. 3-5, 2004, pp. 15-16 published 2005).

Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.

Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.

Barbuto, J. et al. "Production of Neutralizing Antibodies to Tumor Necrosis Factor by Human Tumor-Infiltrating B Lymphocytes" *Proc. Am. Assoc. Cancer Res*,. 34:487, Abstr. 2904 (1993).

Birch, JR. et al., "Antibody production", Adv. Drug Delivery Reviews 58:671-685, 2006.

Blaker, GJ, et al., "The Glucose, Insulin and Glutamine Requirements of Suspension Cultures of HeLa Cells in a Defined Culture Medium", J. Cell Sci. 9:529-537, 1971.

Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).

Bollati-Fogolin M., et al., "Temperature Reduction in Cultures of hGM-CSF-expressing CHO Cells: Effects on Productivity and Product Quantity", Biotechnol. Prog. 21:17-21, 2005.

Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.

Boswell et al. "Effects of Charge on Antibody Tissue Distribution and Pharmacokinetics" Bioconjugate Chem.(21) 2153-2163 (2010).

Boyle, P. et al. "A Novel Monoclonal Human IgM Autoantibody which Binds Recombinant Human and Mouse Tumor Necrosis Factor-α" *Cell. Immunol.*, 152:556-68 (1993).

Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).

Brekke, O. et al., "Therapeutic Antibodies for Human Diseases at the Dawn of the Twenty-first Century," *Nature*, vol. 2:52-62 (2002).

Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).

Bruggemann et al., "Production of human antibody repertoires in transgenic mice" Cur. Op. Biotechnol. *;455-458 (1997).

Bruggemann, M., Neuberger, M.S., "Strategies for expressing human antibody repertoires in transgenic mice," *Immunol. Today* 17:391-397 (1996).

Cai B, et al. "C-Terminal Lysine Processing of Human Immunoglobulin G2 Heavy Chain In Vivo" Biotechnol. Bioeng. 2011;108: 404-412.

Cambridge Antibody Technology, advertisement of phage display services, Science vol. 253, No. 5018 (1991).

Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.

Carter et al., "Humanization of an anti-p185HER2 antibody for human cancer therapy," *Proc. Nat. Acad. Sci* 89:4285-4289 (1992).

Chang KH, et al., "N-Acetylcysteine Increases the Biosynthesis of Recombinant EPO in Apoptotic Chinese Hamster Ovary Cells", Free Radic Res. 30(2):85-91, 1999.

Charter, Edward A., "A New Process for the Separation and Purification of Egg Yolk; Antibodies," BASc., The University of British Columbia; A Thesis; Apr. 1993.

Choo et al. "High-level production of a monoclonal antibody in murine myeloma cells by perfusion culture using a gravity settler" Biotechnology Progress, vol. 23, No. 1, Jan. 1, 2007, 225-231.

Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).

Chua, FKF et al., "Hyper-stimulation of monoclonal antibody production by high osmolarity stress in eRDF medium", J. Biotechnology 37(3):265-275, Nov. 15, 1994.

Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.

Chung et al., "Utilization of Lysozyme Charge Ladders to Examine the Effects of Protein Surface; Charqe Distribution on Bindinq Affinity in Ion Exchanqe Systems," Lanqmuir 26(2): 759-768 (2010).

Chung et al., "Cetuximab-Induced Anaphylaxis and IgE Specific for Galactose-α-1, 3-Galactose", *N. Engl. J. Med.*, 358:11, pp. 1109-1117 (2008).

Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).

(56) References Cited

OTHER PUBLICATIONS

Clincke, M. et al., "Effect of surfactant pluronic F-68 on CHO cell growth, metabolism, production, and glycosylation of human recombinant Inf-γ in mild operating conditions," Biotechnol. Prog. 27(1): 181-190, 2011.
Cohen, J., et al., "Intersept: An international, multicenter, placebo-controlled trial of monoclonal anitbody to human tumor necrosis factor-α in patients with sepsis," Crit Care Med, vol. 24(9):1431-1440 (1996).
Cox, J. et al. "A directory of human germ-line VK segments reveals a strong bias in their usage" Eur. J. Immunol., 24(2):827-36 (1994).
Cromwell (GAB'04 Abstracts—GE Healthcare Life Sciences, Franc Oct. 3-5, 2004, pp. 17-18 published 2005).
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." Biotechnology, 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
deZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
Dolezal, et al., "*Escherichia coli* Expression of a Bifunctional Fab-peptide Epitope Reagent for the Rapid Diagnosis of HIV-1 and HIV-2", Immunotechnology, 1:197-209 (1995).
Doring, E., "Identification and Characterization of a TNFa Antagonist Derived from a Monoclonal Antibody" (1994) Mol. Immunol .31(14): 1059-1067.
Elliot et al., "Repeated therapy with monoclonal antibody to tumour necrosis factor α (cA2) in patients with rheumatoid arthritis" (1994) Lancet, 344:1125-1127.
Elliot, "Treatment of rheumatoid arthritis with chimeric monoclonal antibodies to tumor necrosis factor α" (1993) Arthritis & Rheumatism, 36(12):1681-1690.
Emery, P. "Adalimumab therapy: Clinical findings and implications for integration into clinical guidelines for rheumatoid arthritis." Drugs of Today, 41(3): p. 155-153. (2005).
ERBITUX (cetuximab) label, Revised Aug. 2013.
Ewert et al., "Biophysical Properties of Human Antibody Variable Domains," J. Mol. Biol. 324:531-; 553 (2003).
Exhibit dated Aug. 1, 2013 and cited by defendant in Civil Action No. 09-40089-FDS providing the Jun. 23, 2009 trial transcript of the PM session in the matter of Centocor, et al. v. Abbott Laboratories.
Exhibit dated Aug. 1, 2013 and cited by defendant in Civil Action No. 09-40089-FDS providing the trial transcript in the matter of Abbott Laboratories, et al. v. The Mathilda and Terrance Kennedy Institute, S.D.N.Y.
Exhibit dated Aug. 1, 2013 and cited by plaintiff in Civil Action No. 09-40089-FDS providing excerpts from the File History of U.S. Appl. No. 12/578,487.
Exhibit dated Aug. 1, 2013 and cited by defendant in Civil Action No. 09-40089-FDS providing the Jun. 24, 2009 trial transcript of the AM session in the matter of Centocor, et al. v. Abbott Laboratories, E.D. TX.
Exhibit dated Aug. 1, 2013 and cited by defendant in Civil Action No. 09-40089-FDS providing the Sep. 20, 2012 Day 8 trial transcript in the matter of Abbott v. Centocor Ortho Biotech Inc., D. MA.
Exhibit dated Aug. 1, 2013 and cited by plaintiff in Civil Action No. 09-40089-FDS providing Declaration by Jochen Salfeld, dated Jan. 17, 2013.

FDA Package insert for Adalimumab, Sep. 26, 2003, pp. 1-18.
Feldmann, "Anti-TNF-alpha Therapy of Rheumatoid Arthritis: What Have We Learned?" (2001) Annu. Rev. Immunol., 19:163-196.
Figini, "In Vitro assembly of Repertoires of Antibody Chains on the Surface of Phage by Renaturation" (1994) J. Mol. Biol., 239:68-78.
Fishwild et al., "High-avidity human IgG kappa monoclonal antibodies from a novel strain of minilocus transgenic mice" (1996) Nature Biotechnology, 14:845-851.
Fomsgaard, "Auto-antibodies to Tumor Necrosis Factor α in Healthy Humans and Patients with Inflammatory Diseases and Gram-Negative Bacterial Infections" (1989) Scand. J. Immunol. 30:219-23.
Foote, J., "Antibody framework residues affecting the conformation of the hypervariable loops" (1992) J. Mol. Biol., 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," LC-GC 11 (1):26-34 (1993).
Gatto, B. "Biologics targeted at TNF: design, production and challenges", Reumatismo 58(2):94-103, 2006.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", Nature Biotechnology, 28(8):863-868 (2010).
Ghaderi, et al., "Production platforms for biotherapeutic glycoproteins. Occurrence, impact, and challenges of non-human sialylation", Biotechnology and Genetic Engineering Reviews, 28:147-176 (2012).
Gonzalez et al. "Purification of Lactic Acid from Fermentation Broths by Ion-Exchange Resins" Ind. Eng. Chem. Res. 45:3243 (2006).
Graf et al., "Ion exchange resins for the purification of monoclonal antibodies from animal cell culture" Bioseparation 4 (1) :7-20 (Feb. 1994).
Gram et al., "In vitro selection and affinity maturation of antibodies from a naive combinatorial immunoglobulin library" (1992) PNAS, 89:3576-3580.
Gramer et al., "Glycosidase Activities of the 293 and NS0 Cell Lines, and of an Antibody-Producing Hybridoma Cell Line", Biotechnology and Bioengineering, 43:423-428 (1994).
Green et al., "Antigen-specific human monoclonal antibodies from mice engineered with human Ig heavy and light chain YACs" (1994) Nature Genetics, 7:13-21.
Griffiths et al., "Isolation of high affinity human antibodies directly from large synthetic repertoires" (1994) EMBO J., 13:3245-3260.
Griffiths, "Human anti-self antibodies with high specificity from phage display libraries" (1993) The EMBO J. 12(2):725-34.
Grunberg, J. et al., "High-Yield Production of Recombinant Antibody Fragments in HEK-293 Cells Using Sodium Butyrate", BioTechniques 34(5):968-972, May 2003.
Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4):1 154-1164, 2005.
Harlow and Lane, Antibodies A Laboratory Manual, Purification of Antibodies by using a; Deae-matrix (Batch), Storing and Purifying Antibodies; Chapter 8: 302-303 (1988).
Harris et al. "Processing of C-terminal lysine and argnine residues of proteins isolated from mammalian cell culture" Journal of Chromatography, (1995) 705; 129-123.
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) J. Mol. Biol., 226:889-896.
Heidemann, R. et al., "The use of peptones as medium additives for the production of a recombinant therapeutic protein in high density perfusion cultures of mammalian cells", Cytotechnology 32:157-167, 2000.

(56) References Cited

OTHER PUBLICATIONS

Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(1 1):484-490 (2003).
Hoogenboom et al., "By-passing immunisation : Human antibodies from synthetic repertoires of germline VH gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler P. et al., "Improvement of mammalian cell culture performance through surfactant enabled concentrated feed media," Biotechnol. Prog. 29(4): 1023-1033, 2013.
http://www.cygnustechnologies.com/product_detail/host-cell-protein-antibodies/anti-cho-h . . . CYGNUS Technologies, Anti-CHO HCP (Apr. 18, 2012).
Huang et al. "Effects of anti-TNF monoclonal antibody infusion in patients with hairy cell leukaemia" (1992) *Br. J. Haematol.*, 81(2):231-234.
Hui et al., "Recovery and purification process development for monoclonal antibody production," MABS (2010) 2(5):480-499.
Humira (adalimumab) label, Revised Sep. 2013.
Huse, "Generation of a large combinatorial library of the immunoglobulin repertoire in phage lambda" (1989) *Science*, 246:1275-81.
International Preliminary Report on Patentability for Application No. PCT/US07/08359, dated Dec. 12, 2011.
International Preliminary Report on Patentability for Application No. PCT/US2011/060388, dated May 30, 2012.
International Search Report and Written Opinion for Application No. PCT/US2008/085066, dated May 12, 2009.
International Search Report and Written Opinion for Application No. PCT/US2010/033387, dated Aug. 7, 2012.
International Search Report and Written Opinion for Application No. PCT/US2013/031380, dated Feb. 5, 2014.
International Search Report and Written Opinion for Application No. PCT/US2013/041954, dated Dec. 17, 2013.
International Search Report and Written Opinion for Application No. PCT/US2013/041958, dated Dec. 17, 2013.
International Search Report and Written Opinion for Application No. PCT/US2013/065720, dated Dec. 16, 2013.
International Search Report and Written Opinion for Application No. PCT/US2013/065797, dated Nov. 26, 2013.
International Search Report for Application No. PCT/IB03/04502, dated May 26, 2004.
International Search Report for Application No. PCT/US2011/060388 dated May 30, 2012.
International Search Report for Application No. PCT/US2013/031352, Dated Apr. 25, 2013.
International Search Report for Application No. PCT/US2013/031389, Dated Jun. 3, 2013.
International Search Report for Application No. PCT/US2013/031485, Dated Jun. 25, 2013.
International Search Report for Application No. PCT/US2013/031681, Dated Jun. 14, 2013.
Invitation to Pay Additional Fees for International Application No. PCT/US2013/031380, Dated Nov. 28, 2013.
Jakobovits, A., "Production of fully human antibodies by transgenic mice" (1995) *Curr. Op. Biotechnol.*, 6:561-566.
Jespers, "Guiding the Selection of Human Antibodies from Phage Display Repertoires to a Single Epitope of an Antigen" (1994) *Bio/Technology*, 12:899-903.
Johnson et al. (Archives of Biochemistry and Biophysics 444 (2005) 7-14).
Kalyanpur, M., "Downstream Processing in the Biotechnology Industry" Molecular Biotechnology, vol. 22:87-98 (2002).
Karampetsou et al. (Q J Med 2010; 103:917-928).
Kaschak et al: "Characterization of the basic charge variants of a human IgGl: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGl: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatoqraphy, 266:3-21 (1983).
Lerner, "Antibodies without immunization" (1992) *Science*, 258:1313-1314.
Lewis, "Use of alanine scanning mutagenesis to improve the affinity of an anti gp120 (HIV) antibody" (1994) *J. Cell. Biochem.*, 18D:215.
Li, F. et al., "Current Therapeutic Antibody Production and Process Optimization" BioProcessing Journal, vol. 4(5):23-30 (2005).
Lifely et al., "Glycosylation and Biological Activity of CAMPATH-1H Expressed in Different Cell Lines and Grown Under Different Culture Conditions", *Glycobiology*, 5(8):813-822 (1995).
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.
Low, "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract (1996) *Cambridge University*.
Luo et al., "Understanding of C-terminal lysine variants in antibody production using mammalian cells" Abstract of papers, ACS, Anaheim, CA, US, Mar. 2011.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.

(56) References Cited

OTHER PUBLICATIONS

Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Ma, et al., "Generation and Assembly of Secretory Antibodies in Plants", Science, 268:716-719 (1995).
Maeda, et al., "Analysis of Nonhuman N-Glycans as the Minor Constituents in Recombinant Monoclonal Antibody Pharmaceuticals", Anal. Chem., 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".
Marks et al., "Human antibody fragments specific for human blood group antigens from a phage display library" (1993) Bio/Technology, 11:1145-1150.
Marks et al., "Molecular evolution of proteins on filamentous phage. Mimicking the strategy of the immune system" (1992) J. Biol. Chem. 267:16007-16010.
Marks, "By-passing immunization: Human antibodies from V-gene libraries displayed on phage" (1991) J. Mol. Biol., 222:581-597.
Marks, "Human Monoclonal Antibodies from V-gene Repertoires Expressed on Bacteriophage." In Antibody Engineering, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) Biotechnology, 10:779-783.
Martin, A.C.R. "Accessing the Kabat antibody sequence database by computer" (1996)PROTEINS: Structure, Function and Genetics, 25:130-133.
Martinelle, K. et al., Cells and Culture, Proceedings of the 20th ESACT Meeting v4 819-822, Jun. 17-20, 2007.
Medynski, "Phage Display: All Dressed Up and Ready to Role" (1994) Bio/Technology, 12:1134-1136.
Mendez et al., "Functional transplant of megabase human immunoglobulin loci recapitulates human antibody response in mice" (1997) Nature Genetics, 15:146-156.
Meuwly, F. et al., "Conversion of a CHO cell culture process from perfusion to fed-batch technology without altering product quality", J.Biotechn. 123:106-116, 2006.
Miller et al. "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Moore, A., et al., "Effects of temperature shift on cell cycle, apoptosis and nucleotide pools in CHO cell batch cultures", Cytotechnology, 23:47-54, 1997.
Möller, Monoclonal antibodies to human tumor necrosis factor α: in vitro and vivo application (1990) Cytokine, 2(3):162-69.
Neuberger M. et al., "Mice perform a human repertoire" (1997) Nature, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Nilsson, "Antibody engineering" (1995) Current Opinion in Structural Biology, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", Nephron, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", J. Biochem., 117:59-62 (1995).
Oh, D-K. et al., "Increased erythritol production in fed-batch cultures of Torula sp. By controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) Methods, 36(1):61-68.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Perchiacca et al., "Aggregation-resistance domain antibodies engineered with charged mutations; near the edges of the complementarity-determining regions," Protein Engineering Design & Selection, 25:10 (591-601) 2012.
Pietersz et al., "In vitro and in vivo Antitumor Activity of a Chimeric anti-CD19 Antibody", Cancer Immunol. Immunother., 41:53-60 (1995).
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, 1 Oct. 1996, pp. 189-200.
Potter et al., "Antibody Production in the Baculovirus Expression System", Intern. Rev. Immunol., 10:103-112 (1993).
Poul et al., "Design of Cassette Baculovirus Vectors for the Production of Therapeutic Antibodies in Insect Cells", Immunotechnology, 1:189-196 (1995).
Queen, C., "A humanized antibody that binds to the interleukin 2 receptor" (1989) Proc. Natl. Acad. Sci. USA, 86(24):10029-10033.
Rader et al. "A phage display approach to rapid antibody humanization: Designed combinatorial V gene libraries" (1998) Proc Natl Acad Sci USA, 95:8910-8915.
Raju, TS. "Glycosylation Variations with Expression Systems and Their Impact on Biological Activity of Therapeutic Immunoglobulins", BioProcess International., 44-53 (2003).
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) Crit. Care Med., 24(5):733-742.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast Pichia pastoris", Biotechnology, 13:255-260 (1995).
Riechmann, "Phage display and selection of a site-directed randomized single-chain antibody Fv fragment for its affinity improvement" (1993) Biochemistry, 32(34):8848-8855.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Rube et al. (Int. J. Radiation Oncology Biol. Phys., vol. 56, No. 5, pp. 1414-1425,2003).
Rudikoff et al., "Single amino acid substitution altering antigen-binding specificity" (1982) Proc. Natl. Acad. Sci. USA, 70:1979-1983.
Salfeld, "Development of a Fully Human Antibody to TNF by Phage Display Technology," IBC Conference, Antibody Engineering, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) Critical Reviews in Biotechnology, 12:437-462.

(56) References Cited

OTHER PUBLICATIONS

Santora et al., "Characterization of recombinant human monoclonal tissue necrosis factor-alpha antibody using cation exchange HPLC and capillary isoelectric focusing," Analytical Biochemistry, (1999) 275:98-108.

Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.

Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.

Schiestl et al. "Acceptable changes in quality attributes of glycosylated biopharmaceuticals" Nature Biotechnology, 29(4), 310-312 (2011).

Schwieterman, "Immunosuppression in Combination with Monoclonal Antibodies" in Biologic Agents in Autoimmune Disease (Mar. 2-4, 1995).

Senczuk et al. "Hydrophobic interaction chromatography in dual salt system increases protein binding capacity" Biotechnology and Bioengineering, 103(5), 930-935 (2009).

Seresht et al., "The impact of phosphate scarcity on pharmaceutical protein production in *S. cerevisiae*: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", *Anal. Biochem.*, 247(1):102-110 (1997).

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shih, "Effects of Anions on the Deamidation of Soy Protein". Journal of Food Science. 1991, 56: 452-454.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.

Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.

Tan et al. (Biotechnol. Appl. Biochem. (1999) 30, 59-64).

Taylor et al.,"Human immunoglobulin transgenes undergo rearrangement, somatic mutation and class switching in mice that lack endogenous IgM" (1994) *Int. Immunol.*, 6:579-591.

Teichmann, S. Declaration dated Dec. 7, 2010 from opposition proceedings in EP 0929578.

The MW Calculator available at the Sequence Manipulation Suite (see http://bioinformatics.org/sms2/index.html), downloaded Feb. 25, 2014.

The pI Calculator available at the Sequence Manipulation Suite (see <http://bioinformatics.org/sms2/index.html>), downloaded Feb. 25, 2014, p. 1).

The Statement on a Nonproprietary Name Adopted by the USAN Council for Adalimumab, p. 1, downloaded on May 19, 2011 from http://www.ama-assn.org/resources/doc/usan/adalimumab.doc.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjuqate Journal 21 :343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Lent PL, et al. "The impact of protein size and charge on its retention in articular cartilage" J Rheumatol. Aug. 1987;14(4):798-805.

Varasteh et al. Optimization of Anti-Rh D Immunoglobulin Stability in the Lyphiliization Process. Iranian Journal of Basic Medical Sciences, Spring 2008, vol. 11, No. 1. pp. 55-61.

Vaughan, "Human antibodies by design" (1998) *Nature Biotechnology*, 16:535-539.

Wagner et al., "Antibodies generated from human immunoglobulin miniloci in transgenic mice" (1994) *Nucl. Acids Res.* 22:1389-1393.

Wagner et al., "The diversity of antigen-specific monoclonal antibodies from transgenic mice bearing human immunoglobulin gene miniloci" (1994) *Eur. J. Immunol.*, 24:2672-2681.

Ward, "Binding activities of a repertoire of single immunoglobulin variable domains secreted from *Escherichia coli*" (1989) *Nature*, 341:544-546.

Wedemayer et al., "Structural insights into the evolution of an antibody combining site" (1997) *Science*, 276:1665-1669.

Wiendl et al. (BioDrugs. 2002;16(3):183-200).

Williams et al., "Kinetic analysis by stopped-flow radiationless energy transfer studies: effect of anions on the activity of carboxypeptidase A". Biochemistry. 1986, 25, 94-100.

Winter, "Humanized antibodies" (1993) *Immunol. Today*, 14(6):243-246.

Winter, "Making antibodies by phage display technology" (1994) *Annu. Rev. Immunol.*, 12:433-455.

Wurm, FM, "Production of recombinant protein therapeutics in cultivated mammalian cells", Nature Biotechnology 22(11):1393-1398, 2004.

(56) References Cited

OTHER PUBLICATIONS

Yigzaw et al., "Exploitation of the adsorptive properties of depth filters for host cell protein removal during monoclonal antibody purification," Biotechnology Progress, (2006) 22(1):288-296.
Yumioka et al., "Screening of effective col. rinse solvent for Protein-A chromatography," Protein Expression and Purification, (2010) 70(2): 218-223.
Zatarain-Rios E and Mannik M, "Charge-charge interactions between articular cartilage and cationic antibodies, antigens, and immune complexes," Arthritis Rheum. Nov. 1987;30(1 1):1265-73.
Zhang et al., "Isolation and characterization of charge variants using cation exchange displacement chromatography," 1218(31): 5079-5086, 2011.
Zou et al., "Dominant expression of a 1.3 Mb human Ig kappa locus replacing mouse light chain production" (1996) *FASEB J.*, 10:1227-1232.
Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.
Ahmed, M. U.et al., N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Andersen DC, The effect of cell-culture conditions on the oligosaccharide structures of secreted glycoproteins. Curr Opin Biotechnol. Oct. 1994;5(5):546-9.
Anonymous, "SACHEM Displacement Chromatography," Aug. 29, 2012, Retrieved from the internet: <http://www.displacementchromatography.com>, retrieved on Jul. 30, 2014.
Averginos, Gab '04 Abstracts—GE Healthcare Life Sciences, "HUMIRA manufacturing: challenges and the path taken", France, Oct. 3-5, 2004, published 2005, pp. 14-16.
Awdeh, Z.L., A.R. Williamson, and B.A. Askonas, One cell-one immunoglobulin. Origin of limited heterogeneity of myeloma proteins. Biochem J, 1970. 116(2): p. 241-8.
Bandyopadhyay S., et al. Physicochemical and functional characterization of a biosimilar adalimumab ZRC-3197, Biosimilars, 2015;5, pp. 1-18.
Barnes et al., "Stability of Protein Production from Recombinant Mammalian Cells," Biotechnology and Bioengineering, 81:6, Mar. 20, 2003, pp. 631-639.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf <http://www.bdbiosciences.com/external_files/Doc_Recon_2.0/ab/others/Phytone_Soytone.pdf>), (last accessed Jan. 8, 2015), 4 pages.
Bendtzen, K. et al. in "Auto-antibodies to IL-1α and TNFα in Normal Individuals and in Infectious and Immunoinflammatory Disorders" *The Physiological and Pathological Effects of Cytokines*, 447-52 (1990).
Biastoff, S.; et al.; Colorimetric Activity Measurement of a Recombinant Putrescine N-Methyltransferase from *Datura stramonium*; Planta Med. 2006, 72, 1136.
Burteau et al. (In Vitro Cell Dev Biol—Animal, Jul. / Aug. 2003. 39-291-296).

Byun, et al. Archives of Biochemistry and Biophysics, "Transport of anti-IL-6 binding fragments into cartilage and the effects of injury," 532 (2013), pp. 15-22.
Chang, T. & Wu, L., Methylglyoxal, oxidative street, and hypertension, Can. J. Physiol. Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.
Chaplen, FWR; A dissertation entitled Analysis of Methylglyoxal Metabolism in Mammalian Cell Culture; Univ. of Wisconsin-Madison 1996, 218 pages.
Chelius, D. et al.; Identification and Characterization of Deamidation Sites in the Conserved Regions of Human Immunoglobulin Gamma Antibodies, Anal. Chem. 2005, 77,6004-6011.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009. 81(15): p. 6449-57.
Chung et al. "Cetuximab-induced anaphylaxis and IgE specific for galactose-a-1,3-galactose" NEJM 358:11, 1109-1117 (2008).
Cordoba, A.J., et al., Non-enzymatic hinge region fragmentation of antibodies in solution. Journal of Chromatography B, 2005. 818(2): p. 115-121.
Crowell, C.K., et al., Amino acid and manganese supplementation modulates the glycosylation state of erythropoietin in a CHO culture system. Biotechnology and bioengineering, Feb. 15, 2007; 96(3):538-549.
Dai, S.; An Integrated Proteomic Analysis of Major Isoaspartyl-Containing Proteins in the Urine of Wild Type and Protein Llsoaspartate O-Methyltransferase-Deficient Mice; Anal. Chem. 2013, 85, 2423-2430.
Dionex Application Note 125 (Monitoring Protein Deamidation by Cation-Exchange Chromatography. 2009; pp. 1-7).
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Du et al., "Chromatographic analysis of the acidic and basic species of recombinant monoclonal antibodies" *MAbs*, Sep.-Oct. 2012; 4(5):578-85.
Ellison, Jay W. et al., "The Nucleotide Sequence of a Human Immunoglobulin Cγ1 Gene," Nucleic Acids Research, vol. 10, No. 13 (1982), 9 pages.
Emery, P. "Adalimumab therapy: Clinical findings and implications for integration into clinical guidelines for rheumatoid arthritis." *Drugs of Today*, 41(3): p. 155-163. (2005).
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Fahrner et al., "Industrial purification of pharmaceutical antibodies: development, operation, and validation of chromatography processes" Biotechnology and Genetic Engineering Reviews, 18, 2001, pp. 301-327.
Fleisher B., Mechanism of glycosylation in the Golgi apparatus. J Histochem Cytochem, Aug. 1983; 31(8):1033-1040.
Folk et al., "Carboxypeptidase B, Purification and Characterization of the Porcine Enzyme," J. Biological Chem, 1960, 235:2272-2277.
Gagnon, P., "Polishing methods for monoclonal IgG purification" Chapter 17, Taylor & Francis Group, LLC, pp. 491-505, 2007.
Gao et al. "Site-selective modifications of arginine residues in human hemoglobin induced by methylglyoxal." Biochemistry, 2006; pp. 15654-15660.

(56) References Cited

OTHER PUBLICATIONS

Gauthier, M. A.& Klok, H.-A. Arginine-Specific Modification of Proteins with Polyethylene Glycol Biomacromolecules; 2011, 12, 482-493.

Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.

Goochee CF The Oligosaccharides of Glycoproteins: Bioprocess Factors Affecting Oligosaccharide Structure and their Effect on Glycoprotein Properties. Nature Biotechnology Dec. 1991 1346-1355.

Goswami et al., "Developments and Challenges for mAb-Based Therapeutics," *Antibodies*, 2:452-500, 2013.

Gramer M Jet al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.

Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.

Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.

Harding et al., "Class switching in human immunoglobulin transgenic mice" (1995) *Ann. NY Acad. Sci.*, 764:536-547.

Harlow et al., Eds ("Antibodies: A Laboratory Manual" 1988. Cold Spring Harbor Laboratory Press, Chapter 7, pp. 245, 247,and 253).

Harris, R.J., et al., Identification of multiple sources of charge heterogeneity in a recombinant antibody. Journal of Chromatography B: Biomedical Sciences and Applications, 2001. 752(2): p. 233-245.

Harris, Reed J. et al., "Structural Characterization of a Recombinant CD4-IgG Hybrid Molecule," Eur. J. Biochem. 194:611-620 (1990).

Hills, A.E. et al., Metabolic control of recombinant monoclonal antibody N-glycosylation in GS-NS0 cells, Biotechnology and Bioengineering, Oct. 20, 2001; 75(2):239-251.

Hipkiss, A.; Can the beneficial effects of methionine restriction in rats be explained in part by decreased methylglyoxal generation resulting from suppressed carbohydrate metabolism?; Biogerontology 2012, 13, 633-636.

Hossler et al., "Optimal and consistent protein glycosylation in mammalian cell culture", Glycobiology; (2009), 19(9):936-949.

Hossler et al.; "Improvement of mammalian cell culture performance through surfactant enabled concentrated feed media"; Biotechnology Progress; 29(4):1023-1033 (2013).

Huang, L., et al., In Vivo Deamidation Characterization of Monoclonal Antibody by LC/MS/MS. Analytical Chemistry, 2005. 77(5): p. 1432-1439.

HUMIRA (adalimumab) prescribing information, Dec. 20, 2002, pp. 1-16.

HyClone™ CDM4CHO Catalog listing (last accessed Nov. 17, 2014).

ICH Topic Q6B "Specifications:Test Procedures and Acceptance Criteria for Biotechnological/Biological Products," Sep. 1999, pp. 1-17.

International Preliminary Report on Patentability for Application No. PCT/US2013/031352 dated Nov. 25, 2014, pp. 1-10.

International Preliminary Report on Patentability for Application No. PCT/US2013/031365, dated Mar. 3, 2015, 9 pages.

International Preliminary Report on Patentability for Application No. PCT/US2013/031389, dated Oct. 21, 2014, pp. 1-10.

International Preliminary Report on Patentability for Application No. PCT/US2013/031485, dated Oct. 21, 2014, pp. 1-8.

International Preliminary Report on Patentability for Application No. PCT/US2013/031681, dated Oct. 21, 2014, pp. 1-8.

International Preliminary Report on Patentability for Application No. PCT/US2013/041954, dated Nov. 25, 2014, pp. 1-14.

International Preliminary Report on Patentability for Application No. PCT/US2013/041958, dated Dec. 4, 2014, pp. 1-2.

International Search Report and Written Opinion for PCT/US2012/035266, dated Feb. 7, 2013 (corresponds to U.S. Appl. No. 13/547,020), 4 pages.

International Search Report and Written Opinion from PCT/US2013/065749 dated Mar. 18, 2014, 18 pages.

International Search Report and Written Opinion from PCT/US2014/024151 dated Aug. 7, 2014, pp. 1-16.

International Search Report for Application No. PCT/US2014/026606, Dated Dec. 8, 2014, 8 pages.

International Search Report for Application No. PCT/US2014/026636, Dated Jul. 29, 2014, 5 pages.

International Search Report from PCT/US2014/024256 dated Jul. 30, 2014, pp. 1-15.

Invitation to Pay Additional Fees for International Application No. PCT/US2013/065749, Dated May 27, 2014, pp. 1-8.

Invitation to Pay Additional Fees for International Application No. PCT/US2014/026606, Dated Jul. 8, 2014, pp. 1-8.

Jack, M.; Wright, D.; The Role of Advanced Glycation Endproducts and Glyoxalase I in Diabetic Peripheral Sensory Neuropathy; Transl. Res. 2012, 159, 355-365.

Jakubowski, H., Protein N-homocysteinylation: implications for atherosclerosis. Biomedicine; Pharmacotherapy, 2001. 55(8): p. 443-447.

Jayapal, Karthik P., et al., "Recombinant Protein Therapeutics from CHO Cells—20 Years and Counting," CHO Consortium, SBE Special Section, 40-47 (2007).

Jayme et al.; "Media formulation options and manufacturing process controls to safeguard against introduction of animal origin contaminants in animal cell culture"; Cytotechnology; 33:27-36 (2000).

Jefferis, R., Glycosylation of Recombinant Antibody Therapeutics. Biotechnology Progress, 2005.21(1): p. 11-16.

Johnson, K.A., et al., Cation exchange HPLC and mass spectrometry reveal C-terminal amidation of an IqG1 heavy chain. Analytical Biochemistry, 2007. 360(1): p. 75-83.

Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.

Kazuaki F et al "Enhancment of productivity of recombinant a-amidating enzyme by low temperature culture" Cytotechnology 31:85-94, 1999.

Kingkeohoi, S., Analysis of methylglyoxal metabolism in CHO celis grown in culture, Cytotechnology (2005) 48:1-13.

Kwon et al., "Production of lactic acid by *Lactobacillus rhamnosus* with vitamin-supplemented soybean hydrolysate", Enzyme Microb Technol. (2000), 26:209-215.

Leusch, "Failure to demonstrate TNFα-specific autoantibodies in human sera by ELISA and Western blot" (1991) *J. Immunol. Methods*, 139:145-47.

Li, Feng, et al., "Cell Culture Processes for Monoclonal Antibody Production," mAbs 2:5, 466-479 (Sep.-Oct. 2010).

Liu et al. "Recovery and purificaiton process development for monoclonal antibody production" MABS, 2(5), pp. 480-499 (2010).

Liu, H., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.

Liu, H., et al., Heterogeneity of monoclonal antibodies. Journal of Pharmaceutical Sciences, 2008. 97(7): p. 2426-2447.

Liu, M, et al.; Discovery of Undefined Protein Cross-Linking Chemistry: A Comprehensive Methodology Utilizing 18O-Labeling and Mass Spectrometry; Anal. Chem. 2013, 5900-5908.

Liu, M.et al.; Protein Isoaspartate Methyltransferase-Mediated 18O-Labeling of Isoaspartic Acid for Mass Spectrometry Analysis; Anal. Chem. 2011, 84, 1056-1062.

Lo, T.W. et al., Binding and modification of proteins by methylglyoxal under physiological conditions. A kinetic and mecha-

(56) References Cited

OTHER PUBLICATIONS nistic study with N alpha-acetylarginine, N alpha-acetyilysine, and N alpha-acetyllysine, and bovine serum albumin, Dec. 23, 1994, The Journal of Biological Chemistrv, 269, 32299-32305.
Manning, M., et al., *Stability of Protein Pharmaceuticals: An Update*. Pharmaceutical Research, 2010.27(4): p. 544-575.
Matthews, R. G.; et al.; Cobalamin-Dependent and Cobalamin-Independent Methionine Synthases: Are There Two Solutions to the Same Chemical Problem?; Hely. Chim. Acta 2003, 86, 3939-3954.
McAtee et al., "Isolation of monoclonal antibody charge variants by displacement chromatography," Current Protocols in Protein Science, 8.10-8.10.13, 2012.
Mehta, et al. "Purifying therapeutic monoclonal antibodies," Chemical Engineering Progress; May 2008, 104, 5; pp. S14-S20.
Mizuochi, T., et al., Structural and numerical variations of the carbohydrate moiety of immunoglobulin G. J Immunol, 1982. 129(5): p. 2016-20.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.
Ni, W.; Analysis of Isoaspartic Acid by Selective Proteolysis with Asp-N and Electron Transfer Dissociation Mass Spectrometry; Anal. Chem. 2010, 82,7485-7491.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trends in Biotechnology.
Parekh, R.B., et al., Association of rheumatoid arthritis and primary osteoarthritis with changes in the glycosylation pattern of total serum IgG. Nature, 1985. 316(6027): p. 452-7.
PCT/US2013/069702 International Search Report & Written Opinion mailed Jan. 31, 2014, 13 pages.
Perkins, M.; et. al. Determination of the Origin of Charge Heterogeneity in a Murine Monoclonal Antibody; M. Pharm. Res. 2000, 17, 1110-1117.
Quan, C., et al., A study in glycation of a therapeutic recombinant humanized monoclonal antibody: Where it is, how it got there, and how it affects charge-based behavior. Analytical Biochemistry, 2008.373(2): p. 179-191.
Rabbani, N.; Thornalley, P. J.; Glyoxalase in diabetes, obesity and related disorders; Semin. Cell Dev. Biol. 2011, 22, 309-317.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.

Roe, S. "Separation Based on Structure" Chapter 4, § 5.2, In, Protein Purification Methods; A Practical Approach, Harries, et al. Sep. 1989, p. 203.
Roy, B.M., et al., Toxic concentrations of exogenously supplied methy!glyoxal in hybridoma cell culture, Cytotechnology (2004) 46:97-107.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Sargent (pp. 1-3, Internet Archive captured Aug. 28, 2013, http://cellculturedish.com/2012/01 /cho-cells-the-top-expressionsystem-of-best-selling-biologic-drugs/).
Saxena, R. K. et al.; Microbial production and applications of 1 , 2-propanediol; Indian J. Microbiol. 2010,50,2-11.
Shen, Amy Y. et al., "Recombinant DNA Technology and Cell Line Development," from "Cell Culture Technology for Pharmaceutical and Cell-Based Therapies," CRC Press, 1995, 15-40.
Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.
Sigma Catalog "RPMI1640" (last accessed Jan. 22, 2015), 3 pages.
Sigma MSDS for RMPI1640 (last accessed Jan. 22, 2015), 6 pages.
Sundaram et al., "An innovative approach for the characterization of the isoforms of a monoclonal antibody product," Mabs, 3(6):505-512, 2011.
TESS database "HYCLONE" Trademark #76244963. Filing date Apr. 23, 2001. Live mark. Last accessed Jan. 21, 2015.
TESS database "HYCLONE" Trademark #85769283. Filing date Sep. 30, 2012. Live mark. Last accessed Jan. 21, 2015.
Tharmalingam et al.; "Pluronic Enhances the Robustness and Reduces the Cell Attachment of Mammalian Cells"; Molecular Biotechnology; 39(2):167-177 (2008).
The Kennedy Institute of Rheumatology, 1995 Annual Scientific Report, "Anti-TNF trials and studies of mechanisms of action".
United States Food and Drug Administration (FDA) Biological Licensing Application File No. 125057 (Adalimumab) (Dec. 31, 2002) (Last Accessed Mar. 4, 2015 at <http://www.fda.gov/Drugs/DevelopmentApprovalProcess/HowDrugsareDevelopedandApproved/ApprovalApplications/TherapeuticBiologicApplications/ucm080610.htm>), 1 page.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Vasilli, P. et al., The Pathophysiology of Tumor Necrosis Factors, Annu. Rev. Immunol. 10:411-452 (1992).
Vlasak, J. & Ionescu, R., *Heterogeneity of Monoclonal Antibodies Revealed by Charge-Sensitive Methods*. Current Pharmaceutical Biotechnology, 2008. 9(6): p. 468-481.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Williams, A. et al., Ion-Exchange Chromatography, Oct. 1998, Supplement 44, pp. 10-10-1-10-10-30.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, one page, Feb. 25, 2012.
Xiang, T., Chumsae, C. & Liu, H., Localization and Quantitation of Free Sulfhydryl in Recombinant Monoclonal Antibodies by Differ-

(56) References Cited

OTHER PUBLICATIONS ential Labeling with 12C and 13C Iodoacetic Acid and LC-MS Analysis. Analytical Chemistry, 2009. 81(19): p. 8101-8108.
Yuk, I.H. et al., Controlling Glycation of Recombinant Antibody in Fed Batch Cell Cultures, Nov. 2011, Biotechnoloqy and Bioenqineerinq, vol. 108, No. 11 pp. 2600-2610.
Zang, T.; et al.; Chemical Methods for the Detection of Protein N-Homocysteinylation via Selective Reactions with Aldehydes; Anal. Chem. 2009, 81, 9065-9071.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Babcock, James et al., "Partial Replacement of Chemically Defined Media with Plant-Derived Protein Hydrolysates," *BioPharm International*, vol. 23: 6. Jun. 2010, 6 pages.
Brock, Jonathan et al., "Detection and identification of arginine modifications on methylglyoxal-modified ribonuclease by mass spectrometric analysis," Journal of Mass Spectrometry, 2007; 42: 89-100.
Drew, Berry et al., "The Effects of Media Formulations on the Biochemical Profile of IgG Expressed in Sp2/0 Cells as Measured by Cation Exchange HPLC," European Society of Animal Cell Technology Meeting Jan. 2007, Poster #1115, 1 page.
Extended European Search Report for Application No. 13877986.3. Dated Aug. 4, 2014, 11 pages.
Goochee, C.F. "Bioprocess Factors Affecting Glycoprotein Oligosaccharide Structure." *Develop. Biol. Standard*, vol. 76 (1992). 95-104.
Grosvenor, Sally, "A New Era in Cell Culture Media Development," *BioPharm International*, Jul. 2012 vol. 25: 7, 7 pages.
Hossler, Patrick et al., "Targeted Shifting of Protein Glycosylation Profiles in Mammalian Cell Culture through Media Supplementation of Cobalt." *J. Glycobiol* vol. 3; 1.(2014). 9 pages.
Indian Patent Office—IPAIRS application status for 2285/MUM/2013—Application not yet published. Document found on internet at ipindiaonline.gov/in/patentsearch/search/index.aspx. Last accessed Apr. 13, 2015.
International Preliminary Report on Patentability for Application No. PCT/US2013/031380, dated Sep. 15, 2015, 13 pages.
International Preliminary Report on Patentability for Application No. PCT/US2013/065720, dated Sep. 24, 2015, 8 pages.
International Preliminary Report on Patentability for Application No. PCT/US2013/065749 dated Sep. 15, 2015, 10 pages.
International Preliminary Report on Patentability for Application No. PCT/US2013/065797, dated Sep. 24, 2015, 8 pages.
International Preliminary Report on Patentability for Application No. PCT/US2013/069702, dated Sep. 15, 2015, 8 pages.
International Preliminary Report on Patentability for Application No. PCT/US2014/024151, dated Sep. 15, 2015, 9 pages.
International Preliminary Report on Patentability for Application No. PCT/US2014/024256, dated Sep. 15, 2015, pp. 1-9.
International Preliminary Report on Patentability for Application No. PCT/US2014/026606, dated Sep. 15, 2015, 13 pages.
International Preliminary Report on Patentability for Application No. PCT/US2014/026636, dated Sep. 15, 2015, 9 pages.
International Search Report and Written Opinion from PCT/US2015/039773 dated Sep. 25, 2015, pp. 1-14.

International Search Report for Application No. PCT/US2015/038819 Dated Sep. 2, 2015, 12 pages.
Kunkel, Jeremy P., et al., "Dissolved oxygen concentration in serum-free continuous culture affects N-linked glycosylation of a monoclonal antibody," *Journal of Biotechnology*, 62 (1998), 55-71.
Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.
Restelli, Veronica, et al., "The Effect of Dissolved Oxygen on the Production and the Glycosylation Profile of Recombinant Human Erythropoietin Produced From CHO Cells," Biotechnology and Bioengineering, vol. 94, No. 3, (2006) 481-494.
Roy, Samar N. et al., "Secretion of Biologically Active Recombinant Fibrinogen by Yeast." *The Journal of Biological Chemistry*, vol. 270; 40 (1995). 23761-23767.
Scientific Discussion. Retrieved from the Internet: www.ema.europa.eu/dics/en_GB/document_library/EPAR_Sceintific_Discussion/human/00481/WC500050867.pdf [retrieved on Jun. 29, 2015], EMEA, 2004, 25 pages.
Seo, Jin Seok, et al., "Effect of culture pH on recombinant antibody production by a new human cell line, F2N78, grown in suspension at 33.0° C. and 37.0° C.," *Appl. Microbiol Biotechnol.*, vol. 97 (2013). 5283-5291.
Shirato, Ken et al., "Hypoxic regulation of glycosylation via the N-acetylglucosamine cycle." *J. Clin. Biochem. Nutr.* vol. 48; 1 (2011). 20-25.
Tebbey, Paul W., et al., "Consistency of quality for the glycosylated monoclonal antibody Humira (adalimumab)," MAbs, Sep. 3, 2015;7(5); 805-11.
Wang, Tina et al., "Exploring Post-translational Arginine Modification Using Chemically Synthesized Methylglyoxal Hydroimidazolones," *J. Am. Chem. Soc.*, 2012, 134, pp. 8958-8967.
Zhang, Y. et al., "Specificity and Mechanism of Metal Ion Activation in UDP-galactose: β-Galactoside-α-1,3-galactosyltransferase." *J. Biological Chemistry* vol. 276; 15 (2001). 11567-11574.
"Preliminary Data From Two Clinical Trials Demonstrate Abbott Laboratories' HUMIRA Improved Symptoms of Psoriatic Arthritis and Ankylosing Spondylitis" *PR Newswire* (2004).
*Abbott Laboratories Announces Positive Results of Phase ll HUMIRA (R) (adalimumab) Study in Psoriasis*, P.R. Newswire. (2004).
Alessandri, L. et al., "Increased serum clearance of oligomannose species present on a human IgG1 molecule." *mAbs*, (2012), 4(4); 509-520.
Amersham Biosciences, *Antibody Purification Handbook* (2002).
An, Zhiqiang editor, "Therapeutic Monoclonal Antibodies: From Bench to Clinic," 2009 edition, John Wiley & Sons, Hoboken, NJ, US, pp. 73-76, section 3.4.3.
Andersen et al., *Protein Glycosylation: Analysis, Characterization, and Engineering*, Encyclopedia of Industrial Biotechnology (2011).
Anumula et al., "Quantitative glycan profiling of normal human plasma derived immunoglobulin and its fragments Fab and FcO" (2012) J. Immunol. Methods, 382:167-176.
Arakawa et al., *Biotechnology applications of amino acids in protein purification and formulations*, Amino Acids, vol. 33, pp. 587-605 (2007).
Arend et al., "Inhibition of the production and effects of interleukins-1 and tumor necrosis factor α in rheumatoid arthritis" (1995) Arth. Rheum., 38(2):151-160.
Ashkenazi et al., "Immunoadhesins: An alternative to human monoclonal antibodies" (1995) Methods, 8(2): 104-115.
Avgerinos, *HUMIRA manufacturing: challenges and the path taken*, Extended Reports from the 3rd International Symposium on Downstream Processing of Genetically Engineered Antibodies and Related Molecules (Oct. 3-5, 2004).
Babcock et al., *Partial Replacement of Chemically Defined CHO Media with Plant-Derived Protein Hydrolysates*, in Proceedings of the 21st Annual Meeting of the European Society for Animal Cell Technology (ESACT), Dublin, Ireland, Jun. 7-10, 2009, pp. 295-298 (Springer Netherlands).
Barb et al., "Branch-specific sialylation of IgG-Fc glycans by ST6Gal-I" Biochemistry, (2009) 48:9705-9707.

(56) References Cited

OTHER PUBLICATIONS

Bartelds et al., "Development of antidrug antibodies against adalimumab and association with disease activity and treatment failure during long-term follow-up" (2011) JAMA, 305(14):1460-1468.
Baynes et al., *Role of Arginine in the Stabilization of Proteins against Aggregation*, Biochemistry, vol. 44, pp. 4919-4925 (2005).
Bertolini et al., Stimulation of bone resorption and inhibition of bone formation in vitro by human tumour necrosis factors, (1986) Nature 319:516-518.
Bibila & Robinson, *In Pursuit of the Optimal Fed-Batch Process for Monoclonal Antibody Production*, Biotechnol. Prog., 11:1-13 (1995).
Biblia, T.A. et al., "In Pursuit of the Optimal Fed-Batch Process for Monoclonal Antibody Production", Biotechnol. Prog 11(1):1-13, Jan.-Feb. 1995.
Bird et al. "Single-chain antigen-binding proteins." Science. (1988) 242:423-426.
Borys et al., *Ammonia Affects the Glycosylation Patterns of Recombinant Mouse Placental Lactogen-I by Chinese Hamster Ovary Cells in a pH-Dependent Manner*, Biotechnology and Bioengineering, 43:505-514 (1994).
Braun (2002), Anti-tumor necrosis factor a therapy for ankylosing spondylitis: international experience, Ann. Rheum. Dis. 61(Suppl. III):iii51-iii60.
Butler, Animal cell cultures: recent achievements and perspectives in the production of biopharmaceuticals, Appl. Microbiol. Biotechnol., 68: 283-291 (2005).
Butler, *Optimisation of the Cellular Metabolism of Glycosylation for Recombinant Proteins Produced by Mammalian Cell Systems*, Cytotechnology, 50:57-76 (2006).
Carpenter et al., Rational Design of Stable Protein Formulations: Theory and Practice, 101 pages, (2002).
Champion et al., *Defining Your Product Profile and Maintaining Control Over It, Part 2*, BioProcess Technical, vol. 3, pp. 52-57 (Sep. 2005).
Chen et al., *Effects of Elevated Ammonium on Glycosylation Gene Expression in CHO Cells*, Metabolic Engineering, 8:123-132 (2006).
Chun et al., *Usability of size-excluded fractions of soy protein hydrolysates for growth and viability of Chinese hamster ovary cells in protein-free suspension culture*, Bioresource Technology, 98:1000-1005 (2007).
Clincke et al. "Effect of iron sources on the glycosylation macroheterogeneity of human recombinant IFN-y produced by CHO cells during batch processes," BMC Proceedings (Nov. 22, 2011) 5(Suppl 8):PI14, pp. 1-2.
Clincke et al. "Characterization of metalloprotease and serine protease activities in batch CHO cell cultures: control of human recombinant IFN-γproteolysis by addition of iron citrate," BMC Proceedings (Nov. 22, 2011) 5(Suppl 8):P115, pp. 1-3.
Clinical trial No. NCT00085644 "Human Anti-tumor Necrosis Factor (TNF) Monoclonal Antibody Adalimumab in Subjects With Active Ankylosing Spondylitis (ATLAS)" (2004).
Clinical trial No. NCT00235105 "Adalimumab in Early Axial Spondyloarthritis (Without Radiological Sacroiliitis): Placebo Controlled Phase Over 3 Months Followed by a 9 Months Open Extension Phase" (2005).
Coffman et al., *High-Throughput Screening of Chromatographic Separations: 1. Method Development and Column Modeling*, Biotechnology & Bioengineering, 100:605-618 (2008).
Commercially Available HUMIRA product, approved by the FDA in Dec. 2002 and available in Jan. 2003.
CPMP Policy Statement on DNA and Host Cell Proteins (HCP) Impurities, Routine Testing versus Validation Studies, EMEA, Jun. 10, 1997.
Cromwell, *Avastin: highlights from development*, Extended Reports from the 3rd International Symposium on Downstream Processing of Genetically Engineered Antibodies and Related Molecules (Oct. 3-5, 2004).
Cruz et al., *Process development of a recombinant antibody/interleukin-2 fusion protein expressed in protein-free medium by BHK cells*, Journal of Biotechnology, 96:169-183 (2002).
Cumming, *Glycosylation of recombinant protein therapeutics: control and functional implications*, Glycobiology, 1(2):115-130 (1991).
Das et al., "Delivery of rapamycin-loaded nanoparticle down regulates ICAM-1 expression and maintains an immunosuppressive profile in human CD34+ progenitor-derived dendritic cells" (2008) J Biomed Mater Res A., 85(4):983-92.
Davis et al., Recombinant Human Tumor Necrosis Factor Receptor (Etanercept) for Treating Ankylosing Spondylitis, Arthritis & Rheumatism 48:3230-3236 (2003).
Del Val et al., *Towards the Implementation of Quality by Design to the Production of Therapeutic Monoclonal Antibodies with Desired Glycosylation Patterns*, American Institute of Chemical Engineers, Biotechnol. Prog., 26(6):1505-1527 (2010).
Eason et al., "Inhibition of the effects of Tnf in renal allograft recipients using recombinant human dimeric tumor necrosis factor receptors" (1995) Transplantation, 59(2):300-305.
Ebersbach et al., "Affilin-novel binding molecules based on human gamma-B-crystallin, an all beta-sheet protein" (2007) J. Mol. Biol., 372 (1): 172-85.
Elliot et al., "Randomised double-blind comparison of chimeric monoclonal antibody to tumour necrosis factor alpha (cA2) versus placebo in rheumatoid arthritis" (1994) Lancet, 344(8930):1105-1110.
EMEA, *Avastin Scientific Discussion* (2005).
Endres, *Soy Protein Products Characteristics, Nutritional Aspects, and Utilization*, 2001 (AOCS Press, Champaign, Illinois).
Ertani et al., *Biostimulant activity of two protein hydrolyzates in the growth and nitrogen metabolism of maize seedlings*, J. Plant Nutr. Soil Sci., 000:1-8 (2009).
Espinosa-Gonzalez, *Hydrothermal treatment of oleaginous yeast for the recovery of free fatty acids for use in advanced biofuel production*, Journal of Biotechnology, 187:10-15 (2014).
Exposure Factors Handbook, U.S. Environmental Protection Agency (1997).
Falconer et al., *Stabilization of a monoclonal antibody during purification and formulation by addition of basic amino acid excipients*, vol. 86, pp. 942-948 (2011).
Farnan et al., Multiproduct High-Resolution Monoclonal Antibody Charge Variant Separations by pH Gradient Ion-Exchange Chromatography, Analytical Chem., vol. 81, No. 21, pp. 8846-8857 (2009).
Fauchère et al., *Amino acid side chain parameters for correlation studies in biology and pharmacology*, Int. J. Peptide Res., vol. 32, pp. 269-278 (1988).
Fava et al., "Critical role of peripheral blood phagocytes and the involvement of complement in tumour necrosis factor enhancement of passive collagen-arthritis" (1993) Clin. Exp. Immunol., 94(2):261-266.
Felver et al., "Plasma tumor necrosis factor α predicts decreased long-term survival in severe alcoholic hepatitis" (1990) Alcohol. Clin. Exp. Res. 14(2):255-259.
Fernandes, "Demonstrating Comparability of Antibody Glycosylation during Biomanufacturing," European Biopharmaceutical Review. (2005) pp. 106-110.
Fietze et al., "Cytomegalovirus infection in transplant recipients the role of tumor necrosis factor" (1994) Transplantation, 58(6):675-680.
Follmam et al., Factorial screening of antibody purification processes using three chromatography steps without protein A, J. Chromatography A, vol. 1024, pp. 79-85 (2004).
Foong et al., *Anti-tumor necrosis factor-alpha-loaded microspheres as a prospective novel treatment for Crohn's disease fistulae*, Tissue Engineering, Part C: Methods, 16(5):855-64 (2010).
Franek et al., Plant Protein Hydrolysates: Preparation of Defined Peptide Fractions Promoting Growth and Production in Animal Cells Cultures, Biotech. Progress, 16:688-692 (2000).
FrieslandCampina Domo. *Product Data Sheet: Proyield Pea PCE80B*. Paramus, NJ: Aug. 2011.

(56) References Cited

OTHER PUBLICATIONS

FrieslandCampina Domo. *Product Data Sheet: Proyield Soy SE70M-UF.* Paramus, NJ: Apr. 2011.
FrieslandCampina Domo. *Product Data Sheet: Proyield Wheat WGE80M-UF.* Paramus, NJ: Apr. 2011.
FrieslandCampina Domo. *Product Information Sheet: CNE50M-UF.* Zwolfe, NL: Jun. 2010.
Gagnon et al., *Technology trends in antibody purification,* J. Chromatography A., vol. 1221, pp. 57-70 (available online Oct. 2011).
Gawlitzek et al., *Ammonium Alters N-Glycan Structures of Recombinant TNFR-IgG: Degradative Versus Biosynthetic Mechanisms,* Biotechnology and Bioengineering, 68(6):637-646 (2000).
Gawlitzek et al., *Identification of Cell Culture Conditions to Control N-Glycosylation Site-Occupancy of Recombinant Glycoproteins Expressed in CHO cells,* 103:1164-1175 (2009).
Gibbs, *Production and Characterization of Bioactive Peptides from Soy Fermented Foods and Their Hydrolysates,* Dissertation, McGill University, Montreal Quebec (1999).
Gilar et al., "Characterization of glycoprotein digests with hydrophilic interaction chromatography and mass spectrometry" (2011) Analytical Biochem., 417:80-88.
Giroir et al., "Inhibition of tumor necrosis factor prevents myocardial dysfunction during burn shock" (1994) Am. J. Physiol., 267(1 Pt 2):H118-24.
Goetze, A. et al., "High-mannose glycans on the Fc region of therapeutic IgG antibodies increase serum clearance in humans." *Glycobiology* (2011), 21(7); 949-959.
Gong et al., *Fed-Batch Culture Optimization Of A Growth-Associated Hybridoma Cell Line In Chemically Defined Protein-Free Media,* Cytotechnology, 52:25-38 (2006).
Goochee et al., *Environmental Effects on Protein Glycosylation,* Biotechnology, 8:421-427 (1990).
Gorfien et al., *Optimized Nutrient Additives for Fed-Batch Cultures,* BioPharm International, 16:34-40 (2003).
Grabulovski et al., "A Novel, Non-immunogenic Fyn SH3-derived Binding Protein with Tumor Vascular Targeting Properties" (2007) J Biot Chem 282, (5): 3196-3204.
Gramer et al. "Modulation of antibody galactosylation through feeding of uridine, manganese chloride, and galactose," Biotechnology and Bioengineering. (Jul. 1, 2011) 108(7):1591-1602.
Gross et al. "Involvement of various organs in the initial plasma clearance of differently glycosylated rat liver secretory proteins," Eur. J. Biochem. (1988) 173(3):653-659.
Gu et al., *Influence of Primatone RL Supplementation on Sialylation of Recombinant Human Interferon-γ Produced by Chinese Hamster Ovary Cell Culture Using Serum-Free Media,* Biotechnology and Bioengineering, 56(4):353-360 (1997).
Guidance for Industry—Q6B Specifications: Test Procedures and Acceptance Criteria for Biotechnological/Biological Products, Aug. 1999.
Guile et al., "A rapid high-resolution high-performance liquid chromatographic method for separating glycan mixtures and analyzing oligosaccharide profiles" (1996) Anal Biochem., 240(2):210-26.
Guse et al., *Purification and analytical characterization of an anti-CD4 monoclonal antibody for human therapy,* J. of Chromatography A, 661:13-23 (1994).
Haddadi et al., "Delivery of rapamycin by PLGA nanoparticles enhances its suppressive activity on dendritic cells" (2008) J Biomed Mater Res A., 84A(4):885-98.
Haibel (2005) *Arthritis and Rheumatism* 64(Suppl. III):316.
Haibel et al. (2004) *Arthritis and Rheumatism* 50(9):S217-18.
Hansen et al., "The role of tumor necrosis factor-alpha in acute endotoxin-induced hepatotoxicity in ethanol-fed rats" (1994) Hepatology, 20(2):461-474.
Hansen et al., *Extra- and intracellular amino acid concentrations in continuous Chinese hamster ovary cell culture,* Appl. Microbiol. Biotechnol., 41:560-564 (1994).
Harris et al., *Current Trends in Monoclonal Antibody Development and Manufacturing,* Chapter 12, pp. 193-205 (2010).

Hayter et al, *Chinese hamster ovary cell growth and interferon production kinetics in stirred batch culture,* Applied Microbiol. Biotech., 34:559-564 (1991).
Heeneman et al., *The concentrations of glutamine and ammonia in commercially available cell culture media,* J. Immunological Methods, 166:85-91(1993).
Hober, et al. "Protein A chromatography for antibody purification", J. Chromatography B, vol. 848 (2007) pp. 40-47.
Hong et al., *Substitution of glutamine by glutamate enhances production and galactosylation of recombinant IgG in Chinese hamster ovary cells,* Applied Microbiol. Biotech., 88:869-876 (2010).
Huang et al., *Nitrogen metabolism of asparagine and glutamate in Vero cells studied by 1H/15N NMR spectroscopy,* Applied Microbiol. Biotech., 77:427-436 (2007).
Hussain et al., "Hepatic expression of tumour necrosis factor-alpha in chronic hepatitis B virus infection" (1994) J. Clin. Pathol., 47:1112-1115.
Huston et al. "Protein engineering of antibody binding sites: recovery of specific activity in an anti-digoxin single-chain Fv analogue produced in *Escherichia coli*," Proc. Natl. Acad. Sci. USA(1988) 85:5879-5883.
International Conference on Harmonisation of Technical Requirements for Registration of Pharmaceuticals for Human Use, *Specifications: Test Procedures and Acceptance Criteria for Biotechnological/Biological Products Q6B,* Mar. 10, 1999.
International Preliminary Report on Patentability for Application No. PCT/US2014/059127, dated Apr. 14, 2016, 15 pages.
International Preliminary Report on Patentability for Application No. PCT/US2014/065793, dated May 17, 2016, 13 pages.
International Search Report and Written Opinion for Application No. PCT/US2014/058991, completed Dec. 18, 2014, 15 pages.
International Search Report and Written Opinion for Application No. PCT/US2014/065793, dated Jul. 27, 2015, 20 pages.
International Search Report and Written Opinion from PCT/US2015/042846 dated Feb. 2, 2016, pp. 1-22.
International Search Report with Written Opinion corresponding to International Patent Application No. PCT/US2014/059127, mailed May 7, 2015, 21 pages.
Invitation to Pay Additional Fees for International Application No. PCT/US2014/058991, mailed Jan. 15, 2015, 6 pages.
Invitation to Pay Additional Fees for International Application No. PCT/US2014/059127, dated Jan. 15, 2015, 6 pages.
Invitation to Pay Additional Fees for International Application No. PCT/US2014/065793, dated May 4, 2015, 15 pages.
Jacob et al., Scale-up of Antibody Purification, Antibodies, vol. 1: Production & Purification, (2004).
Karnoup et al., *O-Linked glycosylation in maize-expressed human IgA1,* Glycobiology, 15(10):965-981 (2005).
Kaufman et al., "Amplification and expression of sequences cotransfected with a modular dihydrofolate reductase complementary dna gene" (1982) Mol. Biol., 159(4):601-621.
Kaufman et al., *Depletion of manganese within the secretory pathway inhibits O-linked glycosylation in mammalian cells,* Biochemistry, 33(33):9813-9 (1994).
Kelley et al., *Downstream Processing of Monoclonal Antibodies: Current Practices and Future Opportunities,* Process Scale Purification of Antibodies (2009).
Kim et al., *Glycosylation pattern of humanized IgG-like bispecific antibody produced by recombinant CHO cells,* Applied Microbiol. Biotech., 85:535-542 (2010).
Kipriyanov et al. "Recombinant single-chain Fv fragments carrying C-terminal cysteine residues: production of bivalent and biotinylated miniantibodies," Molecular Immunology, (1994) 31(14):1047-1058 F.
Kipriyanov et al., "Single-chain antibody streptavidin fusions: tetrameric bifunctional scFv-complexes with biotin binding activity and enhanced affinity to antigen," Human Antibodies and Hybridomas.(1995) 6(3):93-101.
Kobak, Osteonecrosis and monoarticular rheumatoid arthritis treated with intra-articular adalimumab, *S. Mod Rheumatol,* 18, 290-292, Feb. 20, 2008.

(56) References Cited

OTHER PUBLICATIONS

Koide et al., "Monobodies: antibody mimics based on the scaffold of the fibronectin type III domain" (2007), Methods Mol. Biol., 352: 95-109.

Konig et al., "Tumor necrosis factor α and interleukin-1 stimulate bone resorption in vivo as measured by urinary [3H] tetracycline excretion from prelabeled mice" (1988) J. Bone Miner. Res., 3(6):621-627.

Kramarczyk et al., *High-Throughput Screening of Chromatographic Separations: II. Hydrophobic Interaction*, 100: 708-720 (2008).

Krehenbrink et al., "Artificial Binding Proteins (Affitins) as Probes for Conformational Changes in Secretin PuID" (2008) J. Mol. Biol., 383 (5): 1058-68.

Kunkel et al., "Comparisons of the Glycosylation of a Monoclonal Antibody Produced under Nominally Identical Cell Culture Conditions in Two Different Bioreactors" (2000) Biotechnol. Prog., 16(3): 462-470.

Kurano et al., *Growth behavior of Chinese hamster ovary cells in a compact loop bioreactor. 2. Effects of medium components and waste products*, J. Biotechnol., 15(1-2):113-128 (1990).

Lain et al., *Development of a High-Capacity MAb Capture Step Based on Cation-Exchange Chromatography, BioProcess Int'l*, vol. 7, pp. 26-34 (May 2009).

Lazar et al., *Matrix-assisted laser desorption/ionization mass spectrometry for the evaluation of the C-terminal lysine distributon of a recombinant monoclonal antibody*, Rapid Communications in Mass Spectrometry, vol. 18, pp. 239-244 (2004).

Leader et al., *Agalactosyl IgG in Aggregates from the Rheumatoid Joint*, Br. J. Rheumatol., 35:335-341 (1996).

Leavitt et al. "Impaired Intracellular Migration and Altered Solubility of Nonglycosylated Glycoproteins of Vesicular Stomatitis Virus and Sindbis Virus," J. Biol. Chem. (1977) 252(24):9018-9023.

Lerner et al., "Tumor necrosis factors α and β can stimulate bone resorption in cultured mouse calvariae by a Prostaglandin-independent mechanism" (1993) J. Bone Miner. Res., 8(2):147-155.

Lienqueo et al., *Mathematical correlations for predicating protein retention times in hydrophobic interaction chromatography*, 978:71-79 (2002).

Ling et al., *Analysis of Monoclonal Antibody Charge Heterogeneity Using Ion-Exchange Chromatography on a Fully Biocompatible HPLC System*, Dionex (2009).

Liu et al., "The significance of changes in serum tumour necrosis factor (TNF) activity in severely burned patients" (1994) Burns, 20(1):40-44.

Lobo-Alfonso et al., *Benefits and Limitations of Protein Hydrolysates as Components of Serum-Free Media for Animal Cell Culture Applications, Protein Hydrolysates in Serum Free Media*, GIBCO Cell Culture, Invitrogen Corporation, Grand Island, New York, Chapter 4:55-78 (2010).

Lowe et al. "A Genetic Approach to Mammalian Glycan Function," Annu. Rev. Biochem. (2003) 72:643-691.

Lu et al., *Recent Advancement in Application of Hydrophobic Interaction Chromatography for Aggregate Removal in Industrial Purification Process*, 10:427-433 (2009).

Lubinieki et al., *Comparability assessments of process and product changes made during development of two different monoclonal antibodies*, Biologicals, vol. 39, pp. 9-22 (2011).

Luksa et al., *Purification of human tumor necrosis factor by membrane chromatography*, J. Chromatography A, 661:161-168 (1994).

Lund et al., *Control of IgG/Fc Glycosylation: A Comparison of Oligosaccharides from Chimeric Human/Mouse and Mouse Subclass Immunoglobulin Gs*, Molecular Immunology, 30(8):741-748 (1993).

MacDonald et al., "Tumour necrosis factor-alpha and interferon-gamma production measured at the single cell level in normal and inflamed human intestine" (1990) Clin. Exp. Immunol, 81(2):301-305.

Matsumoto et al., *Autoantibody Activity of IgG Rheumatoid Factor Increases with Decreasing Levels of Galactosylation and Sialylation*, J. Biochemistry, 128:621-628 (2000).

McCauley et al., "Altered cytokine production in black patients with keloids" (1992) J. Clin. Immunol., 12(4):300-308.

McClain et al., "Increased tumor necrosis factor production by monocytes in alcoholic hepatitis" (1989) Hepatology, 9(3):349-351.

McCue et al., *Effect of phenyl sepharose ligand density on protein monomer/aggregate purification and separation using hydrophobic interaction chromatography*, J. of Chromatography A, 1216:209-909 (2009).

McLeod, "Adalimumab, etanercept and infliximab for the treatment of ankylosing spondylitis: a systematic review and economic evaluation," Health Technol. Assess. 11(28):1-158 (2006).

Meert et al., *Characterization of Antibody Charge Heterogeneity Resolved by Preparative Immobilized pH Gradients*, Analytical Chem., vol. 82, pp. 3510-3518 (2010).

Melter et al., *Adsorption of monoclonal antibody variants on analytical cation-exchange resin*, J. Chromatography A, vol. 1154, pp. 121-131 (2007).

Millward et al. "Effect of constant and variable domain glycosylation on pharmacokinetics of therapeutic antibodies in mice," Biologicals.(2008) 36(1):41-47.

Mizrahi, *Primatone RL in mammalian cell culture media*, Biotechnol. Bioeng., 19:1557-1561 (1977).

Moller et al., "Monoclonal antibodies to human tumor necrosis factor α: In vitro and in vivo application" (1990) Cytokine 2(3):162-169.

Moloney and Haltiwanger, *The O-linked fucose glycosylation pathway: indentification and characterization of a uridien diphosphoglucose: fucose-β1,3-glucosyltransferase activity from Chinese hamster ovary cells*, Glycobiology, 9:679-87 (1999).

Morgan et al. "Designing Biobetter Monoclonal Antibody Therapeutics by Glycoengineering," International Pharmaceutical Industry. (2011) pp. 38-44.

Nixon et al., "Engineered protein inhibitors of proteases" (2006) Curr Opin Drug Discov Devel, 9(2): 261-8.

Nyberg et al., *Metabolic Effects on Recombinant Interferon-65 Glycosylation in Continuous Culture of Chinese Hamster Ovary Cells*, Biotech. Bioeng., 62(3):336-347 (1999).

Nygren et al., "Alternative binding proteins: affibody binding proteins developed from a small three-helix bundle scaffold" (2008) FEBS J., 275 (11):2668-76.

Onda et al., *Reduction of the Nonspecific Animal Toxicity of Anti-Tac (Fv)-PE38 by Mutations in the Framework Regions of the Fv Which Lower the Isoelectric Point*, J. Immunology, vol. 163, pp. 6072-6077 (1999).

Pacesetter, Beckman Coulter Newsletter, vol. 3, Issue 1 (Apr. 1999).

Packer et al., "A general approach to desalting oligosaccharides released from glycoproteins" (1998) Glycoconj J., 15(8):737-47.

Proteus, "Protein A Antibody Purification Handbook," Pro-Chem Inc., 2005, pp. 1-52.

Raju et al. "Galactosylation variations in marketed therapeutic antibodies," MABS. (May 1, 2012) 4(3):385-391.

Raju et al., "Glycoengineering of Therapeutic Glycoproteins: In Vitro Galactosylation and Sialylation of Glycoproteins with Terminal N-Acetylglucosamine and Galactose Residues" (2001) Biochemistry, 40(30):8868-8876.

Raju, *Terminal sugars of Fc glycans influence antibody effector functions of IgGs*, Current Opinion in Immunology, 20:471-478 (2008).

Rankin et al., "The therapeutic effects of an engineered human anti-tumour necrosis factor alpha antibody(CDP571) in rheumatoid arthritis" (1995) Br. J. Rheumatol., 34:334-342.

Rao et al., *mAb Heterogeneity Characterization: MabPac Strong Cation-Exchanger Columns Designed to Extend Capabilities of mAb Analysis*, Tutorials (Mar. 15, 2011).

Rao et al., *Separation of Monoclonal Antibodies by Weak Cation-Exchange Chromatography Using ProPac and ProSwift Columns*, Dionex (available online 2010).

Remy et al., "Zinc-finger nucleases: A powerful tool for genetic engineering of animals" (2010) Transgenic Res., 19(3): 363-71.

(56) References Cited

OTHER PUBLICATIONS

Rivinoja et al, *Elevated Golgi pH Impairs Terminal NL Glycosylation by Inducing Mislocalization of Golgi Glycosyltransferases*, J. Cell. Physiol., 220:144-154 (2009).
Robinson et al., *Characterization of a Recombinant Antibody Produced in the Course of a High Yield Fed-Batch Process*, Biotech. Bioeng., 44:727-735 (1994).
Rodriguez et al., *Enhanced Production of Monomeric Interferon-â by CHO Cells through the Control of Culture Conditions*, Biotechnol. Prog., 21:22-30 (2005).
Rosolem et al., *Manganese uptake and redistribution in soybean as affected by glyphosate*, Rev. Bras. Ciênc. Solo, 34:1915-1922 (2010).
Rouiller et al. "Effiect of hydrocortisone on the production and glycosylation of an Fc-Fusion protein in CHO cell cultures," Biotechnology Progress.(May 2012) 28(3):803-813.
Rudd et al. "Glycosylation and the Immune System," Science. (2001) 291(5512):2370-2376.
Rudwaleit et al., Adalimumab is effective and well tolerated in treating patients with ankylosing spondylitis who have advanced spinal fusion, *Rhematology*; 48; 551-557 (2009).
Russell et al., "Targets for sepsis therapies: Tumor necrosis factor versus interleukin-1" (1993) Curr. Opin. Biotech., 4:714-721.
Santiago et al., "Targeted gene knockout in mammalian cells by using engineered zinc-finger nucleases" (2008) Proc. Natl. Acad. Sci. USA., 105(15):5809-14.
Santora et al., *Determination of Recombinant Monoclonal Antibodies and Noncovalent Antigen TNFα Trimer Using Q-TOF Mass Spectrometry*, Spectroscopy, 17(5):50-57 (2002).
Scales et al., "Hepatic ischemia/reperfusion injury: importance of oxidant/tumor necrosis factor interactions" (1994) Am. J. Physiol., 267 (6 Pt 1):G1122-1127.
Schenerman et al., *CMC Strategy Forum Report*, BioProcess Technical (2004).
Schlaeger E.-J., *The protein hydrolysate, Primatone RL, is a cost-effective multiple growth promoter of mammalian cell culture in serum-containing and serum-free media and displays anti-apoptosis properties*, J. Immunol. Meth., 194:191-199 (1996).
Serrick et al., "The early release of interleukin-2, tumor necrosis factor-alpha and interferon-gamma after ischemia reperfusion injury in the lung allograft" (1994) Transplantation, 58(11):1158-1162.
Shankar et al., "Evaluation of the role of second messenger systems in tumor necrosis factor-stimulated resorption of fetal rat limb bones" (1993) Bone, 14(6):871-876.
Sheffield Bioscience, Bio-Science Technical Manual: Supplements for cell culture, fermentation, and diagnostic media, 43 pages (2011).
Shen et al., *Characterization of yeastolate fractions that promote insect cell growth and recombinant protein production*, Cytotechnology, 54:25-34 (2007).
Sheron et al., "Increased production of tumour necrosis factor alpha in chronic hepatitis B virus infection" (1991) J. Hepatol., 12(2):241-245.
Shi et al., *Real Time Quantitative PCR as a Method to Evaluate Xenotropic Murine Leukemia Virus Removal During Pharmaceutical Protein Purification*, Biotechnology & Bioengineering, vol. 87, No. 7, pp. 884-896 (Sep. 2004).
Shibuya et al., "The elderberry (*Sambucus nigra L.*) bark lectin recognizes the Neu5Ac(alpha 2-6)Gal/GalNAc sequence" (1987) J. Biol. Chem., 262(4): 1596-1601.
Shields et al. "Lack of Fucose on Human IgGI N-Linked Oligosaccharide Improves Binding to Human FcyRIII and Antibody-dependent Cellular Toxicity," J. Biol. Chem. (2002) 277(30):26733-26740.
Shim, H., "One target, different effects: a comparison of distinct therapeutic antibodies against the same targets." Experimental and Molecular Medicine, vol. 43, pp. 539-549, Oct. 2011.
Shukla et al., *Downstream processing of monoclonal antibodies—Application of platform approaches*, J. of Chromatography B, 848:28-39 (2007).
Shukla et al., eds., *Process Scale Bioseparations for the Biopharmaceutical Industry*, (Taylor & Francis Group, Boca Raton FL) (2006).
Shukla et al., *Recent advances in large-scale production of monoclonal antibodies and related proteins*, Trends in Biotechnology, 28(5):253-261 (2010).
Shukla et al., *Strategies to Address Aggregation During Protein a Chromatography*, BioProcess International, 3:36-44 (2005).
Siemensma et al., Towards an Understanding of How Protein Hydrolysates Stimulate More Efficient Biosynthesis in Cultured Cells: *Protein Hydrolysates in Biotechnology*, Bio-Science, 36 pages (2010).
Silverman et al., "Multivalent avimer proteins evolved by exon shuffling of a family of human receptor domains" (2005) Nat. Biotechnol., 23 (12): 1556-61.
Skerra et al., "Alternative binding proteins: Anticalins—harnessing the structural plasticity of the lipocalin ligand pocket to engineer novel binding activities kerra" (2008) FEBS J., 275 (11): 2677-83.
Stumpp et al., "DARPins: A new generation of protein therapeutics" (2008) Drug Discov. Today, 13 (15-16): 695-701.
Sun et al., "Bowel necrosis induced by tumor necrosis factor in rats is mediated by platelet-activating factor" (1988) J. Clin. Invest., 81(5):1328-1331.
Suthanthiran et al., "Renal transplantation" (1994) New Engl. J. Med., 331(6):365-376.
Takashima et al., "Characterization of Mouse Sialyltransferase Genes: Their Evolution and Diversity" (2008) Biosci. Biotechnol. Biochem., 72(5):1155-1167.
Tang et al., *Conformational characterization of the charge variants of a human IgG1 monoclonal antibody using H/D exchange mass spectrometry*, mAbs, vol. 5, pp. 114-125 (2013).
Taylor et al. "A transgenic mouse that expresses a diversity of human sequence heavy and light chain immunoglobulins," Nucleic Acids Research,(1992) 20(23):6287-6295.
The Difference-Between, "Poly vs. Polyalcohol—What's the difference?" pp. 1-2, downloaded from http://the-difference-between.com/polyalcohol/polyol on Apr. 16, 2016.
Thiansilakul et al., *Compositions, functional properties and antioxidative activity of protein hydrolysates prepared from round scad (Decapterus maruadsi)*, Food Chemistry, 103:1385-1394 (2007).
Tian et al., *Spectroscopic evaluation of the stabilization of humanized monoclonal antibodies in amino acid formulations*, Int'l J. of Pharmaceutics, vol. 335, pp. 20-31 (2007).
To, et al., Hydrophobic interaction chromatography of proteins: I. The effects of protein and adsorbent properties on retention and recovery, J. of Chromatography A, 1141:191-205 (2007).
Tracey et al., "Shock and tissue injury induced by recombinant human cachectin" (1986) Science, 234(4775):470-474.
Tritsch et al., *Spontaneous decomposition of glutamine in cell culture media*, Experimental Cell Research, 28:360-364 (1962).
Tsubaki et al., *C-terminal modification of monoclonal antibody drugs: Amidated species as a general product0related substance*, Int'l J. Biological Macromolecules, vol. 52, pp. 139-147 (2013).
Tugcu et al., *Maximizing Productivity of Chromatography Steps for Purification of Monoclonal Antibodies*, vol. 99, No. 3, pp. 599-613 (available online Aug. 2007).
Urech, D.M. et al., Anti-inflammatory and cartilage-protecting effects of an intra-articularly injected anti-TNFa single-chain Fv antibody (ESBA105) designed for local therapeutic use, Ann Rheum Dis, 69, 443-449, Mar. 16, 2009.
Urlaub et al., "Isolation of Chinese hamster cell mutants deficient in dihydrofolate reductase activity" (1980) Proc. Natl. Acad. Sci. USA, 77:4216-4220.
Van der Heijde et al., Adalimumab effectively reduces the signs and symptoms of active ankylosing spondylitis in patients with total spinal ankylosis, Arthritis & Rheumatism 67:1218-1221 (2008).
Van der Heijde et al., Efficacy and Safety of Adalimumab in Patients with Ankylosing Spondylitis, Arthritis & Rheumatism 54:2136-46 (2006).
Van der Heijde et al., Efficacy and Safety of Infliximab in Patients with Ankylosing Spondylitis, Arthritis & Rheumatism 52:582-591 (2005).

(56) References Cited

OTHER PUBLICATIONS

Van Der Poll et al., "Activation of coagulation after administration of tumor necrosis factor to normal subjects" (1990) N. Engl. J. Med., 322(23):1622-1627.
Van Der Poll et al., "Comparison of the early dynamics of coagulation activation after injection of endotoxin and tumor necrosis factor in healthy humans" (1991) Prog. Clin. Biol. Res., 367:55-60.
Van Dulleman et al., "Treatment of Crohn's disease with anti-tumor necrosis factor chimeric monoclonal antibody (cA2)" (1995) Gastroenterology, 109(1):129-135.
Varki et al. Essentials of Glycobiology, 2nd edition, (1999) CSHL, Retrieved from the internet: ncbi.nlm.nih.gov/books/NBK1908/, 4 pages.
Wallick et al. "Glycosylation of a VH residue of a monoclonal antibody against alpha (1-6) dextran increases its affinity for antigen," J. Exp. Med.(1988) 168(3):1099-1109.
Walsh et al. "Effect of the carbohydrate moiety on the secondary structure of ?2-glycoprotein. I. Implications for the biosynthesis and folding of glycoproteins," Biochemistry. (1990) 29(26):6250-6257.
Wang et al., "The immobilized leukoagglutinin from the seeds of Maackia amurensis binds with high affinity to complex-type Asn-linked oligosaccharides containing terminal sialic acid-linked alpha-2,3 to penultimate galactose residues" (1988) J Biol. Chem., 263(10): 4576-4585.
Wang et al., Antibody Structure, Instability and Formulation, J. Pharm. Sci., vol. 96, No. 1, pp. 1-26 (2007).
Warnock et al., "In vitro galactosylation of human IgG at 1 kg scale using recombinant galactosyltransferase" (2005) Biotechnol. Bioeng., 92(7):831-842.
Wei et al., *Glyco-engineering of human IgG1-Fc through combined yeast expression and in vitro chemoenzymatic glycosylation*, National Institute of Health Public Access Author Manuscript, Biochemistry, 47(39):10294-10304 (2008).
Weikert et al., "Engineering Chinese hamster ovary cells to maximize sialic acid content of recombinant glycoproteins" (1999) Nature Biotechnology, 17(11): 1116-1121.
Weinstein et al., "Primary structure of beta-galactoside alpha 2,6-sialyltransferase. Conversion of membrane-bound enzyme to soluble forms by cleavage of the NH2-terminal signal anchor" (1987) J. Biol. Chem. 262(36):17735-17743.
Weitzhandler et al., *Protein variant separations by cation-exchange chromatography on tentacle-type polymeric stationary phases*, Proteomics, vol. 1, pp. 179-185 (2001).
Wong et al., *Impact of Dynamic Online Fed-Batch Strategies on Metabolism, Productivity and N-Glycosylation Quality in CHO Cell Cultures*, Biotechnol. Bioeng., 89(2):164-177 (2005).
Wyss, et al. "The structural role of sugars in glycoproteins," Curr. Opin. Biotechnol. (1996), 7(4); 409-416.
Xie et al., *High Cell Density and High Monoclonal Antibody Production Through Medium Design and Rational Control in a Bioreactor*, Biotechnol. Bioeng., 51:725-729 (1996).
Yang et al., *Effect of Ammonia on the Glycosylation of Human Recombinant Erythropoietin in Culture*, Biotech. Progress, 16:751-759 (2000).
Yao et al., "The potential etiologic role of tumor necrosis factor in mediating multiple organ dysfunction in rats following intestinal ischemia-reperfusion injury" (1995) Resuscitation, 29(2):157-168.
Zhang et al. "A novel function for selenium in biological system: Selenite as a highly effective iron carrier for Chinese hamster overary cell growth and monoclonal antibody production," Biotechnology and Bioengineering. (2006) 95(6):1188-1197.
Zhang et al., "CHO glycosylation mutants as potential host cells to produce therapeutic proteins with enhanced efficacy" (2013) Advances in Biochemical Engineering/Biotechnology, 131:63-87.
Zhang et al., *Mass Spectrometry For Structural Characterization of Therapeutic Antibodies*, Mass Spectrometry Reviews, 28:147-176 (2009).
Zhang, F. et al., "The Effect of Dissolved Oxygen (DO) Concentration on the Glycosylation of Recombinant Protein Produced by the Insect Cell-Baculovirus Expression System." *Biotechnology and Bioengineering*, (2002), 77(2);219-224.
Zhang, Y. et al., *Effects of peptone on hybridoma growth and monoclonal antibody formation*, Cytotechnology, 16:147-150 (1994).
Zhou, *Implementation of Advanced Technologies in Commercial MonoclonalAntibody Production*, Biotech. J., 3:1185-1200 (2008).
Zhu, *Mammalian cell protein expression for biopharmaceutical production*, Biotech.Adv., 30:1158-1170 (2012).

\* cited by examiner

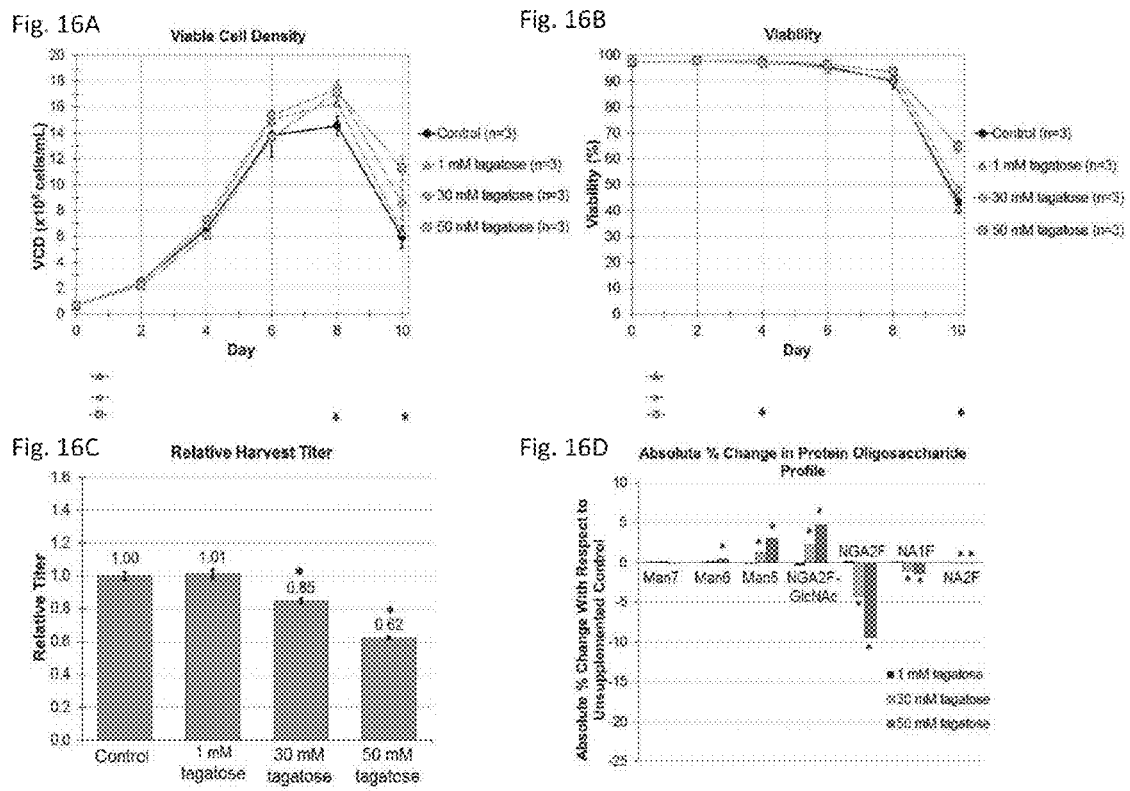

_US 9,499,614 B2_

METHODS FOR MODULATING PROTEIN GLYCOSYLATION PROFILES OF RECOMBINANT PROTEIN THERAPEUTICS USING MONOSACCHARIDES AND OLIGOSACCHARIDES

RELATED APPLICATIONS

This application claims priority to U.S. Provisional Patent Application Ser. No. 61/785,901, filed on Mar. 14, 2013, the entire contents of which are incorporated herein by reference.

BACKGROUND OF THE INVENTION

The instant invention relates to the field of protein (e.g., antibody or DVD-Ig) production, and, in particular, to methods and compositions for controlling and limiting the heterogeneity of proteins expressed in host cells. The production of proteins for biopharmaceutical applications typically involves the use of cell cultures that are known to produce proteins exhibiting varying levels of heterogeneity. The basis for such heterogeneity includes, but is not limited to, the presence of distinct glycosylation profiles in the produced proteins. For example, but not by way of limitation, such heterogeneity can be observed as an increase in high mannose N-glycans and NGA2F-GlcNAc species as well as a decrease in fucosylated species, such as NGA2F species.

The glycosylation profile of a protein (e.g., an antibody or DVD-Ig) can influence its biological activity through changes in half-life due to effects on clearance, folding, stability and antibody-dependent cellular cytotoxicity (ADCC) (Shental-Behor D. et al., (2008) PNAS 105:8256-8261; Kuhlmann M. et al., (2006) Nephrol. Dial. Transplant 21:v4-v8; Zheng K. et al., (2011) mAbs 3(6):568-576). ADCC is one mechanism responsible for the therapeutic effect of antibodies such as the anti-CD20 IgG1 rituximab and the anti-Her2/neu IgG1 trastuzumab. ADCC activity is influenced by the amount of fucose linked to the innermost GlcNAc of the Fc region, with enhanced activity seen with a reduction in fucose (Mori K. et al., (2007) Cytotechnology 55:109-114).

Heterogeneity of protein glycosylation can be assayed by releasing oligosaccharides present on the protein of interest (e.g., an antibody or DVD-Ig) via enzymatic digestion with, for example, N-glycanase. Once the glycans are released, the free reducing end of each glycan can be labeled by reductive amination with a fluorescent tag. The resulting labeled glycans are separated by normal-phase HPLC (NP-HPLC) and detected by a fluorescence detector for quantitation. Technological advances in recombinant protein production analysis have provided unique opportunities for identifying the extent of glycosylation exhibited by a particular protein population, particularly in the context of large-scale production of recombinant proteins.

Although such advances have allowed for the robust characterization of protein glycosylation, there remains a need in the art for culture conditions and production methods that allow for control over the glycosylation profile of a protein therapeutic. Modulation of protein glycosylation is particularly advantageous in the context of cell culture processes used for commercially produced recombinant bio-therapeutics as glycosylation has the potential to impact therapeutic utility. Control of the glycosylation profile of a therapeutic protein (e.g., an antibody or an antigen binding fragment thereof, or a DVD-Ig) is also critical for ensuring the production of comparable proteins such as biosimilars. Accordingly, there is a need in the art for compositions and methods for the targeted modulation of protein glycosylation. The instant invention addresses this need by providing compositions and methods for modulating protein glycosylation. The invention further provides methods for the targeted modulation of mannosylated and fucosylated N-glycan species linked to a protein of interest (e.g., antibody or DVD-Ig).

SUMMARY OF THE INVENTION

In one aspect, the present invention provides methods of producing a composition comprising a protein with a modulated glycosylation profile. The methods include culturing a host cell expressing the protein in cell culture media supplemented with a monosaccharide and/or an oligosaccharide, thereby producing the composition comprising the protein with a modulated glycosylation profile as compared to a control, wherein the control is a composition comprising the protein produced by culturing a host cell expressing the protein in the same cell culture media but which is not supplemented with a monosaccharide and/or an oligosaccharide.

In one embodiment, the methods further comprise purifying the composition comprising the protein with a modulated glycosylation profile.

In another embodiment, the protein is an antibody or antigen-binding portion thereof. In a particular embodiment, the antibody is an anti-TNFα antibody. In yet another embodiment the anti-TNFα antibody is adalimumab, or an antigen binding fragment thereof. In yet another embodiment, the protein is a dual variable domain immunoglobulin (DVD-Ig). In one embodiment, the protein is selected from the group consisting of a TVD-Ig, a half-body and a RAB.

In one embodiment of the invention, the monosaccharide is tagatose. In another embodiment, the oligosaccharide is sucrose.

In one embodiment, the cell culture media is supplemented with a sufficient amount of the monosaccharide, e.g., tagatose, to achieve a monosaccharide concentration selected from the group consisting of about 1 mM, 10 mM, 30 mM, 50 mM and 70 mM. In a particular embodiment, the monosaccharide, e.g., tagatose, concentration is 30 mM.

In one embodiment, the cell culture media is supplemented with a sufficient amount of the oligosaccharide, e.g., sucrose, to achieve an oligosaccharide concentration selected from the group consisting of about 1 mM, 7 mM, 10 mM, 15 mM, 30 mM, 50 mM and 70 mM. In a particular embodiment, the oligosaccharide, e.g., sucrose, concentration is 30 mM.

In another embodiment, the modulated glycosylation profile of the protein comprises modulation of a fucosylation level and/or a mannosylated N-glycan oligosaccharide level in the protein.

In another embodiment, the modulation of the fucosylation level comprises a decrease in the fucosylation level in the protein, e.g., a decrease in the level of NGA2F, NA1F-GlcNAc, NA1F and/or NA2F in the protein. In a further embodiment, the decrease in the level of NGA2F, NA1F-GlcNAc, NA1F and/or NA2F is a decrease of about 0.1%, 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60% or 65%.

In one embodiment, the modulation of the fucosylation level comprises an increase in the fucosylation level in the protein, e.g., an increase in the level of NGA2F-GlcNAc, NA1F-GlcNAc, NA1F and/or NA2F in the protein. In another embodiment, the increase in the level of NGA2F-GlcNAc, NA1F-GlcNAc, NA1F or NA2F is an increase of about 0.1%, 1%, 1.2%, 1.5%, 2%, 2.2%, 2.5%, 3%, 3.2%, 3.5%, 4%, 4.2%, 4.5%, 5%, 10%, 15% or 20%.

In one embodiment, an overall decrease in the fucosylation level comprises an increase or a decrease in the level of NGA2F, NGA2F-GlcNAc, NA1F-GlcNAc, NA1F and/or NA2F in the protein. In another embodiment, the decrease in the fucosylation level is a decrease of about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45% or 50%.

In another embodiment, the modulation of the mannosylated N-glycan level comprises an increase in the mannosylation level of the protein. In one embodiment, the mannosylation level is an increase of about 0.1%, 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45% or 50%. In yet another embodiment, the increase in the mannosylation level comprises an increase in the level of a high mannose N-glycan oligosaccharide selected from the group consisting of Man 5 glycan, Man 6 glycan, Man 7 glycan and Man 8 glycan. In one embodiment, the levels of Man 5 glycan, Man 6 glycan, Man 7 glycan and/or Man 8 glycan are increased by about 0.1%, 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40, 45% or 50%.

In one embodiment of the present invention the host cell is a CHO cell.

In another aspect, the present invention provides methods of producing compositions comprising an antibody, or antigen binding fragment thereof, with a modulated glycosylation profile. The methods include culturing a host cell expressing the antibody, or antigen binding fragment thereof, in cell culture media supplemented with sucrose and/or tagatose, thereby producing the composition comprising the antibody, or antigen binding fragment thereof, with an increased level of mannosylated N-glycans and a decreased level of fucosylated N-glycans as compared to a control, wherein the control is a composition comprising an antibody, or antigen binding fragment thereof, produced by culturing a host cell expressing the antibody, or antigen binding fragment thereof, in cell culture media which is not supplemented with tagatose and/or glucose. In one embodiment, the antibody is adalimumab, or an antigen binding fragment thereof.

In another aspect, the present invention provides methods of producing compositions comprising an antibody, or antigen binding fragment thereof, with a modulated glycosylation profile. The methods include culturing a host cell expressing the antibody, or antigen binding fragment thereof, in cell culture media supplemented with sucrose and/or tagatose, thereby producing the composition comprising the antibody, or antigen binding fragment thereof, with a 1-50% increase in the level of mannosylated N-glycans and a 1-50% decrease in the level of fucosylated N-glycans as compared to a control, wherein the control is a composition comprising an antibody, or antigen binding fragment thereof, produced by culturing a host cell expressing the antibody, or antigen binding fragment thereof, in cell culture media which is not supplemented with tagatose and/or glucose. In one embodiment, the antibody is adalimumab, or an antigen binding fragment thereof.

In a further aspect, the present invention provides compositions comprising a cell culture media comprising a monosaccharide and/or an oligosaccharide. In one embodiment, the monosaccharide is tagatose. In another embodiment, the oligosaccharide is sucrose.

In yet another aspect, the present invention provides pharmaceutical compositions comprising the protein compositions produced by the methods of the invention and a pharmaceutically acceptable carrier.

In another aspect, the present invention provides compositions comprising a therapeutic protein with a modulated glycosylation profile produced by the methods the invention. In one embodiment, the therapeutic protein is an antibody.

In another aspect, the present invention provides compositions comprising a therapeutic protein, wherein the protein comprises a 1-50% increase in the level of mannosylated N-glycans and a 1-50% decrease in the level of fucosylated N-glycans, as compared to the control, wherein the control is a composition comprising a protein produced by culturing a host cell expressing the protein in cell culture media which is not supplemented with a monosaccharide and/or an oligosaccharide, In one embodiment, the therapeutic protein is selected from the group consisting of an antibody, an antigen-binding portion thereof, DVD-Ig, TVD-Ig, RAB and half-body. In one embodiment, the therapeutic protein is an antibody.

In another aspect, the present invention provides methods of producing compositions comprising an antibody, or antigen binding fragment thereof, with a modulated glycosylation profile by culturing a host cell expressing the antibody, or antigen binding fragment thereof, in cell culture media supplemented with sucrose and/or tagatose, thereby producing the composition comprising the antibody, or antigen binding fragment thereof, with a 1-30% increase in antibody-dependent cellular cytotoxicity (ADCC) response as compared to a control, wherein the control is a composition comprising an antibody, or antigen binding fragment thereof, produced by culturing a host cell expressing the antibody, or antigen binding fragment thereof, in cell culture media which is not supplemented with tagatose and/or glucose. In one embodiment the antibody is adalimumab, or an antigen binding fragment thereof.

BRIEF DESCRIPTION OF THE DRAWINGS

FIG. 3A: Viable cell density. FIG. 3B: Percent viability. FIG. 3C: Harvest titer ratio. Control is unsupplemented media.

FIG. 5A: Viable cell density. FIG. 5B: Percent viability. FIG. 5C: Harvest titer ratio. Control is unsupplemented media.

FIG. 7A: Viable cell density.

FIG. 7B: pCO$_2$. FIG. 7C: Osmolality. FIG. 7D: Percent viability. FIG. 7E: Lactate. FIG. 7F: Harvest titer ratio. Control is unsupplemented media.

FIG. 9A: Viable cell density. FIG. 9B: pCO$_2$. FIG. 9C: Osmolality. FIG. 9D: Percent viability. FIG. 9E: Lactate. FIG. 9F: Harvest titer ratio. Control is unsupplemented media.

FIG. 11A: Viable cell density. FIG. 11B: Percent viability. FIG. 11C: Harvest titer ratio. Control is unsupplemented media.

FIG. 13A: Viable cell density. FIG. 13B: Percent viability. FIG. 13C: Relative harvest titer compared to unsupplemented control. FIG. 13D: Absolute % change in protein oligosaccharide profile compared to unsupplemented control. (*p<0.05 on marked day or process condition indicating a statistically significant difference compared to the unsupplemented control).

FIG. 14A: Viable cell density. FIG. 14B: Percent viability. FIG. 14C: Relative harvest titer compared to unsupplemented control. FIG. 14D: Absolute % change in protein oligosaccharide profile compared to unsupplemented control. (*p<0.05 on marked day or process condition indicating a statistically significant difference compared to the unsupplemented control).

FIG. 15A: Viable cell density. FIG. 15B: Percent viability. FIG. 15C: Relative harvest titer compared to unsupplemented control. FIG. 15D: Absolute % change in protein oligosaccharide profile compared to unsupplemented control. (*p<0.05 on marked day or process condition indicating a statistically significant difference compared to the unsupplemented control).

FIGS. 16A-16D depict the cell culture performance of Cell Line 2 in media supplemented with 1 mM, 30 mM, or 50 mM tagatose. FIG. 16A: Viable cell density. FIG. 16B: Percent viability. FIG. 16C: Relative harvest titer compared to unsupplemented control. FIG. 16D: Absolute % change in protein oligosaccharide profile compared to unsupplemented control. (*p<0.05 on marked day or process condition indicating a statistically significant difference compared to the unsupplemented control).

FIG. 17A: Viable cell density. FIG. 17B: Percent viability. FIG. 17C: Glucose concentration. FIG. 17D: Lactate concentration. FIG. 17E: Osmolality. FIG. 17F: Relative harvest titer compared to unsupplemented control.

DETAILED DESCRIPTION OF THE INVENTION

Figure 1:
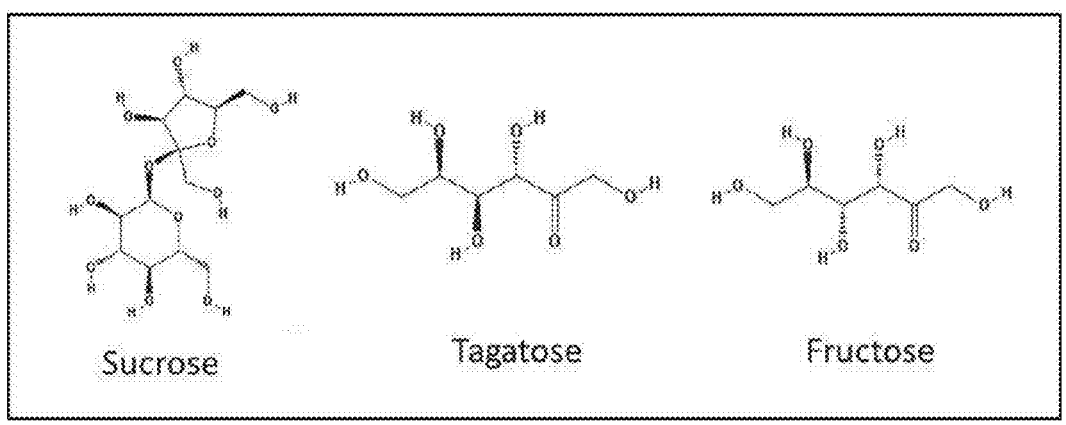
FIG. 1 depicts the chemical structure of sucrose, tagatose and fructose.

The present invention provides methods and compositions for modulating the glycosylation profile of a protein such as a therapeutic protein (e.g., antibody, DVD-Ig, TVD-Ig, Half-body or RAB compositions).

The present invention is based on the identification and optimization of upstream process technologies, e.g., recombinant cell culture conditions, for protein production, e.g., production of antibodies or antigen-binding portions thereof or DVD-Igs, resulting in the production of protein compositions with modulated glycosylation profiles (e.g., decreased fucosylation and/or increased mannosylation).

I. Definitions

In order that the present invention may be more readily understood, certain term are first defined.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms, for example, those characterized by "a" or "an", shall include pluralities, e.g., one or more impurities. In this application, the use of "or" means "and/or", unless stated otherwise. Furthermore, the use of the term "including," as well as other forms of the term, such as "includes" and "included", is not limiting. Also, terms such as "element" or "component" encompass both elements and components comprising one unit and elements and components that comprise more than one unit unless specifically stated otherwise.

Most naturally occurring peptides (or proteins) comprise carbohydrate or saccharide moieties attached to the peptide via specific linkages to a select number of amino acids along the length of the primary peptide chain. Thus, many naturally occurring peptides are termed "glycopeptides" or "glycoproteins" or are referred to as "glycosylated" proteins or peptides.

The term "glycoform" refers an isoform of a protein, e.g., an antibody, that differs only with respect to the number and/or type of attached glycan(s). Glycoproteins often consist of a number of different glycoforms.

The predominant sugars found on glycoproteins are glucose, galactose, mannose, fucose, N-acetylgalactosamine ("GalNAc"), N-acetylglucosamine ("GlcNAc") and sialic acid (e.g., N-acetylneuraminic acid ("NANA" or "NeuAc", where "Neu" is neuraminic acid) and "Ac" refers to "acetyl"). The processing of the sugar groups occurs co-translationally in the lumen of the ER and continues in the Golgi apparatus for N-linked glycoproteins.

The oligosaccharide structure attached to the peptide chain is known as a "glycan" molecule. The glycan structures found in naturally occurring glycopeptides are typically divided into two classes, "N-linked glycans" or N-linked oligosaccharides" and "O-linked glycans" or O-linked oligosaccharides".

Peptides expressed in eukaryotic cells typically comprise N-glycans. "N-glycans" are N-glycosylated at an amide nitrogen of an asparagine or an arginine residue in a protein via an N-acetylglucosamine residue. These "N-linked glycosylation sites" occur in the peptide primary structure containing, for example, the amino acid sequence asparagine-X-serine/threonine, where X is any amino acid residue except proline and aspartic acid.

Techniques for the determination of glycan primary structure are well known in the art and are described in detail, for example, in Montreuil, "Structure and Biosynthesis of Glycopeptides" In *Polysaccharides in Medicinal Applications*, pp. 273-327, 1996, Eds. Severian Damitriu, Marcel Dekker, NY. It is therefore a routine matter for one of ordinary skill in the art to isolate a population of peptides produced by a cell and determine the structure(s) of the glycans attached thereto. For example, efficient methods are available for (i) the splitting of glycosidic bonds either by chemical cleavage such as hydrolysis, acetolysis, hydrazinolysis, or by nitrous deamination; (ii) complete methylation followed by hydrolysis or methanolysis and by gas-liquid chromatography and mass spectroscopy of the partially methylated monosaccharides; and (iii) the definition of anomeric linkages between monosaccharides using exoglycosidases, which also provide insight into the primary glycan structure by sequential degradation. Fluorescent labeling and subsequent high performance liquid chromatography (HPLC), e.g., normal phase HPLC (NP-HPLC), mass spectroscopy and nuclear magnetic resonance (NMR) spectrometry, e.g., high field NMR, may also be used to determine glycan primary structure.

Kits and equipment for carbohydrate analysis are also commercially available. Fluorophore Assisted Carbohydrate Electrophoresis (FACE) is available from Glyko, Inc. (Novato, Calif.). In FACE analysis, glycoconjugates are released from the peptide with either Endo H or N-glycanase (PNGase F) for N-linked glycans, or hydrazine for Ser/Thr linked glycans. The glycan is then labeled at the reducing end with a fluorophore in a non-structure discriminating manner. The fluorophore labeled glycans are then separated in polyacrylamide gels based on the charge/mass ratio of the saccharide as well as the hydrodynamic volume. Images are taken of the gel under UV light and the composition of the glycans is determined by the migration distance as compared with the standards. Oligosaccharides can be sequenced in this manner by analyzing migration shifts due to the sequential removal of saccharides by exoglycosidase digestion.

All N-linked oligosaccharides have a common "pentasaccharide core" of $Man_3GlcNAc_2$. ("Man" refers to mannose; "Glc" refers to glucose; "NAc" refers to N-acetyl; and "GlcNAc" refers to N-acetylglucosamine). The pentasaccharide core is also referred to as the "trimannose core" or the "paucimannose core".

N-glycans differ with respect to the presence of, and/or in the number of branches (also called "antennae") comprising peripheral sugars such as N-acetylglucosamine, galactose, N-acetylgalactosamine, N-acetylneuraminic acid, fucose and sialic acid that are added to the $Man_3GlcNAc_2$ core structure. Optionally, this structure may also contain a core fucose molecule and/or a xylose molecule. For a review of standard glycobiology nomenclature see, *Essentials of Glycobiology* Varki et al. eds., 1999, CSHL Press, the contents of which are incorporated herein by reference.

N-glycans are classified according to their branched constituents (e.g., oligomannose-type, complex, or hybrid). An "oligomannose-type" or "high mannose-type" N-glycan has five or more mannose residues.

A "complex-type" N-glycan typically has at least one GlcNAc attached to the 1,3 mannose arm and at least one GlcNAc attached to the 1,6 mannose arm of a pentasaccharide core. Complex-type N-glycans may also have galactose ("Gal") or N-acetylgalactosamine residues that are optionally modified with sialic acid or derivatives, e.g., N-acetyl neuraminic acid. Complex-type N-glycans may also have intrachain substitutions comprising "bisecting" GlcNAc, and core fucose ("Fuc"). Complex N-glycans may also have multiple antennae on the pentasaccharide core and are, therefore, also referred to as "multiple antennary-type glycans."

A "hybrid-type" N-glycan comprises at least one GlcNAc on the terminal of the 1,3 mannose arm of the pentasaccharide core and zero or more mannoses on the 1,6 mannose arm of the trimannose core.

The oligomannose-type structures that may be present within the compositions of the invention and/or may be used in the methods of the invention are referred to herein as "M5" or "Man 5 glycan"; "M6" or "Man 6 glycan"; "M7" or "Man 7 glycan"; "M8" or "Man 8 glycan"; and "M9" or "Man 9 glycan."

In one embodiment, an M5 oligomannose-type structure has the structure (I):

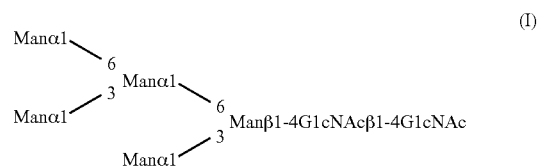

In one embodiment, an M6 oligomannose-type structure has the structure (II):

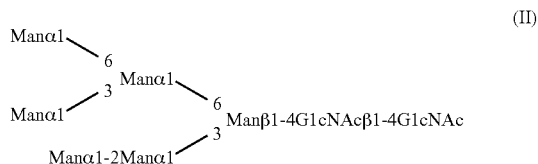

In one embodiment, an M7 oligomannose-type structure has the structure (III):

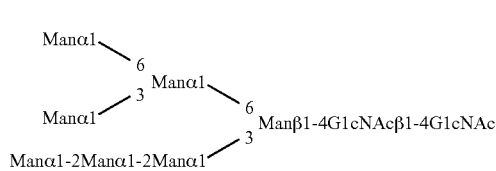

(III)

In another embodiment, an M7 oligomannose-type structure has the structure (IV):

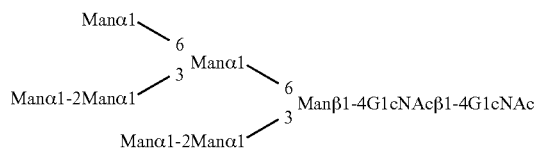

(IV)

In another embodiment, an M7 oligomannose-type structure has the structure (V):

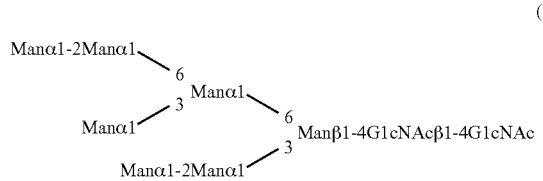

(V)

In one embodiment, an M8 oligomannose-type structure has the structure (VI):

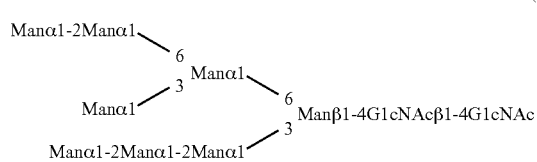

(VI)

In another embodiment, an M8 oligomannose-type structure has the structure (VII):

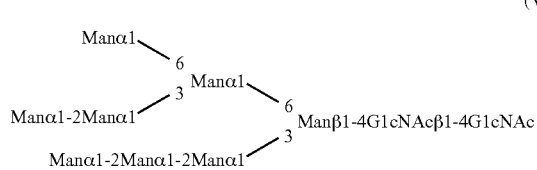

(VII)

In another embodiment, an M8 oligomannose-type structure has the structure (VIII):

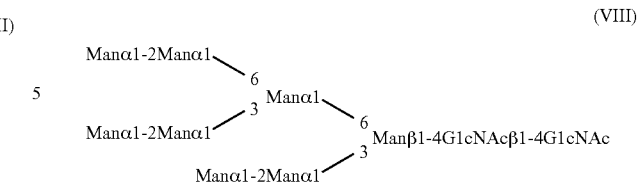

(VIII)

In one embodiment, an M9 oligomannose-type structure has the structure (IX):

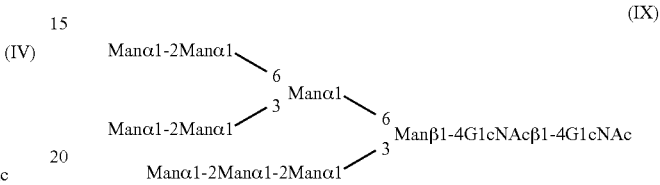

(IX)

In one embodiment, the oligomannose-type structures that may be present within the compositions of the invention and/or may be used in the methods of the invention are independently selected from the group consisting of Man 5 glycan, Man 6 glycan, Man 7 glycan, Man 8 glycan, and/or Man 9 glycan.

In one embodiment, a multiple antennary-type structure that may be present within the compositions of the invention and/or may be used in the methods of the invention is a "bianntennary oligosaccharide-type structure". A "bianntennary oligosaccharide-type structure" is an N-linked glycan having two branches or arms, and a core fucose with zero, one or two galactose additions on the arms. In one embodiment, a "bianntennary oligosaccharide-type structure" that may be present within the compositions of the invention and/or may be used in the methods of the invention is bisected. In one embodiment, a "bianntennary oligosaccharide-type structure" that may be present within the compositions of the invention and/or may be used in the methods of the invention is a "fucosylated bianntennary oligosaccharide-type structure", e.g., comprises a core-substituted with fucose.

In one embodiment, a "fucosylated bianntennary oligosaccharide-type structure" that may be present within the compositions of the invention and/or may be used in the methods of the invention is an "asialo, fucosylated bianntennary oligosaccharide-type structure", also referred to as an "asialo, bigalactosylated biantennary, core-substituted with fucose", referred to herein as "NA2F."

In another embodiment, a "fucosylated bianntennary oligosaccharide-type structure" that may be present within the compositions of the invention and/or may be used in the methods of the invention is a asialo, agalacto, fucosylated biantennary oligosaccharide-type structure, also referred to as an asialo, agalacto-, biantennary, core-substituted with fucose, referred to herein as "NGA2F."

In another embodiment, a "fucosylated bianntennary oligosaccharide-type structure" that may be present within the compositions of the invention and/or may be used in the methods of the invention is a asialo, fucosylated bianntennary oligosaccharide-type structure, also referred to as asialo, monogalactosylated biantennary, core-substituted with fucose, referred to herein as "NA1F."

In another embodiment, a "fucosylated bianntennary oligosaccharide-type structure" that may be present within the compositions of the invention and/or may be used in the methods of the invention is a asialo, agalacto, fucosylated biantennary, minus a bisecting N-acetylglucosamine oligosaccharide-type structure, also referred to as asialo, agalacto-, biantennary, core-substituted with fucose minus a bisecting N-acetylglucosamine, referred to herein as "NGA2F-GlcNAc."

In yet another embodiment, a "fucosylated bianntennary oligosaccharide-type structure" that may be present within the compositions of the invention and/or may be used in the methods of the invention is a asialo, monogalacto, fucosylated biantennary, minus a bisecting N-acetylglucosamine oligosaccharide-type structure, also referred to as asialo, monogalactosylated biantennary, core-substituted with fucose minus a bisecting N-acetylglucosamine, referred to herein as "NA1F-GlcNAc."

In one embodiment, an NA2F fucosylated biantennary oligosaccharide-type structure has the structure (X):

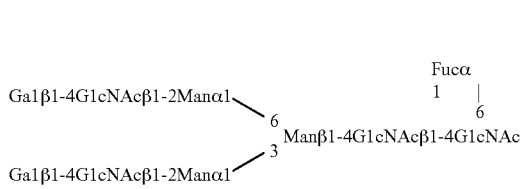

(X)

In one embodiment, an NGA2F fucosylated biantennary oligosaccharide-type structure has the structure (XI):

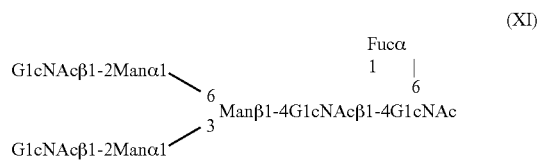

(XI)

In one embodiment, an NA1F fucosylated biantennary oligosaccharide-type structure has the structure (XII):

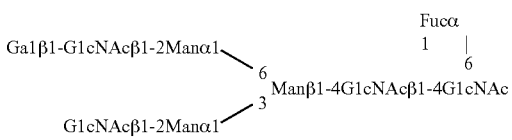

(XII)

In another embodiment, an NA1F fucosylated biantennary oligosaccharide-type structure has the structure (XIII):

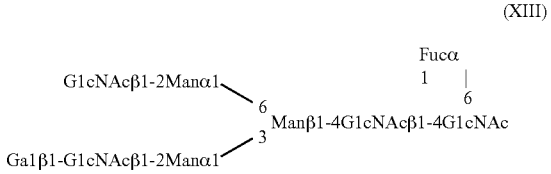

(XIII)

In one embodiment, an NGA2F-GlcNAc, and NA1F-GlcNAc fucosylated biantennary oligosaccharide-type structure has the structure (XIV):

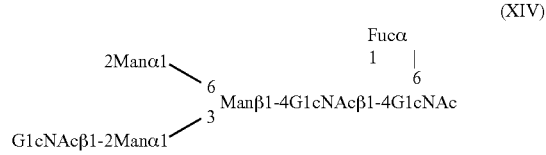

(XIV)

In one embodiment, an NA1F-GlcNAc fucosylated biantennary oligosaccharide-type structure has the structure (XV):

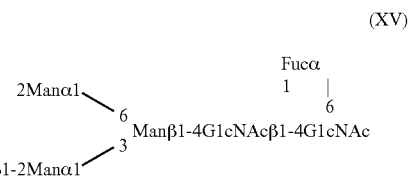

(XV)

In one embodiment, the fucosylated biantennary oligosaccharide-type structure is independently selected from the group consisting of NGA2F, NA1F, NA2F, NGA2F-GlcNAc, and NA1F-GlcNAc.

As used herein, a "modulated glycosylation profile" includes a profile of a composition comprising a protein (e.g., an antibody or DVD-Ig) which is modulated as compared to the glycosylation profile of a composition comprising that same protein produced by culturing a host cell expressing that protein in cell culture media which is not supplemented with a monosaccharide (e.g., tagatose) and/or an oligosaccharide (e.g., sucrose). The modulated glycosylation profile may include an overall increase in the level of mannosylated N-glycans and an overall decrease in the level of fucosylated N-glycans in the protein. For example, the overall level of mannosylated N-glycans in the protein may be increased by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 1-99% are contemplated by the invention.

In another example, the overall level of mannosylated N-glycans comprises an increase in the amount or level of a high mannose N-glycan oligosaccharide. A high-mannose N-glycan has more than one mannose linked to the non-reducing terminal of the core structure. For example, the high mannose N-glycan oligosaccharide is selected from the group consisting of Man 5 glycan, Man 6 glycan, Man 7 glycan and Man 8 glycan. In one embodiment, the amount or level of at least one of Man 5 glycan, Man 6 glycan, Man 7 glycan and/or Man 8 glycan is increased by about 0.1%, 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., 0.1-5%, 0.1-10%, 0.1-15%, 0.1-20%, 0.1-21%, 0.1-22%, 0.1-23%, 0.1-24%, 0.1-25%, 0.1-26%, 0.1-27%, 0.1-28%, 0.1-29%, 0.1-30%, 0.1-35%, 0.1-40%, 0.1-41%, 0.1-42%, 0.1-43%, 0.1-44%, 0.1-45%, 0.1-46%, 0.1-47%, 0.1-48%, 0.1-49%, 0.1-50%, 1-5%, 1-10%, 1-15%, 1-20%, 1-21%, 1-22%, 1-23%, 1-24%, 1-25%, 1-26%, 1-27%, 1-28%, 1-29%, 1-30%, 1-35%, 1-40%, 1-41%, 1-42%, 1-43%, 1-44%, 1-45%, 1-46%, 1-47%, 1-48%, 1-49%, 1-50%, 2-5%, 2-10%, 2-15%, 2-20%, 2-21%, 2-22%, 2-23%, 2-24%, 2-25%, 2-26%, 2-27%, 2-28%, 2-29%, 2-30%, 2-35%, 2-40%, 2-41%, 2-42%, 2-43%, 2-44%, 2-45%, 2-46%, 2-47%, 2-48%, 2-49%, 2-50%, 3-5%, 3-10%, 3-15%, 3-20%, 3-21%, 3-22%, 3-24%, 3-25%, 3-26%, 3-27%, 3-28%, 2-29%, 3-30%, 3-35%, 3-40%, 3-41%, 3-42%, 3-43%, 3-44%, 3-45%, 3-46%, 3-47%, 3-48%, 3-49%, 3-50%, 4-5%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 0.1-99% are contemplated by the invention.

In another example, an overall decrease in the level of fucosylated N-glycans resulting from modulation of any one of the fucosylated glycan species such as NGA2F-GlcNAc, NGA2F, NA1F-GlcNAc, NA1F and/or NA2F is decreased by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50%, 5-10%, 5-15%, 5-20%, 5-25%, 5-30%, 5-35%, 5-40%, 5-41%, 5-42%, 5-43, 5-44%, 5-45%, 5-46%, 5-47%, 5-48%, 5-49%, 5-50% or 1-99% are contemplated by the invention.

The term "level" with respect to protein such as an antibody, or antigen-binding fragment thereof, which is glycosylated at an N-linked glycosylation site on the Fc region in a composition refers to the relation of one glycoform in a composition to the whole of the glycoform levels in the composition and is expressed as a percentage of the whole, e.g., 0-100%. The level in a composition may be an absolute amount as measured in molecules, moles, or weight percent.

Compositions comprising varying levels of glycoforms of a protein such as a human antibody, or antigen-binding fragment thereof, are useful in that by varying the glycoform compositions a desired characteristics, e.g., rate of serum clearance or ADCC activity, may be achieved.

The methods of the invention can be used to produce compositions of any protein, such as a therapeutic protein, e.g., an antibody, an antigen-binding portion thereof, a DVD-Ig, a TVD-Ig, a RAB or a half-body.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., in the case of Adalimumab, hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VB regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding fragments are complete domains or pairs of complete domains.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may bind TNFα molecules from other species. Moreover, an isolated antibody may be substantially free of other cellular material and/or chemicals. A suitable anti-TNFα antibody is adalimumab.

As used herein, the term "adalimumab," also known by its trade name HUMIRA®(AbbVie) refers to a human IgG$_1$ antibody that binds human tumor necrosis factor α (TNFα). In general, the heavy chain constant domain 2 (CH2) of the adalimumab IgG-Fc region is glycosylated through covalent attachment of oligosaccharide at asparagine 297 (Asn-297). The light chain variable region of adalimumab is provided herein as SEQ ID NO:1, and the heavy chain variable region of adalimumab is provided herein as SEQ ID NO:2. Adalimumab comprises a light chain variable region comprising a CDR1 of SEQ ID NO:7, a CDR2 of SEQ ID NO:5, and a CDR3 of SEQ ID NO:3. Adalimumab comprises a heavy chain variable region comprising a CDR1 of SEQ ID NO:8, a CDR2 of SEQ ID NO:6 and CDR3 of SEQ ID NO:4. The nucleic acid sequence of the light chain variable region is set forth in SEQ ID NO:9. The nucleic acid sequence of the heavy chain variable region is set forth in SEQ ID NO:10. The full length amino acid sequence of the light chain is set forth as SEQ ID NO:11 and the full length amino acid sequence of the heavy chain is set forth as SEQ ID NO:12. Adalimumab is described in U.S. Pat. Nos. 6,090,382; 6,258,562; 6,509,015; 7,223,394; 7,541,031; 7,588,761; 7,863,426; 7,919,264; 8,197,813; 8,206,714; 8,216,583; 8,420,081; 8,092,998; 8,093,045; 8,187,836; 8,372,400; 8,034,906; 8,436,149; 8,231,876; 8,414,894; 8,372,401, the entire contents of each which are expressly incorporated herein by reference in their entireties. Adalimumab is also described in the "Highlights of Prescribing Information" for HUMIRA® (adalimumab) Injection (Revised January 2008) the contents of which are hereby incorporated herein by reference.

As used herein, a heavy chain antigen binding domain (referred to herein as VD or VDH) is intended to include a heavy chain variable domain, a dual heavy chain variable domain, a triple heavy chain variable domain, a light chain variable domain, a dual light chain variable domain, a triple light chain variable domain, a heavy chain variable domain in combination with a light chain variable domain, two heavy chain variable domains in combination with a light chain variable domain, a heavy chain variable domain in combination with two light chain variable domains, a domain antibody, a camelid antibody, a scFv, a receptor, and a scaffold antigen binding protein. It is understood that the heavy chain antigen binding domain may or may not bind an antigen independently of a paired light chain, dual light chain, or triple light chain, as appropriate, present on a second polypeptide of the binding proteins of the invention. For example, a domain antibody, a scFv, or a receptor would be expected to bind a target independent of any amino acid sequences on a second polypeptide claim. As the binding proteins of the invention form functional antigen binding sites, if the heavy chain antigen binding domain cannot specifically bind a target antigen independently (i.e., does not alone provide a functional antibody binding site), a second polypeptide should be present to provide a complementary light chain variable domain to provide a functional antibody binding site.

As used herein, a light chain antigen binding domain (referred to herein as VD or VDL) is intended to include a light chain variable domain, a dual light chain variable domain, a triple light chain variable domain, a heavy chain variable domain, a dual heavy chain variable domain, a triple heavy chain variable domain, a heavy chain variable domain in combination with a light chain variable domain, two heavy chain variable domains in combination with a light chain variable domain, a heavy chain variable domain in combination with two light chain variable domains, a camelid antibody, a domain antibody, a camelid antibody, a scFv, a receptor, and a scaffold antigen binding protein. It is understood that the light chain antigen binding domain may or may not bind an antigen independently of a paired heavy chain, dual heavy chain, or triple heavy chain, as appropriate, present on another polypeptide of the binding proteins of the invention. For example, a domain antibody, a scFv, or a receptor would be expected to bind a target independent of any amino acid sequences on a second polypeptide claim.

As used herein, "VD" alone can be understood to be either a heavy chain antigen binding domain or a light chain antigen binding domain unless otherwise clear from context.

Figure 19:
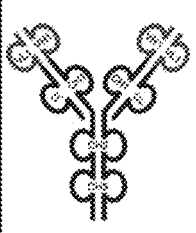
FIG. 19 is a schematic representation of various protein therapeutics (e.g., antibody, DVD-Ig, TVD-Ig, RAB, Half-body) whose glycosylation profiles may be modulated using the methods of the present invention.

As used herein, "Dual Variable Domain Immunoglobulin" or "DVD-Ig™" and the like are understood to include binding proteins having the structure schematically represented in FIG. 19 and provided in US Patent Publications 20100260668 and 20090304693 both of which are incorporated herein by reference. DVDs may be monospecific, i.e., bind one antigen, or multispecific, i.e. bind two or more antigens. A DVD-Ig™ comprises a paired heavy chain DVD polypeptide and a light chain DVD polypeptide with each paired heavy and light chain providing two antigen binding sites. Each binding site includes a total of 6 CDRs involved in antigen binding per antigen binding site. A DVD-Ig™ is typically has two arms bound to each other at least in part by dimerization of the CH3 domains, with each arm of the DVD being bispecific, providing an immunoglobulin with four binding sites.

A TVD-Ig is described in PCT Publication No. WO 2012/088290, the entire contents of which are incorporated herein by reference. A half-body is described in PCT Publication No. WO 2012/088302, the entire contents of which are incorporated herein by reference.

As used herein, the term "upstream process technology," in the context of protein, e.g., antibody, preparation, refers to activities involving the production and collection of proteins (e.g. antibodies or DVD-Igs) from cells (e.g., during cell culture of a protein with a modulated glycosylation profile). As used herein, the term "cell culture" refers to methods and techniques employed to generate and maintain a population of host cells capable of producing a recombinant protein with a modulated glycosylation profile, as well as the methods and techniques for optimizing the production and collection of the protein with a modulated glycosylation profile. For example, once an expression vector has been incorporated into an appropriate host, the host can be maintained under conditions suitable for high level expression of the relevant nucleotide coding sequences, and the collection and purification of the desired recombinant protein.

When using the cell culture techniques of the instant invention, the protein with a modulated glycosylation profile can be produced intracellularly, in the periplasmic space, or directly secreted into the medium. In embodiments where the protein with a modulated glycosylation profile is produced intracellularly, the particulate debris, either host cells or lysed cells (e.g., resulting from homogenization), can be removed by a variety of means, including but not limited to, by centrifugation or ultrafiltration. Where the protein with a modulated glycosylation profile is secreted into the medium, supernatants from such expression systems can be first concentrated using a commercially available protein concentration filter, e.g., an Amicon™ or Millipore Pellicon™ ultrafiltration unit As used herein, the term "downstream process technology" refers to one or more techniques used after the upstream process technologies to purify the protein, e.g., antibody, antigen-binding portion thereof, or DVD-Ig, of interest. For example, downstream process technology includes purification of the protein product, using, for example, affinity chromatography, including Protein A affinity chromatography, ion exchange chromatography, such as anion or cation exchange chromatography, hydrophobic interaction chromatography, displacement chromatography, multi-mode chromatography, continuous and recycle chromatography, viral filtration, depth filtration, ultrafiltration, diafiltration and centrifugation.

As used herein a "recombinant expression vector" can be any suitable recombinant expression vector, and can be used to transform or transfect any suitable host. For example, one of ordinary skill in the art would appreciate that transformation or transfection is a process by which exogenous nucleic acid such as DNA is introduced into a cell wherein the transformation or transfection process involves contacting the cell with the exogenous nucleic acid such as the recombinant expression vector as described herein. Non-limiting examples of such expression vectors are the pUC series of vectors (Fermentas Life Sciences), the pBluescript series of vectors (Stratagene, LaJolla, Calif.), the pET series of vectors (Novagen, Madison, Wis.), the pGEX series of vectors (Pharmacia Biotech, Uppsala, Sweden), and the pEX series vectors (Clontech, Palo Alto, Calif.).

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the Kingdoms of life. In another embodiment, eukaryotic cells include protist, fungal, plant and animal cells. In another embodiment, host cells include, but are not limited to, the prokaryotic cell line *E. coli*; mammalian cell lines CHO, HEK 293, COS, NS0, SP2 and PER.C6; the insect cell line Sf9; and the fungal cell *Saccharomyces cerevisiae*.

In certain embodiments, the host cells used in the methods of the present invention are prokaryote, yeast, or higher eukaryote cells. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In certain embodiments, the host cells are eukaryotic microbes such as filamentous fungi or yeast. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotoler-*

*ans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

In certain embodiments the host cells are derived from multicellular organisms. In particular embodiments, the cells are invertebrate cells from plant and insect cells. Non-limiting examples include cells derived from *Spodoptera frugiperda* (caterpillar), *Aedes aegypti* (mosquito), *Aedes albopictus* (mosquito), *Drosophila melanogaster* (fruitfly), *Bombyx mori*, cotton, corn, potato, soybean, petunia, tomato, and tobacco can also be utilized. As used herein, the term "recombinant protein" refers to a protein produced as the result of the transcription and translation of a gene carried on a recombinant expression vector that has been introduced into a host cell. In certain embodiments the recombinant protein is an antibody, preferably a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., an Fc fragment or a Fab fragment). In some embodiments, the recombinant protein is a DVD-Ig, a TVD-Ig, a RAB or a half-body.

In the methods of the invention, the host cells are cultured in media supplemented with an oligosaccharide and/or a monosaccharide. As used herein, the term "monosaccharide" refers to any of a class of carbohydrates that cannot be broken down to simpler sugars by hydrolysis and that constitute the building blocks of oligosaccharides and polysaccharides. Monosaccharides consist of at least three carbon atoms, one of which is attached to an oxygen atom to form an aldehyde group (CHO) or a ketone, and the others of which are each attached to a hydroxyl group (OH). A monosaccharide comprising three carbons per molecule is referred to a triose. A monosaccharide comprising four carbons per molecule is referred to as a tetrose. A monosaccharide comprising five carbons per molecule is referred to as a pentose. A monosaccharide sugar containing six carbons per molecule is referred to as a hexose. Monosaccharides can occur as chains or rings. Non-limiting examples of monosaccharides include tagatose, glucose, galactose, ribose, fructose and xylose. In one embodiment of the invention, the monosaccharide is not glucose.

As used herein the term "oligosaccharide" refers to a saccharide polymer containing a small number of, generally two to ten, monosaccharides. The monosaccharide units are bonded to each other by glycosidic linkages. Non-limiting examples of oligosaccharides include sucrose, lactose, maltose, raffinose, trehalose, melibiose, maltotriose, gentianose and maltopentalose.

The term "about", as used herein, is intended to refer to ranges of approximately 0.1-2.0% greater than or less than the referenced value. In certain circumstances, one of skill in the art will recognize that, due to the nature of the referenced value, the term "about" can mean more or less than a 0.1-2.0% deviation from that value.

The term "control", as used herein, is intended to refer to a composition comprising a protein produced by culturing a host cell expressing a protein in cell culture media which is not supplemented with a monosaccharide and/or an oligosaccharide. For example, a control may include a composition comprising a protein (e.g., an antibody) produced using the same host cell line and the same recombinant expression vector under the same cell culture conditions, including the same culture media, same culture vessel, same culture mode, same culture temperature and same pH, but without monosaccharide or oligosaccharide supplementation. For example, if antibody X is the antibody whose glycosylation profile is modulated using the methods of the invention, the control would be a composition comprising antibody X produced using the same host cell line and the same recombinant expression vector under the same cell culture conditions, including the same culture media, same culture vessel, same culture mode, same culture temperature and same pH, but without monosaccharide or oligosaccharide supplementation.

II. Modulation of Protein Glycosylation Using Monosaccharides and Oligosaccharides Glycosylation It is well known that the pattern of glycoforms that arise in recombinant proteins, including monoclonal antibodies, can be affected by culture conditions during production (Nam et al. (2008) Biotechnol. Bioeng. 100(6): 1178-92). Consistency in the quality of the glycoproteins is important as glycosylation may impact protein solubility, activity, and circulatory half-life. (Gawlitzek et al. (1995) Biotechnol. Bioeng. 46:536-544; and Hayter et al. (1992) Biotechnol. Bioeng. 39:327-335).

Post-translational modification of nascent recombinant proteins includes enzymatic glycosylation. The resulting proteins, bearing covalently linked oligosaccharide side chains, are known as glycosylated proteins or glycoproteins. Antibodies are glycoproteins with one or more carbohydrate residues in the Fc domain, as well as the variable domain. Carbohydrate residues in the Fc domain have an important effect on the effector function of the Fc domain, with minimal effect on antigen binding or half-life of the antibody (Jefferis, R. Biotechnol. Prog. (2005) 21:11-16). In contrast, glycosylation of the variable domain may have an effect on the antigen binding activity of the antibody. Glycosylation in the variable domain may also have a negative effect on antibody binding affinity, likely due to steric hindrance (Co, M. S. et al., (1993) Mol. Immunol. 30:1361-1367), or result in increased affinity for the antigen (Wallick, S. C. et al., (1988) Exp. Med. 168:1099-1109; Wright, A. et al., (1991) EMBO J. 10:2717 2723).

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the proteins produced using the methods of the present invention may include, but are not limited to, glucose, galactose, mannose, fucose, n-acetylglucosamine, NGA2F-GlcNAc, NGA2F, NA1F-GlcNAc, NA1F, NA2F and sialic acid.

In one aspect of the present invention, the glycosylation of a protein, e.g., antibody, antigen-binding portion thereof, or DVD-Ig, is modulated. Glycosylation can be modulated to, for example, increase the affinity of the antibody or antigen-binding portion for the antigen. Such carbohydrate modifications can be accomplished by, for example, altering upstream process technologies, for example, recombinant host cell culture conditions by supplementing the cell culture media with an oligosaccharide (e.g., sucrose) and/or a monosaccharide (e.g., tagatose).

Additionally or alternatively, the present invention provides methods for modulating the glycosylation profile of a protein (e.g., an antibody or DVD-Ig), such as modulating the type of glycan species and/or the amount or level of glycan species present in the protein. For example, the methods of the present invention can be used to produce a hypofucosylated antibody having decreased amounts or levels of fucosyl residues. Such altered glycosylation patterns have been demonstrated to increase the ADCC ability of antibodies. In one embodiment, the amount of NGA2F species linked to the protein is decreased, for example, the amount or level of NGA2F species linked to the protein is decreased by about 0.1%, 1%, 1.2%, 1.5%, 2%, 2.2%, 2.5%, 3%, 3.2%, 3.5%, 4%, 4.2%, 4.5%, 5%, 6%, 7%, 8%, 9%, 10%, 15%, 20%, 25%, 30%, 35%, 40%, 45%, 50%, 51%, 52%, 53%, 54%, 55%, 60%, 65%, 70%, 75%, 80%, 85%, 90%, 95%, or 99%. Ranges within one or more of the preceding values, e.g., about 0.1% to 50%, 1% to 50%, 1% to 51%, 1% to 55%, 1% to 60%, 5% to 50%, 5% to 51%, 5% to 55%, 5% to 60%, 9% to 51%, 10% to 60%, or 0.1% to 99% are contemplated by the invention.

In another embodiment, the modulation of the glycosylation of the protein results in an increase in the amount or level of NGA2F-GlcNAc species linked to the protein, for example, the amount or level of NGA2F-GlcNAc species linked to the protein is increased by about 0.1%, 1%, 1.2%, 1.5%, 2%, 2.2%, 2.5%, 3%, 3.2%, 3.5%, 4%, 4.2%, 4.5%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 0.1% to 5%, 0.1% to 10%, 1% to 10%, 2% to 8%, 3% to 6%, 5% to 8% or 0.1% to 99% are contemplated by the invention.

In another embodiment, the modulation of the glycosylation of the protein results in an increase or a decrease in the amount or level of NA1F-GlcNAc species linked to the protein, for example, the amount or level of NA1F-GlcNAc species linked to the protein is increased or decreased by about 0.1%, 1%, 1.2%, 1.5%, 2%, 2.2%, 2.5%, 3%, 3.2%, 3.5%, 4%, 4.2%, 4.5%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 0.1-5%, 0.1-10%, 1% to 10%, 2% to 8%, 3% to 6%, 5% to 8% or 0.1% to 99% are contemplated by the invention.

In another embodiment, the modulation of the glycosylation of the protein results in an increase or a decrease in the amount or level of NA1F species linked to the protein, for example, the amount or level of NA1F species linked to the protein is increased or decreased by about 0.1%, 1%, 1.2%, 1.5%, 2%, 2.2%, 2.5%, 3%, 3.2%, 3.5%, 4%, 4.2%, 4.5%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 0.1-5%, 0.1-10%, 1% to 10%, 2% to 8%, 3% to 6%, 5% to 8% or 0.1% to 99% are contemplated by the invention.

In another embodiment, the modulation of the glycosylation of the protein results in an increase or a decrease in the amount or level of NA2F species linked to the protein, for example, the amount or level of NA2F species linked to the protein is increased or decreased by about 0.1%, 1%, 1.2%, 1.5%, 2%, 2.2%, 2.5%, 3%, 3.2%, 3.5%, 4%, 4.2%, 4.5%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 0.1-5%, 0.1-10%, 1% to 10%, 2% to 8%, 3% to 6%, 5% to 8% or 0.1% to 99% are contemplated by the invention.

In another embodiment, the modulation of the glycosylation of the protein results in an increase in the amount or level of NGA2F-GlcNAc, NA1F-GlcNAc, NA1F and/or NA2F species linked to the protein, for example the amount or level of NGA2F-GlcNAc, NA1F-GlcNAc, NA1F and/or NA2F linked to the protein is increased by about 0.1%, 1%, 1.2%, 1.5%, 2%, 2.2%, 2.5%, 3%, 3.2%, 3.5%, 4%, 4.2%, 4.5%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 0.1% to 5%, 0.1% to 10%, 0.1% to 20%, 1% to 10%, 1% to 20%, 2% to 8%, 3% to 6%, 3% to 20%, 5% to 8%, 5% to 20% or 0.1% to 99%.

In another embodiment, the modulation of the glycosylation of the protein results in a decrease in the amount or level of NGA2F, NA1F-GlcNAc, NA1F and/or NA2F species linked to the protein, for example the amount or level of NGA2F, NA1F-GlcNAc, NA1F and/or NA2F linked to the protein is decreased by about 0.1%, 1%, 1.2%, 1.5%, 2%, 2.2%, 2.5%, 3%, 3.2%, 3.5%, 4%, 4.2%, 4.5%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%. Ranges within one or more of the preceding values, e.g., about 0.1% to 5%, 0.1% to 10%, 0.1% to 20%, 0.1% to 30%, 0.1% to 40%, 0.1% to 50%, 0.1% to 60%, 0.1% to 65%, 1% to 10%, 1% to 20%, 1% to 30%, 1% to 40%, 1% to 50%, 1% to 60%, 1% to 65%, 5% to 10%, 5% to 20%, 5% to 30%, 5% to 40%, 5% to 50%, 5% to 60%, 5% to 65%, 10% to 20%, 10% to 30%, 10% to 40%, 10% to 50%, 10% to 60%, 10% to 65%, or 0.1 to 99%.

In another embodiment, the overall fucosylation level resulting from the modulation (e.g., increase or decrease) of any one of the fucosylated glycan species such as NGA2F-GlcNAc, NGA2F, NA1F-GlcNAc, NA1F and/or NA2F is decreased by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50%, 5-10%, 5-15%, 5-20%, 5-25%, 5-30%, 5-35%, 5-40%, 5-41%, 5-42%, 5-43, 5-44%, 5-45%, 5-46%, 5-47%, 5-48%, 5-49%, 5-50% or 1-99% are contemplated by the invention.

In another embodiment, the modulation of the glycosylation of the protein (e.g., antibody or DVD-Ig) results in an increase in the amount or level of mannosylation, for example, the amount or level of mannosylation is increased by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 1-5%, 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-5%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-5%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-5%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 1-99% are contemplated by the invention.

In another embodiment, the increase in mannosylation of the protein comprises an increase in the amount or level of a high mannose N-glycan oligosaccharide. A high-mannose N-glycan has more than one mannose linked to the non-reducing terminal of the core structure. For example, the high mannose N-glycan oligosaccharide is selected from the group consisting of Man 5 glycan, Man 6 glycan, Man 7 glycan and Man 8 glycan. In one embodiment, the amount or level of at least one of Man 5 glycan, Man 6 glycan, Man 7 glycan and/or Man 8 glycan is increased by about 0.1%, 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. Ranges within one or more of the preceding values, e.g., about 0.1-5%, 0.1-10%, 0.1-15%, 0.1-20%, 0.1-21%, 0.1-22%, 0.1-23%, 0.1-24%, 0.1-25%, 0.1-26%, 0.1-27%, 0.1-28%, 0.1-29%, 0.1-30%, 0.1-35%, 0.1-40%, 0.1-41%, 0.1-42%, 0.1-43%, 0.1-44%, 0.1-45%, 0.1-46%, 0.1-47%, 0.1-48%, 0.1-49%, 0.1-50%, 1-5%, 1-10%, 1-15%, 1-20%, 1-21%, 1-22%, 1-23%, 1-24%, 1-25%, 1-26%, 1-27%, 1-28%, 1-29%, 1-30%, 1-35%, 1-40%, 1-41%, 1-42%, 1-43%, 1-44%, 1-45%, 1-46%, 1-47%, 1-48%, 1-49%, 1-50%, 2-5%, 2-10%, 2-15%, 2-20%, 2-21%, 2-22%, 2-23%, 2-24%, 2-25%, 2-26%, 2-27%, 2-28%, 2-29%, 2-30%, 2-35%, 2-40%, 2-41%, 2-42%, 2-43%, 2-44%, 2-45%, 2-46%, 2-47%, 2-48%, 2-49%, 2-50%, 3-5%, 3-10%, 3-15%, 3-20%, 3-21%, 3-22%, 3-24%, 3-25%, 3-26%, 3-27%, 3-28%, 2-29%, 3-30%, 3-35%, 3-40%, 3-41%, 3-42%, 3-43%, 3-44%, 3-45%, 3-46%, 3-47%, 3-48%, 3-49%, 3-50%, 4-5%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 0.1-99% are contemplated by the invention.

It is known to those skilled in the art that differing protein glycosylation profiles may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, using the methods of the invention, one of skill in the art may modulate the glycosylation profile of a protein, e.g., an antibody or DVD-Ig to achieve a desired activity such as increased or decreased rate of clearance and/or increased ADCC activity.

Upstream Process Technologies

The methods of the present invention may be used to produce a protein (e.g., an antibody, or antigen binding fragment thereof, or a DVD-Ig) with a modulated glycosylation profile. In one embodiment, the methods of the invention involve modification of the conditions used during upstream protein production, such as recombinant cell culture conditions. For example, the methods of the invention comprise supplementing the recombinant cell culture media with a monosaccharide (e.g., tagatose) and/or oligosaccharide (e.g., sucrose) to modulate the glycosylation profile of the protein.

The upstream process technologies may be used alone or in combination with the downstream process technologies described below.

In one embodiment, the methods described herein produce a protein with a modulated glycosylation profile wherein the overall fucosylation level resulting from the modulation of any one of the fucosylated glycan species such as NGA2F-GlcNAc, NGA2F, NA1F-GlcNAc, NA1F and/or NA2F, is decreased by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 99%, and ranges within one or more of the preceding. In one aspect of this embodiment, the overall fucosylation level is decreased by about 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50% 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50%, 5-10%, 5-15%, 5-20%, 5-25%, 5-30%, 5-35%, 5-40%, 5-41%, 5-42%, 5-43, 5-44%, 5-45%, 5-46%, 5-47%, 5-48%, 5-49%, 5-50% or 1-99% and ranges within one or more of the preceding.

In another embodiment, the methods described herein produce a protein with a modulated glycosylation profile wherein the overall mannosylation level resulting from the modulation of any one of the high mannose N-glycan oligosaccharides, such as Man 5 glycan, Man 6 glycan, Man 7 glycan or Man 8 glycan, is increased by about 0.1%, 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 99%, and ranges within one or more of the preceding. In one aspect of this embodiment, the overall high mannose N-glycan level is increased by about 0.1-5%, 0.1-10%, 0.1-15%, 0.1-20%, 0.1-21%, 0.1-22%, 0.1-23%, 0.1-24%, 0.1-25%, 0.1-26%, 0.1-27%, 0.1-28%, 0.1-29%, 0.1-30%, 0.1-35%, 0.1-40%, 0.1-41%, 0.1-42%, 0.1-43%, 0.1-44%, 0.1-45%, 0.1-46%, 0.1-47%, 0.1-48%, 0.1-49%, 0.1-50%, 1-5%, 1-10%, 1-15%, 1-20%, 1-21%, 1-22%, 1-23%, 1-24%, 1-25%, 1-26%, 1-27%, 1-28%, 1-29%, 1-30%, 1-35%, 1-40%, 1-41%, 1-42%, 1-43%, 1-44%, 1-45%, 1-46%, 1-47%, 1-48%, 1-49%, 1-50%, 2-5%, 2-10%, 2-15%, 2-20%, 2-21%, 2-22%, 2-23%, 2-24%, 2-25%, 2-26%, 2-27%, 2-28%, 2-29%, 2-30%, 2-35%, 2-40%, 2-41%, 2-42%, 2-43%, 2-44%, 2-45%, 2-46%, 2-47%, 2-48%, 2-49%, 2-50%, 3-5%, 3-10%, 3-15%, 3-20%, 3-21%, 3-22%, 3-24%, 3-25%, 3-26%, 3-27%, 3-28%, 2-29%, 3-30%, 3-35%, 3-40%, 3-41%, 3-42%, 3-43%, 3-44%, 3-45%, 3-46%, 3-47%, 3-48%, 3-49%, 3-50%, 4-5%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 0.1-99%, and ranges within one or more of the preceding.

In certain embodiments, the methods described herein produce a protein, e.g., an antibody, with a modulated glycosylation profile wherein the antibody's antibody-dependent cellular cytotoxicity (ADCC) response is increased by about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99%, and ranges within one or more of the preceding. In one aspect of this embodiment, the antibody's ADCC response is increased by about 1-5%, 1-10%, 1-15%, 1-20%, 1-25%, 1-30%, 1-35%, 1-40%, 1-45%, 1-50%, 5-10%, 5-15%, 5-20%, 5-25%, 5-30%, 5-35%, 5-40%, 5-45%, 5-50%, 8-10%, 8-15%, 8-20%, 8-25%, 8-30%, 8-35%, 8-40%, 8-45%, 8-50%, 10-15%, 10-20%, 10-25%, 10-30%, 10-35%, 10-40%, 10-45%, 10-50%, 20-25%, 20-30%, 20-35%, 20-40%, 20-45%, 20-50% or 1-99%, and ranges within one or more of the preceding.

As described herein, the host cell culture conditions can be modified as compared to conditions during production of the same protein without modulation of the glycosylation profile. In one embodiment, a protein with a modulated glycosylation profile is produced by culturing cells expressing the antibody, or antigen binding fragment thereof, or DVD-Ig in a cell culture media supplemented with an oligosaccharide (e.g., sucrose) and/or a monosaccharide (e.g., tagatose).

To express a protein with a modulated glycosylation profile (e.g., an antibody, or antigen-binding fragment thereof, or DVD-Ig), DNAs encoding the protein, such as DNAs encoding partial or full-length light and heavy chains in the case of antibodies, are inserted into one or more expression vector such that the genes are operatively linked to transcriptional and translational control sequences. (See, e.g., U.S. Pat. No. 6,090,382, the entire contents of which are incorporated herein by reference.) In this context, the term "operatively linked" is intended to mean that a gene encoding the protein is ligated into a vector such that transcriptional and translational control sequences within the vector serve their intended function of regulating the transcription and translation of the gene. The expression vector and expression control sequences are chosen to be compatible with the expression host cell used. In certain embodiments, the protein with a modulated glycosylation profile will comprising multiple polypeptides, such as the heavy and light chains of an antibody. Thus, in certain embodiments, genes encoding multiple polypeptides, such as antibody light chain genes and antibody heavy chain genes, can be inserted into a separate vector or, more typically, the genes are inserted into the same expression vector. Genes are inserted into expression vectors by standard methods (e.g., ligation of complementary restriction sites on the gene fragment and vector, or blunt end ligation if no restriction sites are present). Prior to insertion of the gene or genes, the expression vector may already carry additional polypeptide sequences, such as, but not limited to, antibody constant region sequences. For example, one approach to converting the anti-TNFα antibody or anti-TNFα antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the protein from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein).

In addition to protein coding genes, a recombinant expression vector can carry one or more regulatory sequence that controls the expression of the protein coding genes in a host cell. The term "regulatory sequence" is intended to include promoters, enhancers and other expression control elements (e.g., polyadenylation signals) that control the transcription or translation of the protein coding genes. Such regulatory sequences are described, e.g., in Goeddel; Gene Expression Technology Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

A recombinant expression vector may also carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antigen binding fragment thereof, to be used in the method of preparing a protein with a modulated glycosylation profile can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of a protein, for example, the light and heavy chains of an antibody, the expression vector(s) encoding the protein is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active protein. Prokaryotic expression of protein genes has been reported to be ineffective for production of high yields of active protein (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of proteins with modulated glycosylation profiles, for example, glycosylated antibodies, are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

Mammalian cells can be used for expression and production of the protein compositions of the invention, however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding protein genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for protein production and cultured in conventional nutrient media modified as appropriate for inducing promoters, selecting transformants, or amplifying the genes encoding the desired sequences.

The host cells used to produce a protein may be cultured in a variety of media which are supplemented in accordance with the present invention. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma), Iscove's Modified Dulbecco's Medium, Minimal Essential Medium-alpha. (MEM-alpha), DME/F12, alpha MEM, Basal Medium Eagle with Earle's BSS, DMEM high Glucose, with L-Glutamine, DMEM high glucose, without L-Glutamine, DMEM low Glucose, without L-Glutamine, DMEM:F12 1:1, with L-Glutamine, GMEM (Glasgow's MEM), GMEM with L-glutamine, Grace's Complete Insect Medium, Grace's Insect Medium, without FBS, Ham's F-10, with L-Glutamine, Ham's F-12, with L-Glutamine, IMDM with HEPES and L-Glutamine, IMDM with HEPES and without L-Glutamine, IPL-41 Insect Medium, L-15 (Leibovitz)(2.times.), without L-Glutamine or Phenol Red, L-15 (Leibovitz), without L-Glutamine, McCoy's 5A Modified Medium, Medium 199, MEM Eagle, without L-Glutamine or Phenol Red (2.times.), MEM Eagle-Earle's BSS, with L-glutamine, MEM Eagle-Earle's BSS, without L-Glutamine, MEM Eagle-Hanks BSS, without L-Glutamine, NCTC-109, with L-Glutamine, Richter's CM Medium, with L-Glutamine, RPMI 1640 with HEPES, L-Glutamine and/or Penicillin-Streptomycin, RPMI 1640, with L-Glutamine, RPMI 1640, without L-Glutamine, Schneider's Insect Medium are suitable for culturing host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact proteins, for example, antibodies, including Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody. Recombinant DNA technology may also be used to remove some or all of the DNA encoding either or both of the light and heavy chains that is not necessary for binding to an antigen. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the target antibody, depending on the specificity of the antibody of the invention, by crosslinking an antibody of the invention to a second antibody by standard chemical crosslinking methods.

In a suitable system for recombinant expression of a protein, for example, an antibody, or antigen-binding portion thereof, or a DVD-Ig, a recombinant expression vector encoding the protein, for example, both an antibody heavy chain and an antibody light chain, is introduced into dhfr-CHO cells by calcium phosphate-mediated transfection. Within the recombinant expression vector, the protein gene(s) are each operatively linked to CMV enhancer/AdMLP promoter regulatory elements to drive high levels of transcription of the gene(s). The recombinant expression vector also carries a DHFR gene, which allows for selection of CHO cells that have been transfected with the vector using methotrexate selection/amplification. The selected transformant host cells are cultured to allow for expression of the protein, for example, the antibody heavy and light chains, and intact protein, for example, an antibody, is recovered from the culture medium. Standard molecular biology techniques are used to prepare the recombinant expression vector, transfect the host cells, select for transformants, culture the host cells and recover the protein from the culture medium.

When using recombinant techniques, the protein, for example, antibodies or antigen binding fragments thereof, can be produced intracellularly, in the periplasmic space, or directly secreted into the medium. In one aspect, if the protein is produced intracellularly, as a first step, the particulate debris, either host cells or lysed cells (e.g., resulting from homogenization), can be removed, e.g., by centrifugation or ultrafiltration. Where the protein is secreted into the medium, supernatants from such expression systems can be first concentrated using a commercially available protein concentration filter, e.g., an Amicon™ or Millipore Pellicon™ ultrafiltration unit.

Some antibodies can be secreted directly from the cell into the surrounding growth media; others are made intracellularly. For antibodies made intracellularly, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

In accordance with the present invention, modulation of the glycosylation profile of the protein (e.g., antibody or DVD-Ig) produced by recombinant cell culture can be achieved by supplementation of the cell culture media with sucrose and/or tagatose. Specific host cell culture conditions can be used with various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired host cell line.

Supplementation with Monosaccharides and/or Oligosaccharides to Modulate the Glycosylation Profile of the Expressed Protein The present invention relates to modulation of the glycosylation profile in mammalian cell culture processes using cell culture component such as monosaccharide and/or oligosaccharide supplementation. These nutrients are also important for ensuring both robust cell growth and production of glycoproteins. In the present invention these components are utilized to affect the profile of glycosylation of the glycoprotein. For example, but not by way of limitation, by adjusting the concentration of one or both of these sugars the glycosylation profile can be modulated. Thus, the present invention provides methods to modulate the glycosylation profile introduced by upstream process technologies to achieve desired product glycosylation profiles.

In certain embodiments, a protein with a modulated glycosylation profile is prepared by supplementation of cell culture media with monosaccharides (e.g., tagatose) and/or oligosaccharides (e.g., sucrose). For example, supplementation with sucrose and/or tagatose results in a significant increase in non-fully processed N-glycans, including high mannose N-glycan species. This is consistent with the abrogation of the N-glycan biosynthetic pathway at the enzymatic reaction steps shown in FIG. 2, which results in the accumulation of these particular N-glycans. For some particular recombinant glycoproteins, a high mannose isoform is a desired product quality attribute (Walsh, G. et al., (2006) Nat. Biotechnol. 24(10):1241-52). In addition, as a result of the increase in mannosylation, the levels of fucosylation are significantly decreased. The addition of fucose to N-glycans has been shown to reduce antibody dependent cellular cytotoxicity (ADCC) (Kanda Y. et al., (2007) Glycobiology, 17(1):104-18; Shields R. L., et al., (2002) J. Biol. Chem. 2002. 277(30): 26733-26740). Thus, where the ADCC response is the principle therapeutic mechanism of antibody activity, the provision of methods for the preparation of recombinant protein therapeutics with a glycosylation profile characterized by decreased fucosylation, are beneficial.

In certain embodiments, the cell culture media is supplemented with one or more monosaccharides or oligosaccharides in order to modulate the glycosylation profile of the protein (e.g., an antibody, of antigen binding fragment thereof, or a DVD-Ig). In one embodiment the monosaccharide is tagatose. In one embodiment the cell culture media is supplemented with about 1 mM, 5 mM, 6 mM, 7 mM, 8 mM, 9 mM, 10 mM, 15 mM, 20 mM, 30 mM, 40 mM, 50 mM, 60 mM, 70 mM, 80 mM, 90 mM or 100 mM tagatose. In particular embodiments, the cell culture media is supplemented with about 1 mM, 10 mM, 30 mM, 50 mM or 70 mM tagatose.

In another embodiment the oligosaccharide is sucrose. In one embodiment the cell culture media is supplemented with about 1 mM, 5 mM, 6 mM, 7 mM, 8 mM, 9 mM, 10 mM, 15 mM, 20 mM, 30 mM, 40 mM, 50 mM, 60 mM, 70 mM, 80 mM, 90 mM or 100 mM sucrose. In particular embodiments, the cell culture media is supplemented with about 1 mM, 7 mM, 10 mM, 15 mM, 30 mM, 50 mM or 70 mM sucrose.

In certain embodiments, the cell culture media is supplemented with one or more monosaccharides or oligosaccharides in an amount effective to modulate the glycosylation profile of the protein such that the overall fucosylation amount or level, resulting from the modulation of at least one of the fucosylated glycan species such as NGA2F-GlcNAc, NGA2F, NA1F-GlcNAc, NA1F and/or NA2F, is decreased by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 99%, and ranges within one or more of the preceding. In one aspect of this embodiment, the overall fucosylation amount or level is decreased by about 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50%, 5-10%, 5-15%, 5-20%, 5-25%, 5-30%, 5-35%, 5-40%, 5-41%, 5-42%, 5-43, 5-44%, 5-45%, 5-46%, 5-47%, 5-48%, 5-49%, 5-50% or 1-99%, and ranges within one or more of the preceding.

In certain embodiments, the cell culture media is supplemented with one or more monosaccharides or oligosaccharides in an amount effective to modulate the glycosylation profile of the protein such that the overall mannosylation amount or level, resulting from the modulation of at least one of the high mannose N-glycan oligosaccharides, such as Man 5 glycan, Man 6 glycan, Man 7 glycan or Man 8 glycan, is increased by about 0.1%, 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 99%, and ranges within one or more of the preceding. In one aspect of this embodiment, the overall high mannose N-glycan amount or level is increased by about 0.1-5%, 0.1-10%, 0.1-15%, 0.1-20%, 0.1-21%, 0.1-22%, 0.1-23%, 0.1-24%, 0.1-25%, 0.1-26%, 0.1-27%, 0.1-28%, 0.1-29%, 0.1-30%, 0.1-35%, 0.1-40%, 0.1-41%, 0.1-42%, 0.1-43%, 0.1-44%, 0.1-45%, 0.1-46%, 0.1-47%, 0.1-48%, 0.1-49%, 0.1-50%, 1-5%, 1-10%, 1-15%, 1-20%, 1-21%, 1-22%, 1-23%, 1-24%, 1-25%, 1-26%, 1-27%, 1-28%, 1-29%, 1-30%, 1-35%, 1-40%, 1-41%, 1-42%, 1-43%, 1-44%, 1-45%, 1-46%, 1-47%, 1-48%, 1-49%, 1-50%, 2-5%, 2-10%, 2-15%, 2-20%, 2-21%, 2-22%, 2-23%, 2-24%, 2-25%, 2-26%, 2-27%, 2-28%, 2-29%, 2-30%, 2-35%, 2-40%, 2-41%, 2-42%, 2-43%, 2-44%, 2-45%, 2-46%, 2-47%, 2-48%, 2-49%, 2-50%, 3-5%, 3-10%, 3-15%, 3-20%, 3-21%, 3-22%, 3-24%, 3-25%, 3-26%, 3-27%, 3-28%, 2-29%, 3-30%, 3-35%, 3-40%, 3-41%, 3-42%, 3-43%, 3-44%, 3-45%, 3-46%, 3-47%, 3-48%, 3-49%, 3-50%, 4-5%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 0.1-99%, and ranges within one or more of the preceding.

In certain embodiments, the cell culture media is supplemented with one or more monosaccharides or oligosaccharides in an amount effective to modulate the glycosylation profile of the protein, e.g., an antibody, such that the antibody's antibody-dependent cellular cytotoxicity (ADCC) response is increased by about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99%, and ranges within one or more of the preceding. In one aspect of this embodiment, the antibody's ADCC response is increased by about 5%, 10%, 15%, 20%, 25%, 30%, 35%, 40%, 45%, 50%, or by about 1-5%, 1-10%, 1-15%, 1-20%, 1-25%, 1-30%, 1-35%, 1-40%, 1-45%, 1-50%, 5-10%, 5-15%, 5-20%, 5-25%, 5-30%, 5-35%, 5-40%, 5-45%, 5-50%, 8-10%, 8-15%, 8-20%, 8-25%, 8-30%, 8-35%, 8-40%, 8-45%, 8-50%, 10-15%, 10-20%, 10-25%, 10-30%, 10-35%, 10-40%, 10-45%, 10-50%, 20-25%, 20-30%, 20-35%, 20-40%, 20-45%, 20-50% or 1-99%, and ranges within one or more of the preceding.

In certain embodiments, the cell culture media is supplemented, for example, at the start of culture, or in a fed-batch or in a continuous manner. The feed amounts may be calculated to achieve a certain concentration based on off-line or on-line measurements. The addition of one or more supplements may be based on measured glycosylation profiles. The resulting media can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, incubation vessels, microtiter plates, capillaries, multi-well plates and any other configuration appropriate for optimal growth and productivity of the desired host cell line. Additional cell culture equipment may be used such as fermentor tanks, air lifts, culture flasks, spinner flasks, microcarriers, fluidized beds, hollow fibers, roller bottles or packed beds. In addition, the harvest criterion for these cultures may be chosen, for example, based on choice of harvest viability or culture duration, to further optimize a certain targeted glycosylation profiles.

Down Stream Process Technologies

The protein compositions of the invention may be purified using downstream process technologies (e.g., purification or concentration), following production using the upstream process technologies of the present invention. For example, once a clarified solution or mixture comprising the protein with a modulated glycosylation profile, e.g., an antibody or DVD-Ig, has been obtained, separation of the protein from process-related impurities, such as the other proteins produced by the host cell, as well as product-related substances, such acidic or basic variants, is performed. In certain embodiments, the initial steps of the purification methods involve the clarification and primary recovery of an antibody or DVD-Ig from a sample matrix by methods such as centrifugation, depth filtration and/or viral inactivation/reduction. In certain non-limiting embodiments, further separation is performed using cation exchange chromatography, anion exchange chromatography, and/or multi-mode chromatography. In certain embodiments, a combination of one or more different purification techniques, including affinity separation step(s), ion exchange separation step(s), mixed-mode step(s), and/or hydrophobic interaction separation step(s) can also be employed. Such additional purification steps separate mixtures of proteins on the basis of their charge, degree of hydrophobicity, and/or size. Continuous and recycle chromatography are also applicable to chromatography methods where the protein with a modulated glycosylation profile is collected in the unbound faction during chromatography or where the protein is first bound to the chromatography resin and subsequently recovered by washing the media with conditions that elute the bound component. Numerous chromatography resins are commercially available for each of these techniques, allowing accurate tailoring of the purification scheme to the particular protein involved. Each of the separation methods allow proteins to either traverse at different rates through a column, achieving a physical separation that increases as they pass further through the column, or to adhere selectively to a separation resin (or medium). The proteins are then differentially eluted using different eluents. In some cases, the protein with a modulated glycosylation profile is separated from impurities when the impurities specifically adhere to the column's resin and the protein does not, i.e., the protein is contained in the effluent, while in other cases the protein will adhere to the column's resin, while the impurities and/or product-related substances are extruded from the column's resin during a wash cycle. Following chromatographic polishing steps the protein compositions of the invention may be further purified using viral filtration. Ultrafiltration and/or diafiltration may be used to further concentrate and formulate the protein, e.g., an antibody or DVD-Ig product.

The glycosylation profile of the protein prepared by the methods of the invention can be analyzed using methods well known to those skilled in the art, e.g., removal and derivatization of N-glycans followed by NP-HPLC analysis, weak cation exchange chromatography (WCX), capillary isoelectric focusing (cIEF), size-exclusion chromatography, Poros A HPLC Assay, Host cell Protein ELISA, DNA assay, and western blot analysis.

III. Methods of Treatment Using Proteins with Modulated Glycosylation Profiles of the Invention The compositions comprising a protein with a modulated glycosylation profile, for example a protein such as an antibody, antigen-binding portion thereof, or a DVD-Ig, with a decreased fucosylation level or amount and/or an increased mannosylation level or amount, of the invention may be used to treat any disorder in a subject for which the therapeutic protein (e.g., an antibody, or an antigen binding fragment thereof, or a DVD-Ig) comprised in the composition is appropriate for treating.

A "disorder" is any condition that would benefit from treatment with the therapeutic protein with a modulated glycosylation profile. This includes chronic and acute disorders or diseases including those pathological conditions which predispose the subject to the disorder in question. In the case of an anti-TNFα antibody, or antigen binding fragment thereof, such as adalimumab, a therapeutically effective amount of the composition comprising a protein with a modulated glycosylation profile may be administered to treat a disorder in which TNFα activity is detrimental.

A disorder in which TNFα activity is detrimental includes a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody.

TNFα has been implicated in the pathophysiology of a wide variety of a TNFα-related disorders including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503). Accordingly, the protein with a modulated glycosylation profile of the invention may be used to treat an autoimmune disease, such as rheumatoid arthritis, juvenile idiopathic arthritis, or psoriatic arthritis, an intestinal disorder, such as Crohn's disease or ulcerative colitis, a spondyloarthropathy, such as ankylosing spondylitis, or a skin disorder, such as psoriasis.

Disorders in which TNFα activity is detrimental are well known in the art and described in detail in U.S. Pat. No. 8,231,876 and U.S. Pat. No. 6,090,382, the entire contents of each of which are expressly incorporated herein by reference. In one embodiment, "a disorder in which TNFα activity is detrimental" includes sepsis (including septic shock, endotoxic shock, gram negative sepsis and toxic shock syndrome), autoimmune diseases (including rheumatoid arthritis, rheumatoid spondylitis, osteoarthritis and gouty arthritis, allergy, multiple sclerosis, autoimmune diabetes, autoimmune uveitis, nephrotic syndrome, multisystem autoimmune diseases, lupus (including systemic lupus, lupus nephritis and lupus cerebritis), Crohn's disease and autoimmune hearing loss), infectious diseases (including malaria, meningitis, acquired immune deficiency syndrome (AIDS), influenza and cachexia secondary to infection), allograft rejection and graft versus host disease, malignancy, pulmonary disorders (including adult respiratory distress syndrome (ARDS), shock lung, chronic pulmonary inflammatory disease, pulmonary sarcoidosis, pulmonary fibrosis, silicosis, idiopathic interstitial lung disease and chronic obstructive airway disorders (COPD), such as asthma), intestinal disorders (including inflammatory bowel disorders, idiopathic inflammatory bowel disease, Crohn's disease and Crohn's disease-related disorders (including fistulas in the bladder, vagina, and skin; bowel obstructions; abscesses; nutritional deficiencies; complications from corticosteroid use; inflammation of the joints; erythem nodosum; pyoderma gangrenosum; lesions of the eye, Crohn's related arthralgias, fistulizing Crohn's indeterminant colitis and pouchitis), cardiac disorders (including ischemia of the heart, heart insufficiency, restenosis, congestive heart failure, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, cardiomyopathy, coronary artery spasm, coronary artery disease, valvular disease, arrhythmias, and cardiomyopathies), spondyloarthropathies (including ankylosing spondylitis, psoriatic arthritis/spondylitis, enteropathic arthritis, reactive arthritis or Reiter's syndrome, and undifferentiated spondyloarthropathies), metabolic disorders (including obesity and diabetes, including type 1 diabetes mellitus, type 2 diabetes mellitus, diabetic neuropathy, peripheral neuropathy, diabetic retinopathy, diabetic ulcerations, retinopathy ulcerations and diabetic macrovasculopathy), anemia, pain (including acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis), hepatic disorders (including hepatitis, alcoholic hepatitis, viral hepatitis, alcoholic cirrhosis, a1 antitypsin deficiency, autoimmune cirrhosis, cryptogenic cirrhosis, fulminant hepatitis, hepatitis B and C, and steatohepatitis, cystic fibrosis, primary biliary cirrhosis, sclerosing cholangitis and biliary obstruction), skin and nail disorders (including psoriasis (including chronic plaque psoriasis, guttate psoriasis, inverse psoriasis, pustular psoriasis and other psoriasis disorders), pemphigus vulgaris, scleroderma, atopic dermatitis (eczema), sarcoidosis, erythema nodosum, hidradenitis suppurative, lichen planus, Sweet's syndrome, scleroderma and vitiligo), vasculitides (including Behcet's disease), and other disorders, such as juvenile rheumatoid arthritis (JRA), endometriosis, prostatitis, choroidal neovascularization, sciatica, Sjogren's syndrome, uveitis, wet macular degeneration, osteoporosis, osteoarthritis, active axial spondyloarthritis and non-radiographic axial spondyloarthritis.

As used herein, the term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the term "treatment" or "treat" refers to both therapeutic treatment and prophylactic or preventative measures. Those in need of treatment include those already with the disorder, as well as those in which the disorder is to be prevented.

In one embodiment, the invention provides a method of administering a composition comprising a protein with a modulated glycosylation profile, such as an anti-TNFα antibody, or antigen binding fragment thereof, to a subject such that TNFα activity is inhibited or a disorder in which TNFα activity is detrimental is treated. In one embodiment, the TNFα is human TNFα and the subject is a human subject. In one embodiment, the anti-TNFα antibody is adalimumab, also referred to as HUMIRA®.

The compositions comprising a protein with a modulated glycosylation profile can be administered by a variety of methods known in the art. Exemplary routes/modes of administration include subcutaneous injection, intravenous injection or infusion. In certain aspects, a composition comprising a protein with a modulated glycosylation profile may be orally administered. As will be appreciated by the skilled artisan, the route and/or mode of administration will vary depending upon the desired results.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a composition comprising a protein with a modulated glycosylation profile of the invention is 0.01-20 mg/kg, or 1-10 mg/kg, or 0.3-1 mg/kg. With respect to a composition comprising a protein such as an anti-TNFα antibody with a modulated glycosylation profile, or antigen-binding portion thereof, such as adalimumab, an exemplary dose is 40 mg every other week. In some embodiments, in particular for treatment of ulcerative colitis or Crohn's disease, an exemplary dose includes an initial dose (Day 1) of 160 mg (e.g., four 40 mg injections in one day or two 40 mg injections per day for two consecutive days), a second dose two weeks later of 80 mg, and a maintenance dose of 40 mg every other week beginning two weeks later. Alternatively, for psoriasis for example, a dosage can include an 80 mg initial dose followed by 40 mg every other week starting one week after the initial dose.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

IV. Pharmaceutical Formulations Containing Compositions Comprising Proteins with Modulated Glycosylation Profiles of the Invention The present invention further provides preparations and formulations comprising compositions comprising a protein with a modulated glycosylation profile, for example a protein such as an antibody, antigen-binding portion thereof, or a DVD-Ig, with a decreased fucosylation level or amount and/or an increased mannosylation level or amount. It should be understood that any of the compositions comprising the proteins with modulated glycosylation profiles, such as antibodies, antibody fragments and DVD-Igs described herein, may be formulated or prepared as described below. In one embodiment, the antibody is an anti-TNFα antibody, or antigen-binding portion thereof.

In certain embodiments, the compositions comprising a protein with a modulated glycosylation profile, of the invention may be formulated with a pharmaceutically acceptable carrier as pharmaceutical (therapeutic) compositions, and may be administered by a variety of methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the protein with a modulated glycosylation profile (e.g., antibodies or DVD-Igs) of the present invention, and with each other, in a manner such that there is no interaction which would substantially impair the desired pharmaceutical efficacy.

The compositions comprising a protein with a modulated glycosylation profile, of the invention are present in a form known in the art and acceptable for therapeutic uses. In one embodiment, a formulation of the compositions comprising a protein with a modulated glycosylation profile, of the invention is a liquid formulation. In another embodiment, a formulation of the compositions comprising a protein with a modulated glycosylation profile, of the invention is a lyophilized formulation. In a further embodiment, a formulation of the compositions comprising a protein with a modulated glycosylation profile, of the invention is a reconstituted liquid formulation. In one embodiment, a formulation of the compositions comprising a protein with a modulated glycosylation profile, of the invention is a stable liquid formulation. In one embodiment, a liquid formulation of the compositions comprising a protein with a modulated glycosylation profile, of the invention is an aqueous formulation. In another embodiment, the liquid formulation is non-aqueous. In a specific embodiment, a liquid formulation of the compositions comprising a protein with a modulated glycosylation profile, of the invention is an aqueous formulation wherein the aqueous carrier is distilled water.

The formulations of the compositions comprising a protein with a modulated glycosylation profile (e.g., an antibody or a DVD-Ig) in a concentration resulting in a w/v appropriate for a desired dose. The protein with a modulated glycosylation profile may be present in the formulation at a concentration of about 1 mg/ml to about 500 mg/ml, e.g., at a concentration of at least 1 mg/ml, at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

In a specific embodiment, a formulation of compositions comprising a protein with a modulated glycosylation profile, of the invention comprises at least about 100 mg/ml, at least about 125 mg/ml, at least 130 mg/ml, or at least about 150 mg/ml of protein with a modulated glycosylation profile (e.g., an antibody or DVD-Ig) of the invention.

In one embodiment, the concentration of a protein with a modulated glycosylation profile (e.g., antibody or DVD-Ig), which is included in the formulation of the invention, is between about 1 mg/ml and about 25 mg/ml, between about 1 mg/ml and about 200 mg/ml, between about 25 mg/ml and about 200 mg/ml, between about 50 mg/ml and about 200 mg/ml, between about 75 mg/ml and about 200 mg/ml, between about 100 mg/ml and about 200 mg/ml, between about 125 mg/ml and about 200 mg/ml, between about 150 mg/ml and about 200 mg/ml, between about 25 mg/ml and about 150 mg/ml, between about 50 mg/ml and about 150 mg/ml, between about 75 mg/ml and about 150 mg/ml, between about 100 mg/ml and about 150 mg/ml, between about 125 mg/ml and about 150 mg/ml, between about 25 mg/ml and about 125 mg/ml, between about 50 mg/ml and about 125 mg/ml, between about 75 mg/ml and about 125 mg/ml, between about 100 mg/ml and about 125 mg/ml, between about 25 mg/ml and about 100 mg/ml, between about 50 mg/ml and about 100 mg/ml, between about 75 mg/ml and about 100 mg/ml, between about 25 mg/ml and about 75 mg/ml, between about 50 mg/ml and about 75 mg/ml, or between about 25 mg/ml and about 50 mg/ml.

In a specific embodiment, a formulation of the compositions comprising a protein with a modulated glycosylation profile of the invention comprises between about 90 mg/ml and about 110 mg/ml or between about 100 mg/ml and about 210 mg/ml of a protein with a modulated glycosylation profile (e.g., an antibody or DVD-Ig).

The formulations of the compositions comprising a protein with a modulated glycosylation profile of the invention comprising a protein (e.g., an antibody or DVD-Ig) may further comprise one or more active compounds as necessary for the particular indication being treated, typically those with complementary activities that do not adversely affect each other. Such additional active compounds are suitably present in combination in amounts that are effective for the purpose intended.

The formulations of the compositions comprising a protein with a modulated glycosylation profile may be prepared for storage by mixing the protein (e.g., antibody or DVD-Ig) having the desired degree of purity with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (Goodman and Gilman's The Pharmacological Basis of Therapeutics, 12$^{th}$ edition, L. Brunton, et al. and *Remington's Pharmaceutical Sciences*, 16th edition, Osol, A. Ed. (1999)), in the form of lyophilized formulations or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

The buffering agent may be histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, $MgCl_2$, or $CaCl_2$ The formulations of the compositions comprising a protein with a modulated glycosylation profile of the invention may include a buffering or pH adjusting agent to provide improved pH control. A formulation of the invention may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, a formulation of the invention has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a formulation of the invention has a pH of about 6.0. One of skill in the art understands that the pH of a formulation generally should not be equal to the isoelectric point of the particular a protein (e.g., antibody or DVD-Ig) to be used in the formulation.

Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is chosen from histidine, citrate, phosphate, glycine, and acetate. In a specific embodiment, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, 13$^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, 2$^{nd}$ Edition, Chapter 5, p. 194, De Luca and Boylan, "Formulation of Small Volume Parenterals", Table 5: Commonly used additives in Parenteral Products. In one embodiment, the buffering agent is at a concentration of about 1 mM, or of about 5 mM, or of about 10 mM, or of about 15 mM, or of about 20 mM, or of about 25 mM, or of about 30 mM, or of about 35 mM, or of about 40 mM, or of about 45 mM, or of about 50 mM, or of about 60 mM, or of about 70 mM, or of about 80 mM, or of about 90 mM, or of about 100 mM. In one embodiment, the buffering agent is at a concentration of 1 mM, or of 5 mM, or of 10 mM, or of 15 mM, or of 20 mM, or of 25 mM, or of 30 mM, or of 35 mM, or of 40 mM, or of 45 mM, or of 50 mM, or of 60 mM, or of 70 mM, or of 80 mM, or of 90 mM, or of 100 mM. In a specific embodiment, the buffering agent is at a concentration of between about 5 mM and about 50 mM. In another specific embodiment, the buffering agent is at a concentration of between 5 mM and 20 mM.

In certain embodiments, the formulation of the compositions comprising a protein with a modulated glycosylation profile of the invention comprises histidine as a buffering agent. In one embodiment the histidine is present in the formulation of the invention at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a formulation of the invention comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the formulation comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In a specific embodiment, a formulation may comprise about 10 mM, about 25 mM, or no histidine.

The formulations of the compositions comprising a protein with a modulated glycosylation profile of the invention may comprise a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, between about 1% to about 20%, between about 5% to about 15%, between about 8% to about 10%, between about 10% and about 15%, between about 15% and about 20%, between about 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

Carbohydrate excipients suitable for use in the formulations of the invention include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In one embodiment, the carbohydrate excipients for use in the present invention are chosen from, sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In a specific embodiment, the formulations of the compositions comprising a protein with a modulated glycosylation profile of the invention may comprise trehalose. In one embodiment, a formulation of the invention comprises at least about 1%, at least about 2%, at least about 4%, at least about 8%, at least about 20%, at least about 30%, or at least about 40% trehalose. In another embodiment, a formulation of the invention comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a formulation of the invention comprises about 1%, about 2%, about 4%, about 6%, about 8%, about 15%, about 20%, about 30%, or about 40% trehalose. In a specific embodiment, a formulation of the invention comprises about 4%, about 6% or about 15% trehalose.

In certain embodiments, a formulation of the compositions comprising a protein with a modulated glycosylation profile of the invention comprises an excipient. In a specific embodiment, a formulation of the invention comprises at least one excipient chosen from: sugar, salt, surfactant, amino acid, polyol, chelating agent, emulsifier and preservative. In one embodiment, a formulation of the invention comprises a salt, e.g., a salt selected from: NaCl, KCl, CaCl$_2$, and MgCl$_2$. In a specific embodiment, the formulation comprises NaCl.

A formulation of the compositions comprising a protein with a modulated glycosylation profile of the invention may comprise at least about 10 mM, at least about 25 mM, at least about 50 mM, at least about 75 mM, at least about 80 mM, at least about 100 mM, at least about 125 mM, at least about 150 mM, at least about 175 mM, at least about 200 mM, or at least about 300 mM sodium chloride (NaCl). In a further embodiment, the formulation may comprise between about 10 mM and about 300 mM, between about 10 mM and about 200 mM, between about 10 mM and about 175 mM, between about 10 mM and about 150 mM, between about 25 mM and about 300 mM, between about 25 mM and about 200 mM, between about 25 mM and about 175 mM, between about 25 mM and about 150 mM, between about 50 mM and about 300 mM, between about 50 mM and about 200 mM, between about 50 mM and about 175 mM, between about 50 mM and about 150 mM, between about 75 mM and about 300 mM, between about 75 mM and about 200 mM, between about 75 mM and about 175 mM, between about 75 mM and about 150 mM, between about 100 mM and about 300 mM, between about 100 mM and about 200 mM, between about 100 mM and about 175 mM, or between about 100 mM and about 150 mM sodium chloride. In a further embodiment, the formulation may comprise about 10 mM, about 25 mM, about 50 mM, about 75 mM, about 80 mM, about 100 mM, about 125 mM, about 150 mM, about 175 mM, about 200 mM, or about 300 mM sodium chloride.

A formulation of the compositions comprising a protein with a modulated glycosylation profile of the invention may also comprise an amino acid, e.g., lysine, arginine, glycine, histidine or an amino acid salt. The formulation may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the formulation may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a formulation of the invention comprises about 1 mM, 1.6 mM, 25 mM, about 50 mM, about 100 mM, about 150 mM, about 200 mM, about 250 mM, about 300 mM, about 350 mM, or about 400 mM of an amino acid.

The formulations of the compositions comprising a protein with a modulated glycosylation profile of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™ PF68, etc.), can optionally be added to the formulations of the invention to reduce aggregation. In one embodiment, a formulation of the invention comprises Polysorbate 20, Polysorbate 40, Polysorbate 60, or Polysorbate 80. Surfactants are particularly useful if a pump or plastic container is used to administer the formulation. The presence of a pharmaceutically acceptable surfactant mitigates the propensity for the protein to aggregate. The formulations may comprise a polysorbate which is at a concentration ranging from between about 0.001% to about 1%, or about 0.001% to about 0.1%, or about 0.01% to about 0.1%. In other specific embodiments, the formulations of the invention comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

The formulations of the compositions comprising a protein with a modulated glycosylation profile of the invention may optionally further comprise other common excipients and/or additives including, but not limited to, diluents, binders, stabilizers, lipophilic solvents, preservatives, adjuvants, or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the formulations of the invention at any suitable concentration such as between about 0.001% to about 5%, or any range or value therein. The concentration of preservative used in the formulations of the invention is a concentration sufficient to yield a microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", $21^{st}$ ed., Lippincott Williams & Wilkins, (2005), and in the "Physician's Desk Reference", $60^{th}$ ed., Medical Economics, Montvale, N.J. (2005). Pharmaceutically acceptable carriers can be routinely selected that are suitable for the mode of administration, solubility and/or stability of protein with a modulated glycosylation profile (e.g., an antibody or DVD-Ig), as well known those in the art or as described herein.

In one embodiment, the compositions comprising a protein with a modulated glycosylation profile of the invention are formulated with the same or similar excipients and buffers as are present in the commercial adalimumab (HUMIRA®) formulation, as described in the "Highlights of Prescribing Information" for HUMIRA® (adalimumab) Injection (Revised January 2008) the contents of which are hereby incorporated herein by reference. For example, each prefilled syringe of HUMIRA®, which is administered subcutaneously, delivers 0.8 mL (40 mg) of drug product to the subject. Each 0.8 mL of HUMIRA® contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for Injection, USP. Sodium hydroxide is added as necessary to adjust pH.

It will be understood by one skilled in the art that the formulations of the compositions comprising a protein with a modulated glycosylation profile of the invention may be isotonic with human blood, wherein the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonicity of the formulation. Tonicity modifiers suitable for this invention include, but are not limited to, saccharides, salts and amino acids.

In certain embodiments, the formulations of the compositions comprising a protein with a modulated glycosylation profile of the invention have an osmotic pressure from about 100 mOSm to about 1200 mOSm, or from about 200 mOSm to about 1000 mOSm, or from about 200 mOSm to about 800 mOSm, or from about 200 mOSm to about 600 mOSm, or from about 250 mOSm to about 500 mOSm, or from about 250 mOSm to about 400 mOSm, or from about 250 mOSm to about 350 mOSm.

The concentration of any one component or any combination of various components, of the formulations of the compositions comprising a protein with a modulated glycosylation profile of the invention is adjusted to achieve the desired tonicity of the final formulation. For example, the ratio of the carbohydrate excipient to protein with a modulated glycosylation profile (e.g., antibody or DVD-Ig) may be adjusted according to methods known in the art (e.g., U.S. Pat. No. 6,685,940). In certain embodiments, the molar ratio of the carbohydrate excipient to protein with a modulated glycosylation profile (e.g., antibody or DVD-Ig) may be from about 100 moles to about 1000 moles of carbohydrate excipient to about 1 mole of protein with a modulated glycosylation profile, or from about 200 moles to about 6000 moles of carbohydrate excipient to about 1 mole of protein with a modulated glycosylation profile, or from about 100 moles to about 510 moles of carbohydrate excipient to about 1 mole of protein with a modulated glycosylation profile, or from about 100 moles to about 600 moles of carbohydrate excipient to about 1 mole of protein with a modulated glycosylation profile.

The desired isotonicity of the final formulation may also be achieved by adjusting the salt concentration of the formulations. Pharmaceutically acceptable salts and those suitable for this invention as tonicity modifiers include, but are not limited to, sodium chloride, sodium succinate, sodium sulfate, potassium chloride, magnesium chloride, magnesium sulfate, and calcium chloride. In specific embodiments, formulations of the invention comprise NaCl, $MgCl_2$, and/or $CaCl_2$. In one embodiment, concentration of NaCl is between about 75 mM and about 150 mM. In another embodiment, concentration of $MgCl_2$ is between about 1 mM and about 100 mM. Pharmaceutically acceptable amino acids including those suitable for this invention as tonicity modifiers include, but are not limited to, proline, alanine, L-arginine, asparagine, L-aspartic acid, glycine, serine, lysine, and histidine.

In one embodiment the formulations of the compositions comprising a protein with a modulated glycosylation profile of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In certain specific embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

When used for in vivo administration, the formulations of the compositions comprising a protein with a modulated glycosylation profile of the invention should be sterile. The formulations of the invention may be sterilized by various sterilization methods, including sterile filtration, radiation, etc. In one embodiment, the protein with a modulated glycosylation profile (e.g., antibody or DVD-Ig) formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005). Formulations comprising proteins of interest (e.g., antibody or DVD-Ig.), such as those disclosed herein, ordinarily will be stored in lyophilized form or in solution. It is contemplated that sterile compositions comprising proteins of interest (e.g., antibody or DVD-Ig) are placed into a container having a sterile access port, for example, an intravenous solution bag or vial having an adapter that allows retrieval of the formulation, such as a stopper pierceable by a hypodermic injection needle. In one embodiment, a composition of the invention is provided as a pre-filled syringe.

In one embodiment, a formulation of the compositions comprising a protein with a modulated glycosylation profile of the invention is a lyophilized formulation. The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers.

A "lyoprotectant" is a molecule which, when combined with a protein with a modulated glycosylation profile (such as an antibody or DVD-Ig of the invention), significantly prevents or reduces chemical and/or physical instability of the protein upon lyophilization and subsequent storage. Lyoprotectants include, but are not limited to, sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; PLURONICS™; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, maltulose, iso-maltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

In one embodiment, the molar ratio of a lyoprotectant (e.g., trehalose) and protein with a modulated glycosylation profile (e.g., antibody or DVD-Ig) molecules of a formulation of the invention is at least about 10, at least about 50, at least about 100, at least about 200, or at least about 300. In another embodiment, the molar ratio of a lyoprotectant (e.g., trehalose) and protein with a modulated glycosylation profile molecules of a formulation of the invention is about 1, is about 2, is about 5, is about 10, about 50, about 100, about 200, or about 300.

A "reconstituted" formulation is one which has been prepared by dissolving a lyophilized protein with a modulated glycosylation profile (e.g., antibody or DVD-Ig) formulation in a diluent such that the protein with a modulated glycosylation profile is dispersed in the reconstituted formulation. The reconstituted formulation is suitable for administration (e.g., parenteral administration) to a patient to be treated with the protein with a modulated glycosylation profile and, in certain embodiments of the invention, may be one which is suitable for intravenous administration.

The "diluent" of interest herein is one which is pharmaceutically acceptable (safe and non-toxic for administration to a human) and is useful for the preparation of a liquid formulation, such as a formulation reconstituted after lyophilization. In some embodiments, diluents include, but are not limited to, sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

In certain embodiments, a formulation of the compositions comprising a protein with a modulated glycosylation profile of the invention is a lyophilized formulation comprising a protein with a modulated glycosylation profile (e.g., antibody or DVD-Ig) of the invention, wherein at least about 90%, at least about 95%, at least about 97%, at least about 98%, or at least about 99% of the protein with a modulated glycosylation profile may be recovered from a vial upon shaking the vial for 4 hours at a speed of 400 shakes per minute wherein the vial is filled to half of its volume with the formulation. In another embodiment, a formulation of the invention is a lyophilized formulation comprising a protein with a modulated glycosylation profile of the invention, wherein at least about 90%, at least about 95%, at least about 97%, at least about 98%, or at least about 99% of the protein with a modulated glycosylation profile may be recovered from a vial upon subjecting the formulation to three freeze/thaw cycles wherein the vial is filled to half of its volume with the formulation. In a further embodiment, a formulation of the invention is a lyophilized formulation comprising a protein with a modulated glycosylation profile of the invention, wherein at least about 90%, at least about 95%, at least about 97%, at least about 98%, or at least about 99% of the protein with a modulated glycosylation profile may be recovered by reconstituting a lyophilized cake generated from the formulation.

In one embodiment, a reconstituted liquid formulation may comprise a protein with a modulated glycosylation profile (e.g., antibody or DVD-Ig) of the invention at the same concentration as the pre-lyophilized liquid formulation.

In another embodiment, a reconstituted liquid formulation may comprise a protein with a modulated glycosylation profile (e.g., antibody or DVD-Ig) of the invention at a higher concentration than the pre-lyophilized liquid formulation, e.g., .about 2 fold, about 3 fold, about 4 fold, about 5 fold, about 6 fold, about 7 fold, about 8 fold, about 9 fold, or about 10 fold higher concentration of a protein with a modulated glycosylation profile than the pre-lyophilized liquid formulation.

In yet another embodiment, a reconstituted liquid formulation may comprise a protein with a modulated glycosylation profile (e.g., antibody or DVD-Ig) of the invention at a lower concentration than the pre-lyophilized liquid formulation, e.g., about 2 fold, about 3 fold, about 4 fold, about 5 fold, about 6 fold, about 7 fold, about 8 fold, about 9 fold or about 10 fold lower concentration of a protein with a modulated glycosylation profile than the pre-lyophilized liquid formulation.

The pharmaceutical formulations of the compositions comprising a protein with a modulated glycosylation profile, of the invention are typically stable formulations, e.g., stable at room temperature.

The terms "stability" and "stable" as used herein in the context of a formulation comprising a protein with a modulated glycosylation profile (e.g., an antibody or DVD-Ig) of the invention refer to the resistance of the protein in the formulation to aggregation, degradation or fragmentation under given manufacture, preparation, transportation and storage conditions. The "stable" formulations of the invention retain biological activity under given manufacture, preparation, transportation and storage conditions. The stability of the protein with a modulated glycosylation profile can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference formulation. For example, a reference formulation may be a reference standard frozen at −70° C. consisting of 10 mg/ml of a protein with a modulated glycosylation profile of the invention in PBS.

Therapeutic formulations of the compositions comprising a protein with a modulated glycosylation profile of the invention may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the protein with a modulated glycosylation profile (e.g., antibody or DVD-Ig) of the invention, and the particular therapeutic effect to be achieved, and (b) the limitations inherent in the art of compounding such a protein with a modulated glycosylation profile for the treatment of sensitivity in individuals.

Therapeutic compositions of the compositions comprising a protein with a modulated glycosylation profile of the invention, can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. By way of example, in certain embodiments, the proteins with modulated glycosylation profiles (including fragments of the protein with a modulated glycosylation profile) are formulated for intravenous administration. In certain other embodiments, the proteins with modulated glycosylation profiles (e.g., antibody or DVD-Ig), of the invention, including fragments of the proteins with modulated glycosylation profiles (e.g., antibody fragments) of the invention, are formulated for local delivery to the cardiovascular system, for example, via catheter, stent, wire, intramyocardial delivery, intrapericardial delivery, or intraendocardial delivery.

Formulations of the compositions comprising a protein with a modulated glycosylation profile of the invention, which are suitable for topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required (U.S. Pat. Nos. 7,378,110; 7,258,873; 7,135,180; 7,923,029; and US Publication No. 20040042972).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the compositions comprising a protein with a modulated glycosylation profile of the invention, may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In certain embodiments, the proteins with modulated glycosylation profiles (e.g., antibody or DVD-Ig) of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant Protein A receptor (Briscoe et al. (1995) *Am. J. Physiol.* 1233:134), different species of which may comprise the formulations of the invention, as well as components of the invented molecules; p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in another embodiment, the liposomes include a targeting moiety. In another embodiment, the therapeutic compounds in the liposomes are delivered by bolus injection to a site proximal to the desired area. When administered in this manner, the composition must be fluid to the extent that easy syringability exists. It must be stable under the conditions of manufacture and storage and may be preserved against the contaminating action of microorganisms such as bacteria and fungi. Additionally or alternatively, the proteins with modulated glycosylation profiles (e.g., antibodies or DVD-Igs) of the invention may be delivered locally to the brain to mitigate the risk that the blood brain barrier slows effective delivery.

In certain embodiments, the compositions comprising a protein with a modulated glycosylation profile of the invention may be administered with medical devices known in the art. For example, in certain embodiments a protein with a modulated glycosylation profile (e.g., antibody or DVD-Ig) or a fragment of protein with a modulated glycosylation profile (e.g., antibody fragment) is administered locally via a catheter, stent, wire, or the like. For example, in one embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The efficient dosages and the dosage regimens for the compositions comprising a protein with a modulated glycosylation profile of the invention depend on the disease or condition to be treated and can be determined by the persons skilled in the art. One of ordinary skill in the art would be able to determine such amounts based on such factors as the subject's size, the severity of the subject's symptoms, and the particular composition or route of administration selected.

VI. Kits and Articles of Manufacture Comprising the Compositions Comprising Proteins with Modulated Glycosylation Profiles of the Invention Also within the scope of the present invention are kits comprising the compositions comprising a protein with a modulated glycosylation profile, for example a protein such as an antibody, antigen-binding portion thereof, or a DVD-Ig, with a decreased fucosylation level or amount and/or an increased mannosylation level or amount of the invention and instructions for use. The term "kit" as used herein refers to a packaged product comprising components with which to administer the protein with a modulated glycosylation profile (e.g., antibody, or antigen-binding portion thereof, or DVD-Ig), of the invention for treatment of a disease or disorder. The kit may comprise a box or container that holds the components of the kit. The box or container is affixed with a label or a Food and Drug Administration approved protocol. The box or container holds components of the invention which may be contained within plastic, polyethylene, polypropylene, ethylene, or propylene vessels. The vessels can be capped-tubes or bottles. The kit can also include instructions for administering a protein with a modulated glycosylation profile (e.g., an antibody or a DVD-Ig) of the invention.

The kit can further contain one more additional reagents, such as an immunosuppressive reagent, a cytotoxic agent or a radiotoxic agent or one or more additional proteins of interest of the invention (e.g., an antibody having a complementary activity which binds to an epitope in the TNFα antigen distinct from a first anti-TNFα antibody). Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a liquid formulation or lyophilized formulation of a protein with a modulated glycosylation profile (e.g., an antibody, or antibody fragment thereof, or a DVD-Ig) of the invention. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a container filled with a liquid formulation of the invention is a pre-filled syringe. Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. No. 6,792,743, U.S. Pat. No. 5,607,400, U.S. Pat. No. 5,893,842, U.S. Pat. No. 7,081,107, U.S. Pat. No. 7,041,087, U.S. Pat. No. 5,989,227, U.S. Pat. No. 6,807,797, U.S. Pat. No. 6,142,976, U.S. Pat. No. 5,899,889, U.S. Pat. No. 7,699,811, U.S. Pat. No. 7,540,382, U.S. Pat. No. 7,998,120, U.S. Pat. No. 7,645,267, and US Patent Publication No. US20050075611. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a protein formulation stored in the syringe. For example, it is understood that silicon based lubricants deposited on the inside surface of the syringe chamber may affect particle formation in the protein formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

In certain embodiments, kits comprising a protein with a modulated glycosylation profile such as a decreased fucosylation level or amount and/or an increased mannosylation level or amount (e.g., an antibody or DVD-Ig) of the invention are also provided that are useful for various purposes, e.g., research and diagnostic including for purification or immunoprecipitation of a protein with a modulated glycosylation profile from cells, detection of the protein with a modulated glycosylation profile in vitro or in vivo. For isolation and purification of a protein with a modulated glycosylation profile, the kit may contain an antibody coupled to beads (e.g., sepharose beads). Kits may be provided which contain the antibodies for detection and quantitation of a protein with a modulated glycosylation profile in vitro, e.g., in an ELISA or a Western blot. As with the article of manufacture, the kit comprises a container and a label or package insert on or associated with the container. The container holds a composition comprising at least one protein with a modulated glycosylation profile (e.g., antibody or DVD-Ig) of the invention. Additional containers may be included that contain, e.g., diluents and buffers, control proteins with modulated glycosylation profiles (e.g., antibody or DVD-Ig). The label or package insert may provide a description of the composition as well as instructions for the intended in vitro or diagnostic use.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising a protein with a modulated glycosylation profile (e.g., an antibody or DVD-Ig) that is suitable for parenteral administration. In another embodiment, the unit dosage form is provided as a sterile lyophilized powder comprising a protein with a modulated glycosylation profile (e.g., an antibody or DVD-Ig) that is suitable for reconstitution.

In one embodiment, the unit dosage form is suitable for intravenous, intramuscular, intranasal, oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a pharmaceutical agent contained within the packaging material, wherein the pharmaceutical agent comprises a liquid formulation containing a protein with a modulated glycosylation profile (e.g., an antibody or DVD-Ig). The packaging material includes instruction means which indicate how that the protein with a modulated glycosylation profile (e.g., antibody or DVD-Ig) can be used to prevent, treat and/or manage one or more symptoms associated with a disease or disorder.

The present invention is further illustrated by the following examples which should not be construed as limiting.

EXAMPLES

Example 1

1. Materials & Methods

Cell Culture

Two recombinant Chinese Hamster Ovary (CHO) cell lines expressing two different humanized monoclonal antibodies (Antibody 1, Antibody 2) were evaluated in two different culture vessels (shaker flasks and laboratory scale bioreactors). Both cell lines were of CHO DUX-B11 origin based on a dhfr (dihydrofolate reductase) expression system. Both cell lines were cultured in the same chemically defined basal media (CDBM), with Cell Line 1 also utilizing a chemically-defined feed media (CDFM). Each of the respective media were supplemented with selected monosaccharides and oligosaccharides to evaluate their potential impact on the resulting N-glycan oligosaccharide profile. In preparing the cultures, the cell lines were serially expanded through separate seed train inoculums to generate enough cells for inoculation. Process conditions utilized during the cultures were slightly different between the two different cell lines as shown in Table 1, but similar between each cell line and the respective non-sugar supplemented control conditions.

TABLE 1

Summary of cell culture process conditions & sugar supplementation details

|  | Cell Line 1 | | | Cell Line 2 |
| --- | --- | --- | --- | --- |
| Culture Vessel | 250 mL shaker flask | 250 mL shaker flask | 3 L lab-scale bioreactors | 250 mL shaker flask |
| Culture Mode | Fedbatch | Fedbatch | Fedbatch | Semi-Batch[a] |
| Initial Culture Temperature (° C.) | 36 | 36 | 36 | 36 |
| Dissolved Oxygen (%) | N/A[b] | N/A[b] | 30 | N/A[b] |
| pH | N/A[b] | N/A[b] | 6.9 | N/A[b] |
| Sugar Supplements Evaluated[c] | Sucrose | Tagatose | Sucrose Tagatose | Sucrose |
| Supplement Concentrations (mM) | 0, 30, 50, 70 | 0, 30, 50, 70 | 0, 50 | 0, 7, 15, 30 |

[a]No feed media utilized; concentrated glucose solution addition utilized when glucose levels dropped below 3 g/L.
[b]Cultures run in CO₂ incubators at 5% $CO_2$ in air; pH and DO parameters were not controlled, and thus did not have setpoint values.
[c]Supplements added to both chemically-defined basal & feed media (when used).

Viable cell density (VCD) and cell viability values were measured through trypan blue exclusion via Cedex automated cell counters (Roche Applied Science, Indianapolis, Ind.), glucose and lactate values were measured with a ABL-805 (Radiometer Medical, Denmark) blood gas analyzer. Offline pH, dissolved oxygen (DO), and $pCO_2$ measurements were performed with a ABL-805 (Radiometer Medical, Denmark) blood gas analyzer. Osmolality was measured on a Multi-Osmette 2430 osmometer (Precision Systems, Natick, Mass.).

Protein A Affinity Chromatography

Antibody titers were measured from crude cell culture harvests on a Poros A™ (Life Technologies, Carlsbad, Calif.) affinity column using an Agilent (Santa Clara, Calif.) 1200 Series HPLC, or equivalent, operating with a low pH, step elution gradient with detection at 280 nm. Absolute concentrations were assigned with respect to reference standard calibration curves.

Purified antibodies subjected to additional analytical characterization were purified using MabSelect™ Protein A (GE Healthcare, Piscataway, N.J.) using a low pH, step elution gradient, followed by buffer exchange using Corning Lifesciences (Tewksbury, Mass.) Spin Concentrator X UF columns according to the manufacturers' recommended procedures.

N-Glycan Oligosaccharide Profiling

Approximately 200 μg of Protein A purified samples from Cell Lines 1 and 2 were treated with N-glycanase at 37° C. overnight to remove the N-glycans from the protein. The protein was precipitated and the supernatant was taken for subsequent chemical derivatization of the reducing end of the released glycans with 2-aminobenzamide (2-AB) dye. Following the derivatization step, the excess label was removed using clean up cartridges and the samples were analyzed using normal phase HPLC with fluorescent detection. Mobile phase A was 100% acetonitrile and mobile phase B was 50 mM ammonium formate pH 4.4. The glycans were eluted from a polyamide column (Prozyme, Hayward, Calif.) using a shallow gradient. The labeled glycans were detected using a fluorescence detector with an excitation wavelength of 330 nm and an emission wavelength of 420 nm.

2. Results

Shake Flask Screening of Select Monosaccharides and Oligosaccharides

Cell Line 1 was cultured in shake flasks in fedbatch mode after an abbreviated seed train. Sucrose and tagatose were supplemented into chemically-defined basal and feed media at concentrations of 30, 50, and 70 mM, and compared to an unsupplemented control condition. The viable cell density (VCD), viability, and harvest titer results are shown in FIGS. 3A-3C and FIGS. 5A-5C for the sucrose, and tagatose conditions, respectively. Both sugars facilitated a slight decrease in VCD, with the higher concentrations also supporting the lowest peak VCD. Viability results were however more comparable to the control, unsupplemented conditions, with the exception of the 70 mM sucrose condition, which resulted in a decrease in cell viability that was larger, and earlier in the culture, compared to control conditions. Harvest titer results demonstrated that 30 mM and 50 mM sucrose did not adversely impact titer, but 70 mM sucrose did reduce the harvest titer significantly. 30 mM tagatose did not adversely impact harvest titer, but 50 mM and 70 mM tagatose did. Collectively, these results indicate that at certain concentrations of sucrose (e.g., 30 mM and 50 mM) and tagatose (e.g., 30 mM) there is a decrease in viable cell density, however percent cell viability and harvest titer profile remain comparable to unsupplemented culture conditions. As such, the upper threshold of sucrose or tagatose concentration should not be exceeded.

Figure 2:
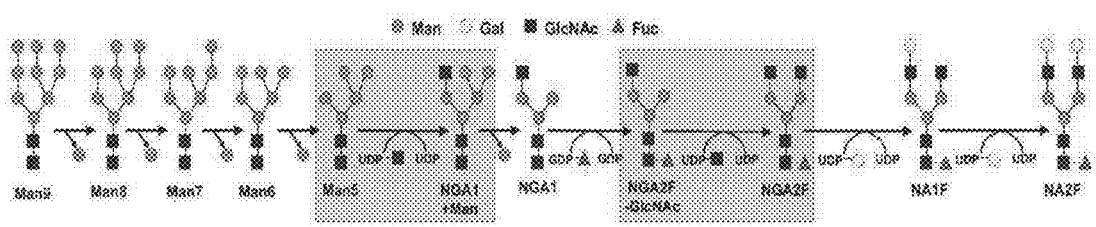
FIG. 2 depicts a simplified linear reaction view of the N-glycan biosynthetic pathway in mammalian cells.
Figure 3A:
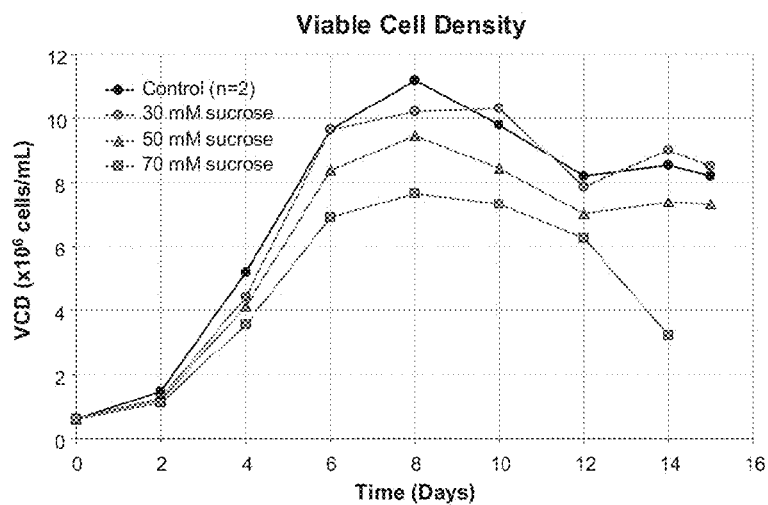
FIGS. 3A-3C depict the cell culture performance of Cell Line 1 in media supplemented with 30 mM, 50 mM or 70 mM sucrose.
Figure 3B:
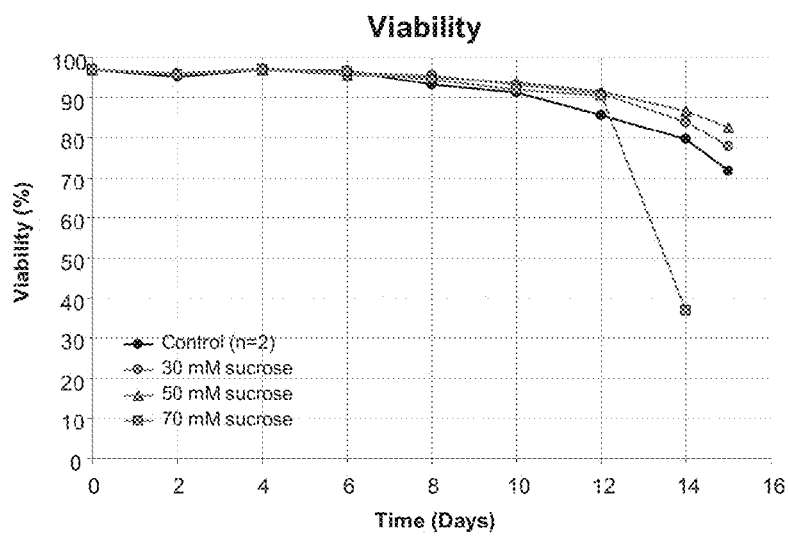
Figure 3C:
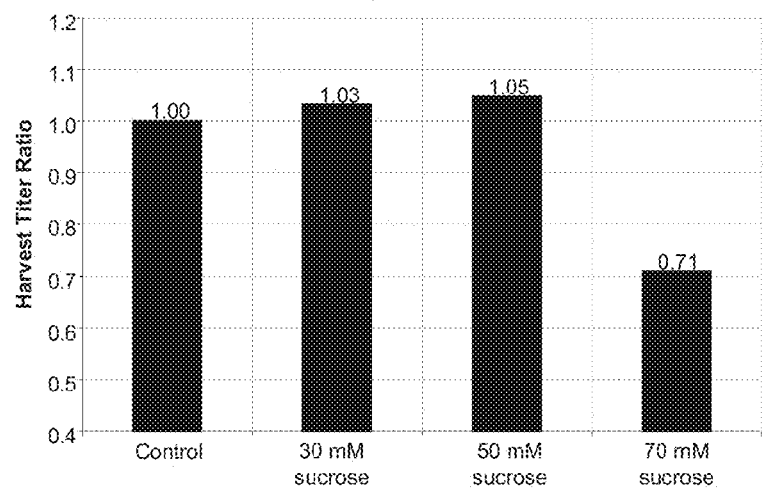
Figure 4:
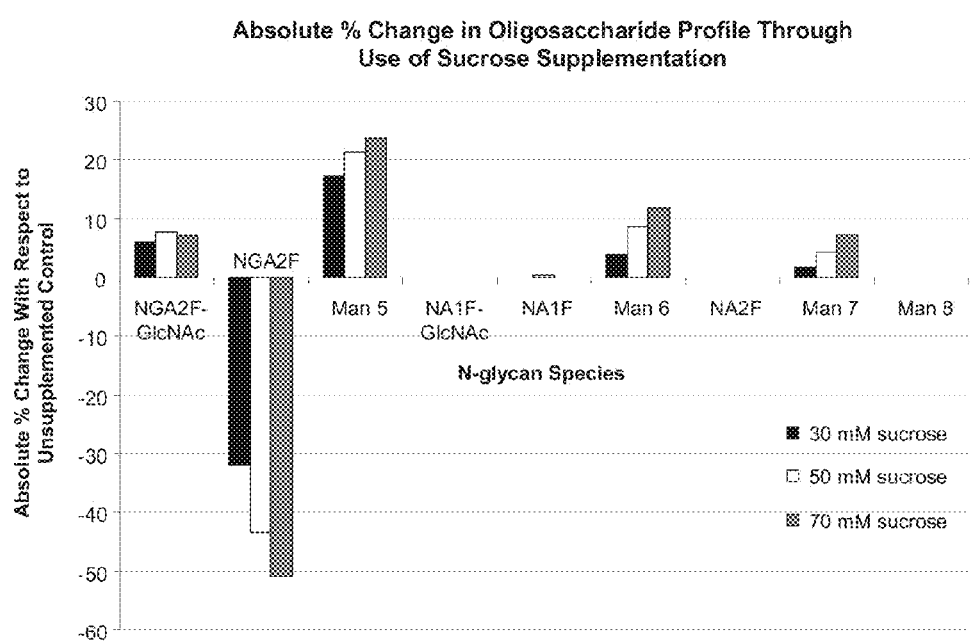
FIG. 4 depicts the N-glycan oligosaccharide results as an absolute percent change in oligosaccharide profile of Cell Line 1 in media supplemented with 30 mM, 50 mM or 70 mM sucrose.
Figure 5A:
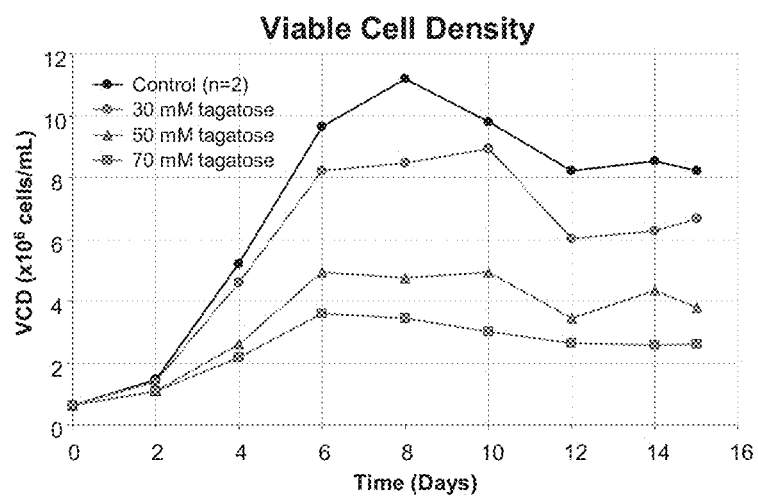
FIGS. 5A-5C depict the cell culture performance of Cell Line 1 in media supplemented with 30 mM, 50 mM or 70 mM tagatose.
Figure 5B:
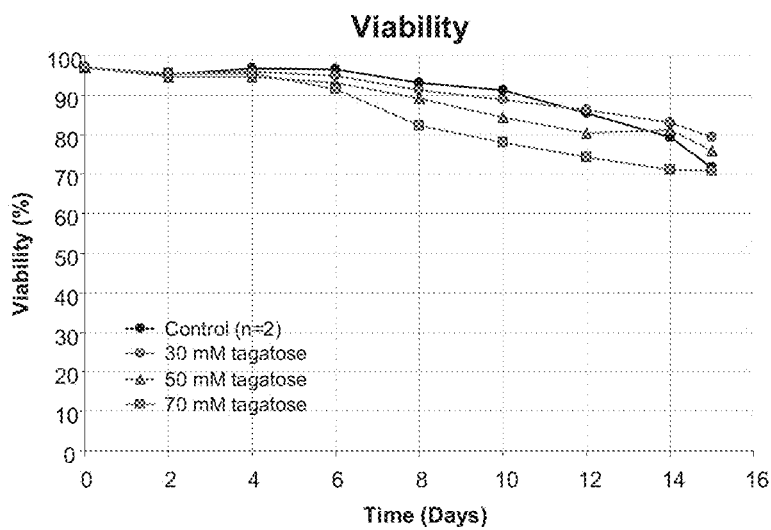
Figure 5C:
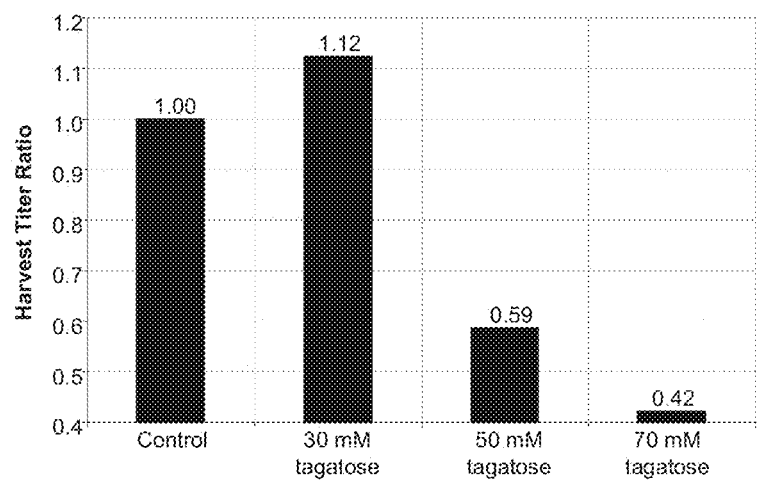

There was a significant impact on the overall N-glycan distribution when cell cultures were supplemented with sucrose (FIG. 4). A concentration-dependent response was observed across all sucrose concentrations evaluated. Notably there was a 24% increase in Man 5 species, 12% increase in Man 6 species, and a 7% increase in Man 7 species at the 70 mM sucrose supplementation condition. This cumulative increase of 43% in overall mannosylated N-glycans was accompanied by a 51% drop in NGA2F species, the majority of which was precluded from being formed due to the abrogation of the N-glycan biosynthetic reaction as shown in FIG. 2. The data also demonstrate that combining the 51% decrease in NGA2F species and the 7% increase in NGA2F-GlcNAc species results in an overall decrease in the fucosylation level of 44%. This significant drop in fucosylation is important as it has been shown that decreased fucosylation of N-glycans has a significant and positive effect on the overall level of ADCC response. These data demonstrate that the supplementation of sucrose into cell culture media is capable of significantly re-distributing the overall protein glycosylation profile of the produced protein, and for some commercial protein therapeutics, this is a desired product quality attribute.

Figure 6:
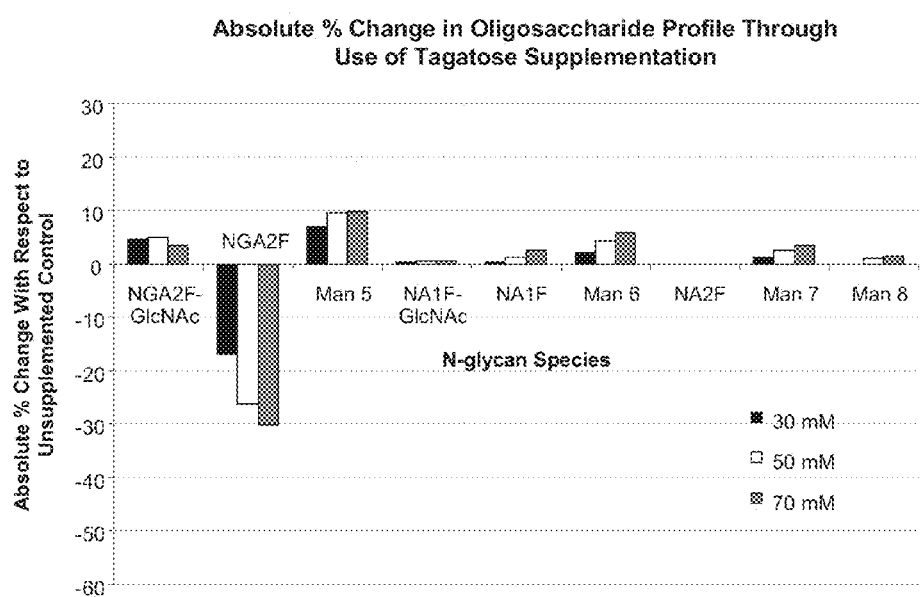
FIG. 6 depicts the N-glycan oligosaccharide results as an absolute percent change in oligosaccharide profile of Cell Line 1 in media supplemented with 30 mM, 50 mM or 70 mM tagatose.
Figure 7A:
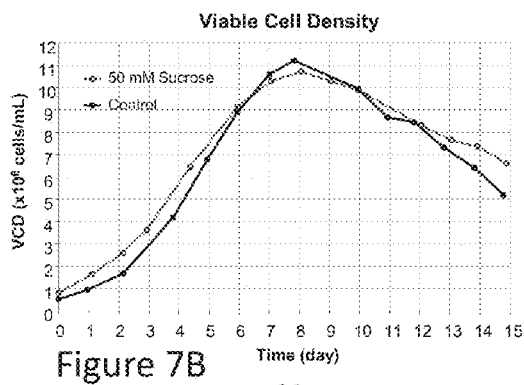
FIGS. 7A-7F depict the cell culture performance of Cell Line 1 in laboratory-scale bioreactors with media supplemented with 50 mM sucrose.
Figure 7B:
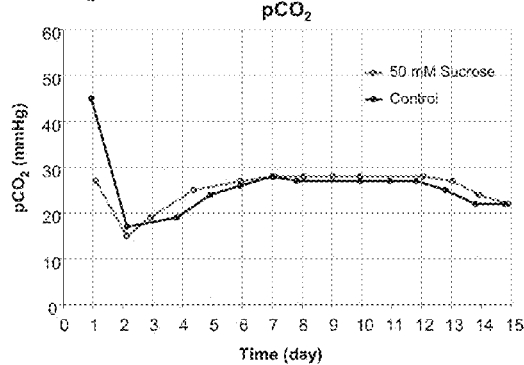
Figure 7C:
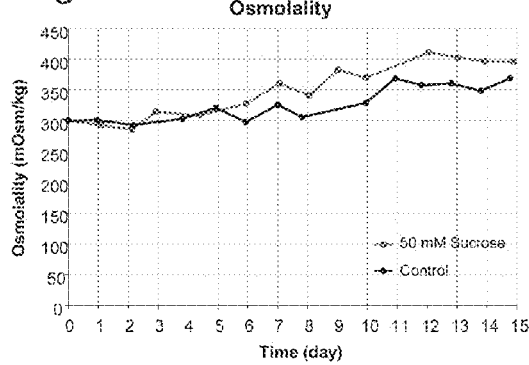
Figure 7D:
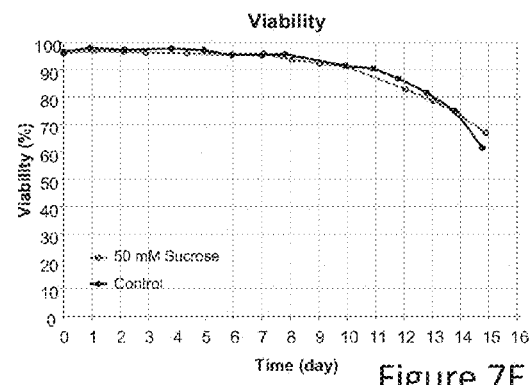
Figure 7E:
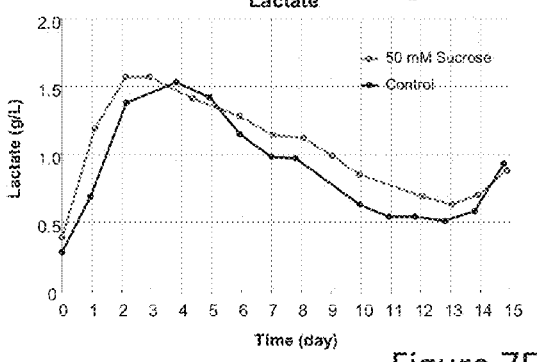
Figure 7F:
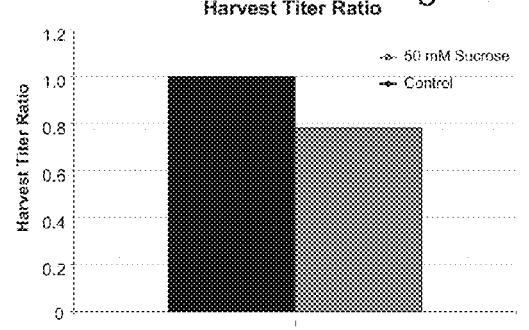

There was also a significant impact on the overall N-glycan distribution when the cell culture media was supplemented with tagatose (FIG. 6). Similar to the sucrose supplemented cell culture conditions, there was a concentration-dependent response across all of the concentrations evaluated. The results indicate that there was at most a 10% increase in Man 5 species, 6% increase in Man 6 species, 3% increase in Man 7 species, and a 1% increase in Man 8 species at the 70 mM tagatose supplementation condition. This cumulative 20% increase in overall mannosylated N-glycans was accompanied by a 30% decrease in NGA2F species. In addition, there was an overall 23% decrease in overall fucosylation levels. Comparison of the results of sucrose and tagatose supplementation demonstrate that the percent increase of N-glycans was lower in the tagatose supplemented cultures as compared to the sucrose supplemented cultures. However, the individual N-glycan species which were modulated, were similar between the sucrose and tagatose supplemented cultures. Both sugars utilize the same mechanism to modulate the protein N-glycosylation profile as the pattern of modulation of the individual N-glycans species was consistent between both sugars.

Laboratory-Scale Bioreactor Confirmation of the Targeted Modulation of Protein Glycosylation Profiles 3 L scale-down model bioreactors were utilized to verify the impact of select sugars on the resulting protein glycosylation profiles. The concentration of the sucrose and tagatose was chosen to minimize any potential adverse impact on cell growth and productivity, but still facilitate a measurable modulation of the glycosylation profile. Cell culture process performance indicators were monitored and measured throughout the respective cultures. Viable cell density, cell viability, lactate, $pCO_2$, osmolality, harvest titer, and harvest N-glycan oligosaccharide data were measured and reported.

Figure 8:
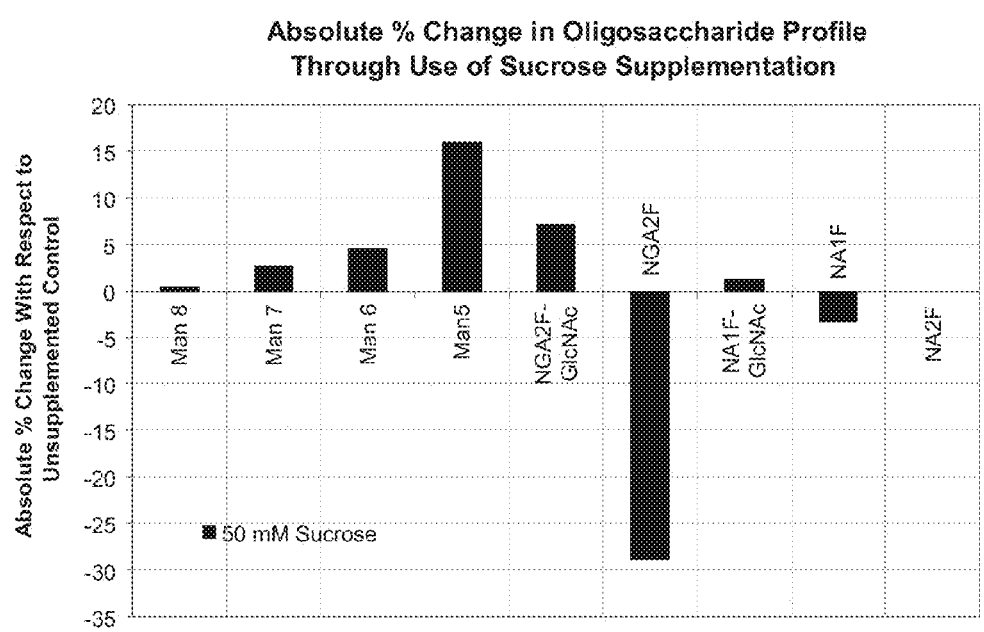
FIG. 8 depicts the N-glycan oligosaccharide results as an absolute percent change in oligosaccharide profile of Cell Line 1 in laboratory-scale bioreactors with media supplemented with 50 mM sucrose.
Figure 9A:
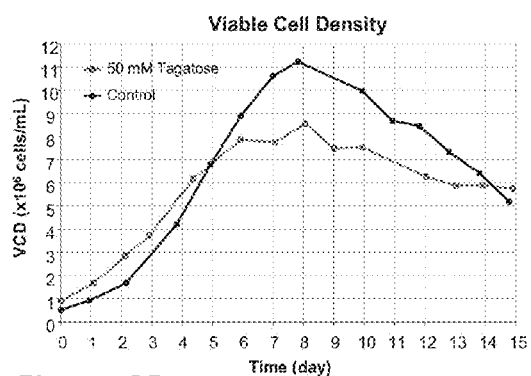
FIGS. 9A-9F depict the cell culture performance of Cell Line 1 in laboratory-scale bioreactors with media supplemented with 50 mM tagatose.
Figure 9D:
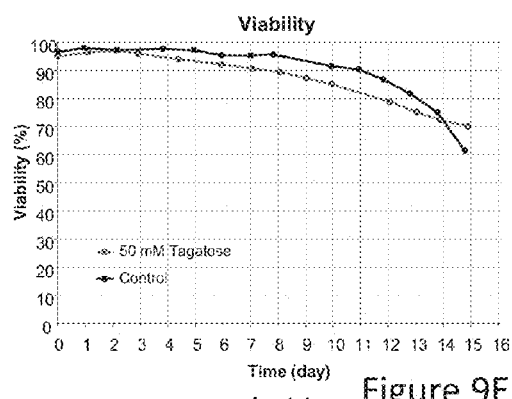
Figure 9B:
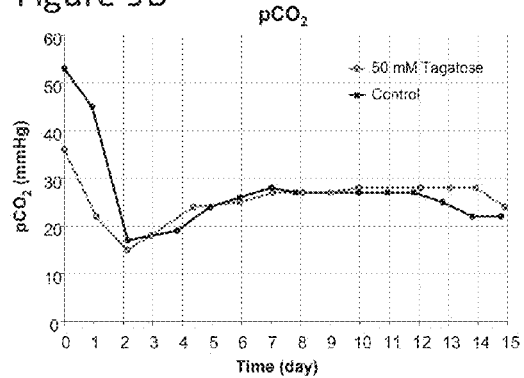
Figure 9E:
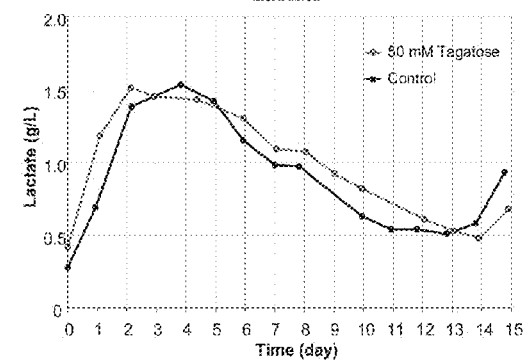
Figure 9C:
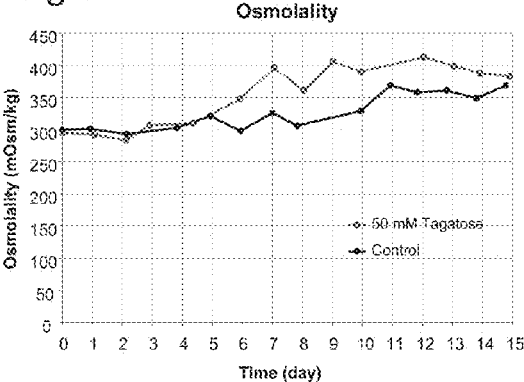
Figure 9F:
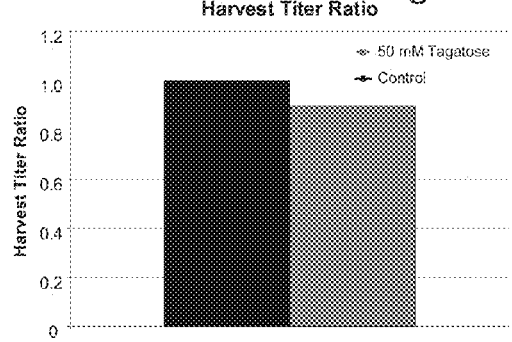

FIGS. 7A-7F highlight the cell culture performance results observed through the use of sucrose supplementation in the basal and feed medias. In laboratory-scale bioreactors there was no impact on viable cell density or cell viability upon supplementation with 50 mM sucrose when compared to the unsupplemented control condition. Dissolved $CO_2$ ($pCO_2$) and lactate production are direct measures of the respiratory and metabolic activities of mammalian cells, respectively. There was no significant difference in $pCO_2$ between the sucrose supplemented and non-supplemented cultures, indicating no net change in the overall respiratory activity of the cells. With respect to lactate, there was only a nominal increase in overall levels throughout the sucrose supplemented culture, which is consistent with the overall higher level of residual sugar in the culture media. Osmolality of the sucrose supplemented condition was only slightly higher compared to the control mostly due to the additional sugar solute. Upon harvest of the cultures, the final titer ratio of the sucrose supplemented culture was 0.78 suggesting a slight drop in overall antibody productivity with inclusion of 50 mM sucrose. These data are consistent with the results observed from the shake flask cultures. After Protein A purification, the N-glycan glycoform profile was measured (FIG. 8). Similar to the shake flask results, there was a significant increase in overall mannosylation levels; Man 7 increased 3%, Man 6 increased 5%, and Man 5 increased 16%. This 24% increase in overall mannosylation was accompanied by a 29% decrease in NGA2F species, and an overall 24% decrease in fucosylation. These changes are very significant and are consistent with the results observed in the shake flasks.

FIGS. 9A-9F highlight the cell culture results observed with the use of tagatose supplementation in the basal and feed medias. Tagatose had a much more pronounced effect on viable cell density as compared to the unsupplemented control. The results indicated a significant reduction in peak VCD from $11.2 \times 10^6$ cells/mL for the control unsupplemented culture versus $8.5 \times 10^6$ cells/mL for the tagatose supplemented culture. Despite this lower cell growth, cell viability remained high throughout the culture, and comparable to the results observed in the control culture. There was no significant difference in $pCO_2$ between the tagatose supplemented and non-supplemented cultures, suggesting no net change in the overall respiratory activity of the cells. With respect to lactate, there was only a nominal increase in overall levels throughout the tagatose supplemented culture, which is consistent with the overall higher level of residual sugar in the culture media. Osmolality of the tagatose supplemented culture was higher as compared to the control culture mostly due to the additional sugar solute. Upon harvest of the cultures, the final titer ratio of the tagatose supplemented culture was 0.90 suggesting a slight drop in overall antibody productivity upon inclusion of 50 mM tagatose. The results were consistent with the results observed from the shake flask cultures. The final harvest titer ratio of the tagatose supplemented cultures was higher than the final harvest titer ratio observed from the sucrose supplemented culture.

Figure 10:
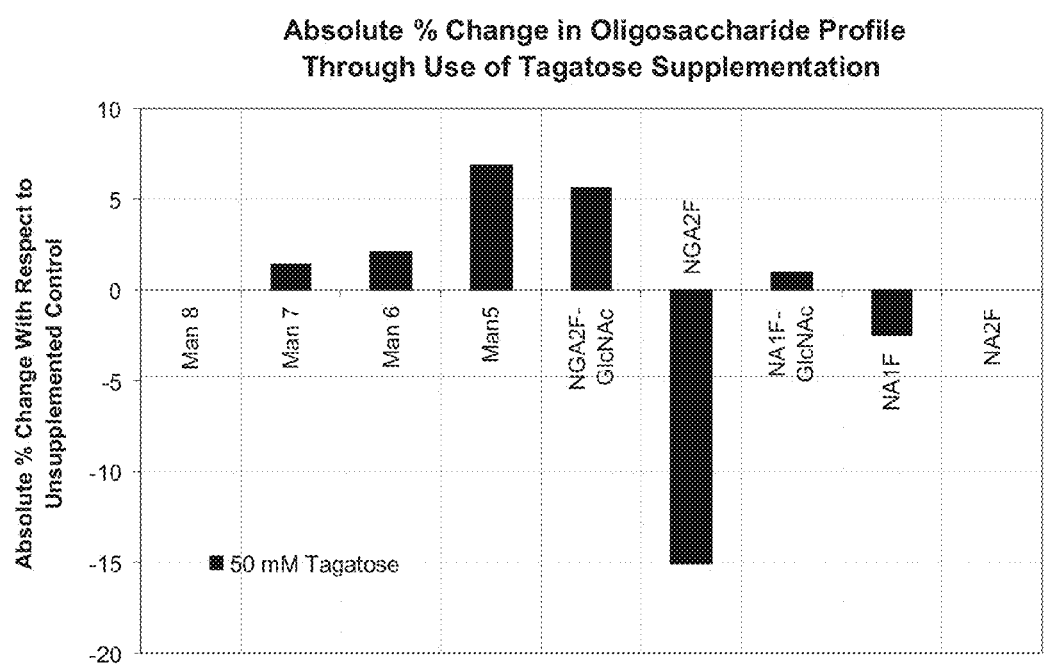
FIG. 10 depicts the N-glycan oligosaccharide results as an absolute percent change in oligosaccharide profile of Cell Line 1 in laboratory-scale bioreactors with media supplemented with 50 mM tagatose.

After Protein A purification, the N-glycan glycosylation profile was measured with the results shown in FIG. 10. Similar to the shake flask results, there was a significant increase in overall mannosylation levels; Man 7 increased 1%, Man 6 increased 2%, and Man 5 increased 7%. This 10% increase in overall mannosylation was accompanied by a 15% decrease in NGA2F species, and an overall 11% decrease in fucosylation. These changes are very significant and are consistent with the results observed in the shake flasks.

The cell culture process performance results in 3 L-scale bioreactors demonstrated that the observed effect on protein glycosylation in shake flasks is scale-independent. The significant increase in mannosylation, and resulting decrease in fucosylation has important implications for the optimization of the production of protein therapeutics and the modulation of protein glycosylation profiles. Indeed, the selective use of sugars such as sucrose and tagatose increases the ability of cell culture scientists to customize the product characteristics of recombinant glycoproteins expressed in mammalian cells, and the resulting therapeutic activity, efficacy, and PK.

Figure 11A:
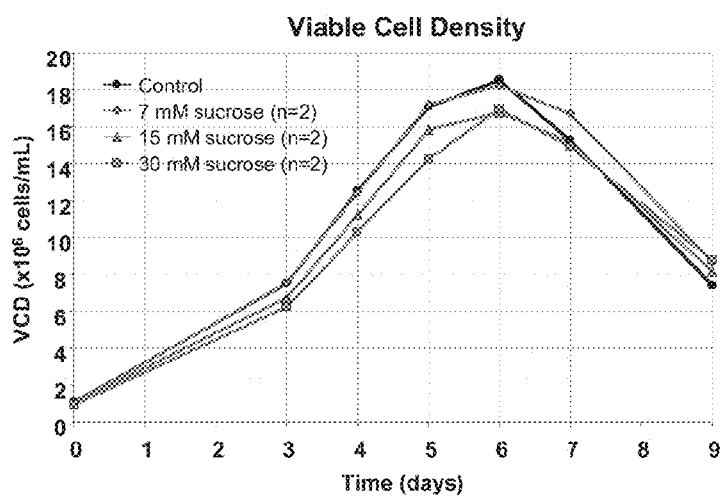
FIGS. 11A-11C depict the cell culture performance of Cell Line 2 in media supplemented with 7 mM, 15 mM or 30 mM sucrose.
Figure 11B:
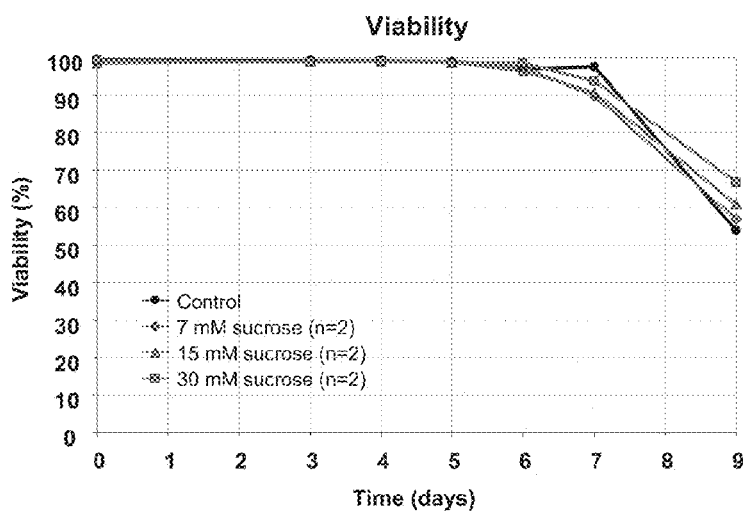
Figure 11C:
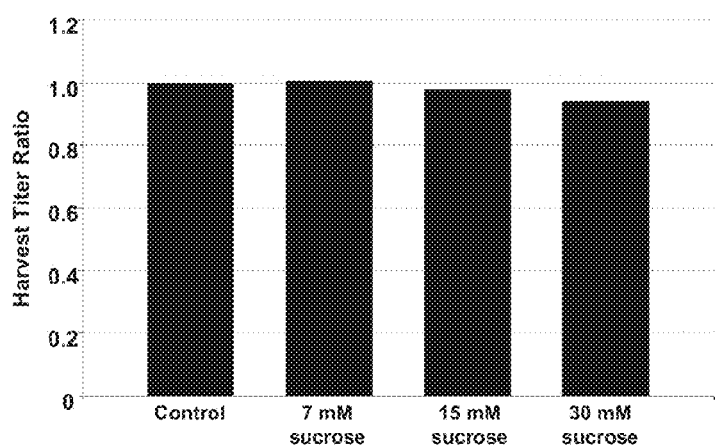
Figure 12:
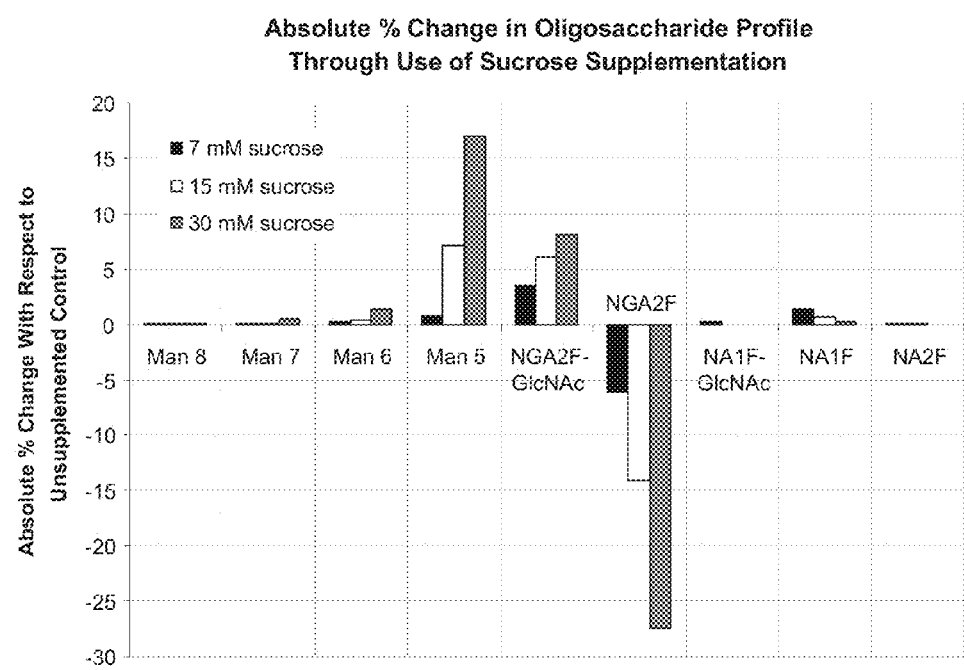
FIG. 12 depicts the N-glycan oligosaccharide results as an absolute percent change in oligosaccharide profile of Cell Line 2 in media supplemented with 7 mM, 15 mM or 30 mM sucrose.

Evaluation of Alternative Cell Lines for the Impact of Selective Sugar Supplementation on the Resulting Protein Glycosylation Profiles Cell Line 2 was evaluated in shake flask culture in semi-fedbatch mode. Sucrose was supplemented into the basal media at various concentrations to evaluate the resulting impact on cell culture performance, as well as the protein glycosylation profile. The viable cell density, viability, and harvest titer results are shown in FIGS. 11A-11C. On average, 7 mM, 15 mM, and 30 mM sucrose all nominally impacted overall cell growth, with only slight drops in peak viable cell density ($1 \times 10^6$-$2 \times 10^6$ cells/mL) as compared to the unsupplemented control. Cell viability and harvest titer results were not significantly different from each other. These results are consistent with the lower concentration sucrose supplementation results generated using Cell Line 1, in that at certain concentrations, there is no significant impact on overall cell growth or productivity. There was however, a very significant impact on the protein glycosylation profiles of harvest samples across all sucrose concentrations evaluated (FIG. 12). A concentration-dependent modulation of protein glycosylation was observed that was consistent with the results obtained for Cell Line 1.

Notably there was up to a 17% increase in Man 5 species, 1% increase in Man 6 species, and a 1% increase in Man 7 species at the 30 mM sucrose supplementation condition. This cumulative increase of 19% in overall mannosylated N-glycans was accompanied by a 27% drop in NGA2F species, and a 19% drop in overall fucosylation. Hence, as demonstrated with Cell Line 1, there was a very significant impact on the N-glycan glycoform profile. Specifically, individual N-glycans increased or decreased with sucrose supplementation of Cell Line 2 that was consistent with the results obtained for Cell Line 1.

Example 2

1. Materials & Methods

Cell Culture

Two recombinant Chinese Hamster Ovary (CHO) cell lines expressing two different recombinant glycoproteins were evaluated in two different cultures vessels (shaker flasks and 3 L laboratory scale bioreactors). Cell Line 1 expressed Antibody 1, Cell Line 2 expressed Dual Variable Domain Immunoglobulin 1 (DVD 1) and Cell Line 3 expressed Antibody 2. Antibodies 1 and 2 are IgG1 proteins, and DVD 1 is an immunoglobulin with two variable domains as documented previously (Wu C. et al., (2007) Nat. Biotechnol 25(11):1290-1297). All cell lines were of CHO DUX-B11 origin based on a dhfr (dihydrofolate reductase) expression system. All cell lines were cultured in the same chemically defined basal media. Cell lines 1 and 2 were fed with the same chemically-defined feed media, but Cell Line 1 was fed media that was formulated at a 50% higher concentration. Each of the respective media were supplemented with either sucrose or tagatose to evaluate their potential impact on the resulting N-glycan oligosaccharide profile. All sugars were purchased from Sigma-Aldrich (St. Louis, Mo.). In preparation of the cultures, the cell lines were serially expanded through separate seed train inoculums to generate enough cells for inoculation. Process conditions utilized during the cultures were slightly different between the two different cell lines as shown in Table 1, but similar between each cell line and the respective sugar supplemented control conditions.

TABLE 2

Summary of cell culture process conditions and sugar supplementation details

| | Cell Line 1 | | Cell Line 2 | Cell Line 3 |
|---|---|---|---|---|
| Culture Vessel | 250 mL shaker flask | 3 L lab-scale bioreactors | 250 mL shaker flask | 250 mL shaker flask |
| Culture Mode | Fedbatch | Fedbatch | Fedbatch | Extended Batch[a] |
| Initial Culture Temperature (° C.) | 36 | 36 | 35 | 36 |
| Dissolved Oxygen (%) | N/A[b] | 30 | N/A[b] | N/A[b] |
| pH | N/A[b] | 6.9 | N/A[b] | N/A[b] |
| Sugar Supplements Evaluated[b] | Sucrose Tagatose | Sucrose Tagatose Fructose | Sucrose Tagatose | Sucrose |
| Supplement Concentrations (mM)[c] | 0, 1, 10, 30, 50, 70 | 0, 50 | 0, 1, 30, 50 | 0, 7, 15, 30 |

[a]No feed media used; glucose added to cultures as needed to preclude glucose depletion.
[b]Cultures run in CO2 incubators at 5% CO2 in air; pH and DO parameters were not controlled, and thus do not have setpoint values.
[c]Supplements added to both chemically-defined basal and feed media.

Viable cell density (VCD) and cell viability values were measured through trypan blue exclusion via Cedex automated cell counters (Roche Applied Science, Indianapolis, Ind.), glucose and lactate values were measured with a ABL-805 (Radiometer Medical, Denmark) blood gas analyzer. Offline pH, dissolved oxygen (DO), and $pCO_2$ measurements were performed with an ABL-805 (Radiometer Medical, Denmark) blood gas analyzer. Osmolality was measured on a Multi-Osmette 2430 osmometer (Precision Systems, Natick, Mass.).

Protein A Affinity Chromatography

Antibody titers were measured from crude cell culture harvests on a Poros A™ (Life Technologies, Carlsbad, Calif.) affinity column using an Agilent (Santa Clara, Calif.) 1200 Series HPLC, or equivalent, operating with a low pH, step elution gradient with detection at 280 nm. Absolute concentrations were assigned with respect to reference standard calibration curves.

Purified antibodies subjected to additional analytical characterization were purified using MabSelect™ Protein A (GE Healthcare, Piscataway, N.J.) using a low pH, step elution gradient, followed by buffer exchange using Corning Lifesciences (Tewksbury, Mass.) Spin Concentrator X UF columns according to the manufacturers' recommended procedures.

N-Glycan Oligosaccharide Profiling

Approximately 200 μg of Protein A purified samples from Cell Lines 1 and 2 were treated with N-glycanase at 37° C. overnight to remove the N-glycans from the protein. The protein was precipitated and the supernatant was taken for subsequent chemical derivatization of the reducing end of the released glycans with 2-aminobenzamide (2-AB) dye. Following the derivatization step, the excess label was removed using clean up cartridges and the samples were analyzed using normal phase HPLC with fluorescent detection. Mobile phase A was 100% acetonitrile and mobile phase B was 50 mM ammonium formate pH 4.4. The glycans were eluted from a polyamide column (Prozyme, Hayward, Calif.) using a shallow gradient. The labeled glycans were detected using a fluorescence detector with an excitation wavelength of 330 nm and an emission wavelength of 420 nm.

ADCC Measurements

ADCC activity was assessed using a $^{51}$Cr release assay. Approximately 1 million cells expressing the target for Antibody 2 were labeled with 50 μCi $^{51}$Cr for 1 hour at 37° C., washed with culture medium, and then plated at 1×10$^4$/well in a 96-well v-bottom plate. Antibody 2 was incubated with target cells for 30 minutes at 4° C. before addition of PBMC effector cells. After a 4 hour incubation at 37° C., 100 μL of supernatant were collected from each well, and released radioactivity was counted with a Wallac WIZARD Gamma Counter (Perkin-Elmer). All measurements were expressed as a percentage of total cell lysis.

Statistics

Experimental results are expressed as mean±SD for those results generated from at least three independent cultures. Experimental results are expressed as the measured value for those results generated from less than three independent cultures. Results were evaluated for statistical significance through 2-sided t-tests, with a requirement of $p<0.05$ relative to the unsupplemented control conditions.

2. Results

Figure 13A:
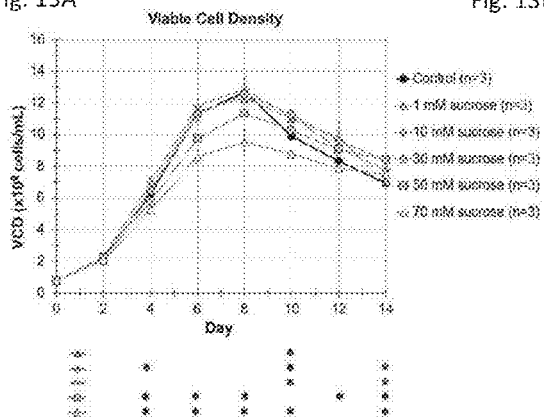
FIGS. 13A-13D depict the cell culture performance of Cell Line 1 in media supplemented with 1 mM, 10 mM, 30 mM, 50 mM or 70 mM sucrose.
Figure 13B:
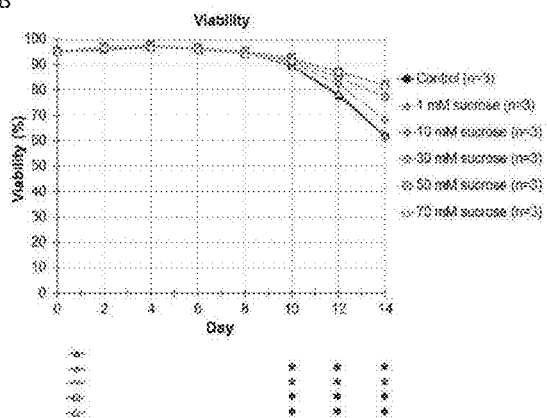
Figure 13C:
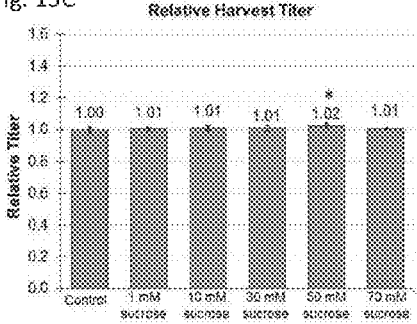
Figure 14A:
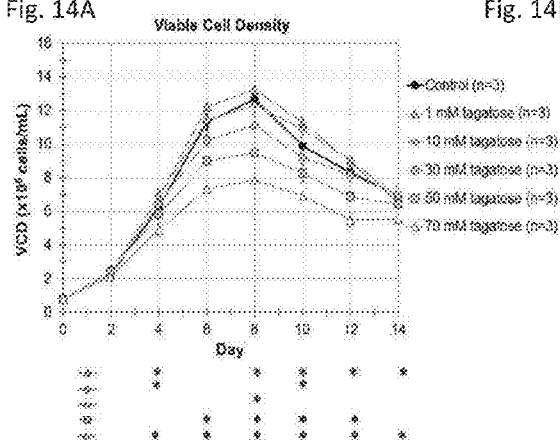
FIGS. 14A-14D depict the cell culture performance of Cell Line 1 in media supplemented with 1 mM, 10 mM, 30 mM, 50 mM or 70 mM tagatose.
Figure 14B:
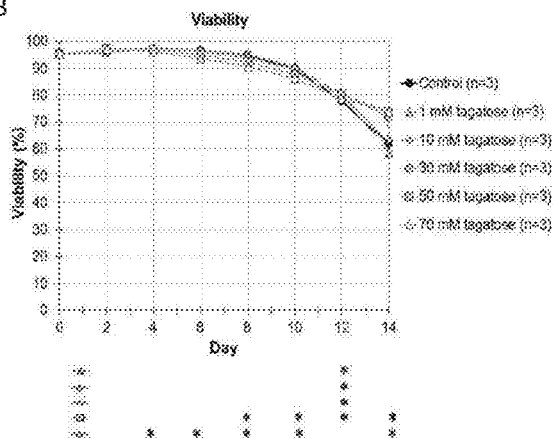
Figure 14C:
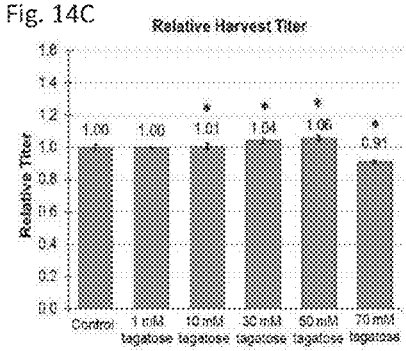

Impact of Sucrose and Tagatose on the Protein Glycosylation Profiles of Recombinant Antibodies Cell Line 1 was cultured in shake flasks in fedbatch mode after an abbreviated seed train. Sucrose and tagatose were supplemented into chemically-defined basal and feed media at concentrations of 1, 10, 30, 50, and 70 mM, and compared to unsupplemented control conditions. The viable cell density (VCD), viability, and harvest titer results are shown in FIGS. 13A-13C for the sucrose supplemented cultures and FIGS. 14A-14C for the tagatose supplemented cultures.

Amongst the sucrose supplemented cultures, viable cell density remained essentially the same over time across the 1, 10, and 30 mM sucrose conditions. Only the 50 mM and 70 mM sucrose cultures demonstrated a reduction in peak VCD, which were modest changes, but statistically significant. Cell viability results were similar across the various conditions up to process day 10. After process day 10, the 10, 30, 50, and 70 mM sucrose cultures all died slower than the control, and the results were statistically significant. It is likely that the higher sugar concentration in these cultures was responsible for the prolonged cell viability. Despite these changes in VCD and viability, the Antibody 1 harvest titer results were essentially indistinguishable from the control conditions. Only the 50 mM sucrose conditions demonstrated a 2% increase in harvest titer. Thus, across the range of tested concentrations, sucrose is well tolerated by mammalian cells in culture, with only a minor impact on cell growth, and no impact on protein productivity.

Figure 13D:
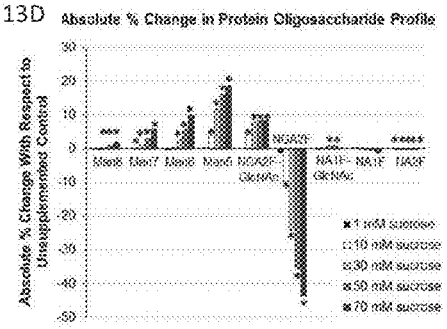

The impact of sucrose on the N-glycan oligosaccharide distribution is shown in FIG. 13D. There was a significant impact on the overall N-glycan distribution. A concentration-dependent response was observed across all the sucrose concentrations evaluated. Notably there was a 19% increase in Man 5 species, 10% increase in Man 6 species, 6% increase in Man 7 species, and 2% increase in Man 8 species for the 70 mM sucrose supplementation condition. This cumulative increase of 37% in overall mannosylated N-glycans was accompanied by a 44% drop in NGA2F species, the majority of which was precluded from being formed due to the abrogation of the N-glycan biosynthetic reaction shown in FIG. 2. The data also demonstrate that the 44% decrease in NGA2F species, combined with a 1% decrease in NA1F species, and an 8% increase in NGA2F-GlcNAc species, resulted in an overall decrease in the fucosylation level of 37%. The 10, 30, and 50 mM sucrose cultures demonstrated similar behavior, but with lower absolute percent changes. However, the overall N-glycan core fucosylation was decreased in a statistically significant manner at 10, 30, 50 and 70 mM sucrose, which is beneficial for some recombinant proteins. The results also establish that sucrose supplementation is a new powerful method for the redistribution of N-glycans towards high mannose glycans, which is a desirable product characteristic for some protein therapeutics.

Amongst the tagatose supplemented cultures, viable cell density remained similar or higher over time across the 1 mM and 10 mM conditions. However, the 30, 50, and 70 mM tagatose cultures demonstrated a reduction in peak VCD across many process days which was statistically significant. Similar to the sucrose supplementation results, cell viability remained high throughout each of the tagatose supplemented cultures. The lower concentrations of 1 mM and 10 mM behaved in a manner similar to the control cultures. After process day 10, the 30, 50, and 70 mM tagatose cultures all died slower than the control and the results were statistically significant across many of the days. It is likely that the higher sugar concentration in these cultures was responsible for the higher cell viability. Despite these changes in VCD and viability, the Antibody 1 harvest titer results were essentially indistinguishable from the cells cultured under control conditions. Only the 70 mM tagatose conditions demonstrated a 9% decrease in harvest titer. Thus, across the range of tested concentrations it can be concluded that tagatose is well tolerated by mammalian cells in culture, with only a minor impact on cell growth and protein productivity.

Figure 14D:
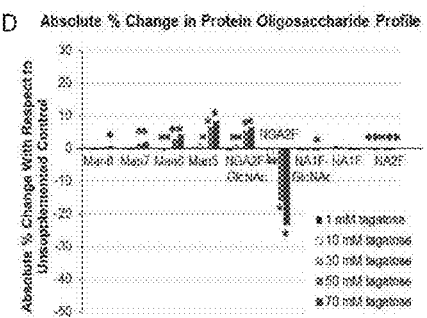

The impact of tagatose on the N-glycan oligosaccharide distribution is shown in FIG. 14D. There was a significant impact on the overall N-glycan distribution. A concentration-dependent response was observed across many of the tagatose concentrations evaluated. Notably there was an 8% increase in Man 5 species, 4% increase in Man 6 species, 2% increase in Man 7 species, and 1% increase in Man 8 species for the 70 mM tagatose supplementation condition. This cumulative increase of 15% in overall mannosylated N-glycans was accompanied by a 23% drop in NGA2F species, the majority of which was precluded from being formed due to the abrogation of the N-glycan biosynthetic reaction shown in FIG. 2. The data also demonstrate that the 23% decrease in NGA2F species, combined with a 8% increase in NGA2F-GlcNAc species, resulted in an overall decrease in the fucosylation level of 15%. The 50 mM tagatose cultures demonstrated similar behavior, but with lower absolute percent changes. The 1, 10, and 30 mM tagatose cultures provided for N-glycan profiles that were not practically different compared to the control culture. The results obtained with tagatose supplementation of cell culture media are similar to the results obtained with sucrose supplementation. Supplementation of cell culture media with tagatose results in an overall decrease in core N-glycan fucosylation with potential benefits towards ADCC, and provides a novel method for the modulation of N-glycan species, as well as a method for achieving product comparability with a reference protein.

Comparison of the results of sucrose or tagatose supplementation demonstrates that the extent of change in the percent of N-glycans was lower in tagatose supplemented cultures compared to sucrose supplemented cultures. However, the specific N-glycan species which changed was similar between both conditions. Both sucrose and tagatose utilize the same mechanism for effecting the protein N-glycosylation profile since the pattern of change of the individual N-glycans was consistent between supplementation with both sugars.

Figure 15A:
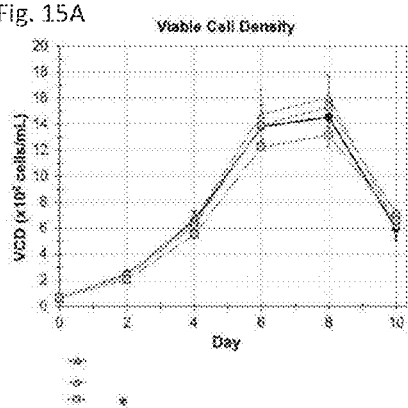
FIGS. 15A-15D depict the cell culture performance of Cell Line 2 in media supplemented with 1 mM, 30 mM, or 50 mM sucrose.
Figure 15B:
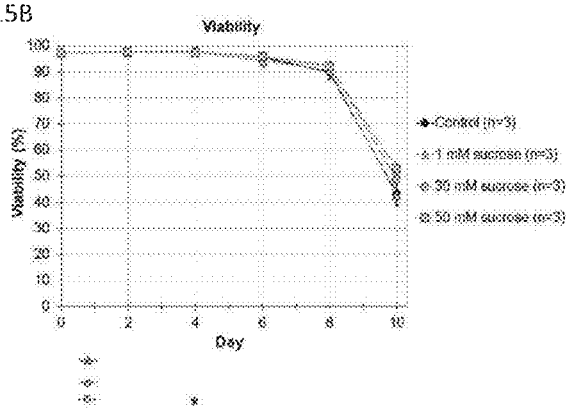
Figure 15C:
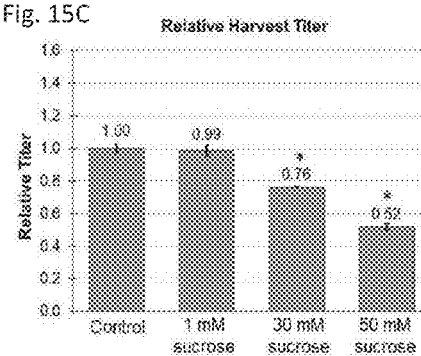

Impact of Sucrose and Tagatose on the Protein Glycosylation Profiles of Dual Variable Domain Immunoglobulins Cell Line 2 was cultured in shake flasks in fed batch mode after an abbreviated seed train. Sucrose and tagatose were supplemented into chemically-defined basal and feed media at concentrations of 1, 30, and 50 mM, and process performance results were compared to unsupplemented control conditions. The viable cell density (VCD), viability, and harvest titer results are shown in FIGS. 15A-15C for the sucrose supplemented cultures and FIGS. 16A-16C for the tagatose supplemented cultures.

Amongst the sucrose supplemented cultures, viable cell density remained approximately the same over time across the evaluated conditions. Only the 50 mM sucrose cultures demonstrated a reduction in peak VCD by at most $2 \times 10^6$ cells/mL. Cell viability results were similar across the various conditions up to process day 10. However, the relative harvest titer results were different among the conditions tested. As the sucrose concentration increased, the harvest titers decreased. The 50 mM sucrose cultures demonstrated the largest titer reduction of 48%, which was statistically significant from the control, and a much larger reduction than observed in Cell Line 1. Thus, it appears that sucrose is not as well tolerated in Cell Line 2 as compared to Cell Line 1.

Figure 15D:
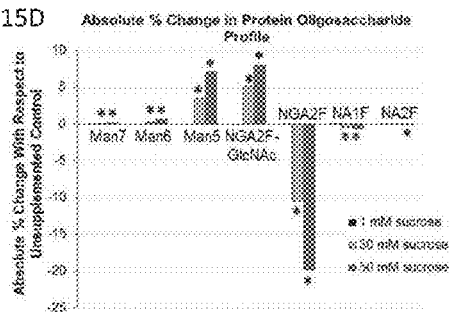
Figure 17A:
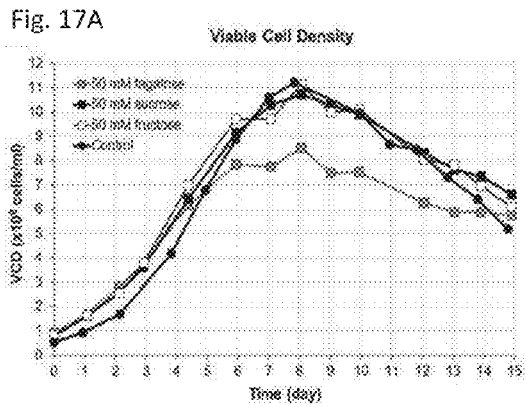
FIGS. 17A-17F depict the cell culture performance of Cell Line 1 in laboratory-scale bioreactors with media supplemented with 50 mM sucrose, tagatose, or fructose.
Figure 17B:
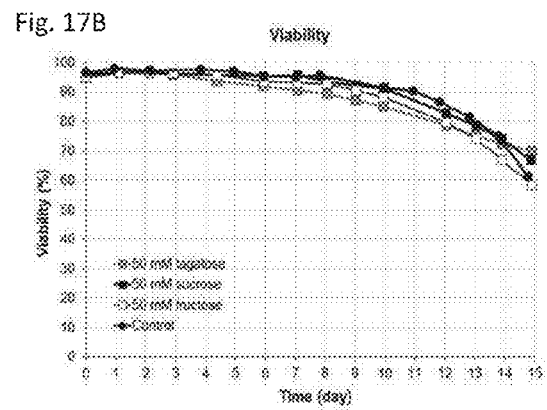
Figure 17C:
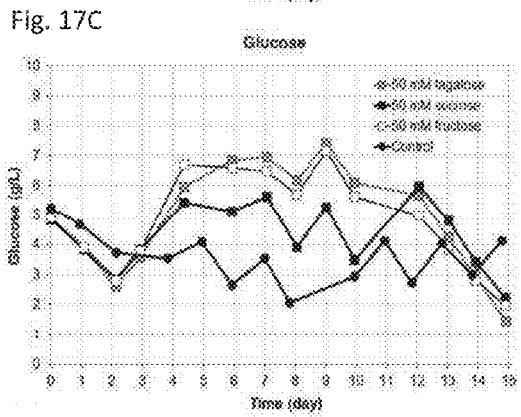
Figure 17D:
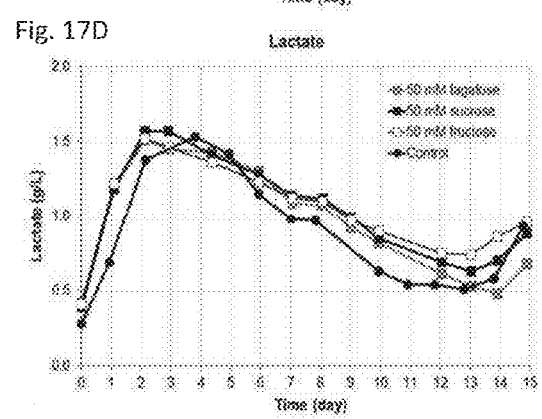
Figure 17E:
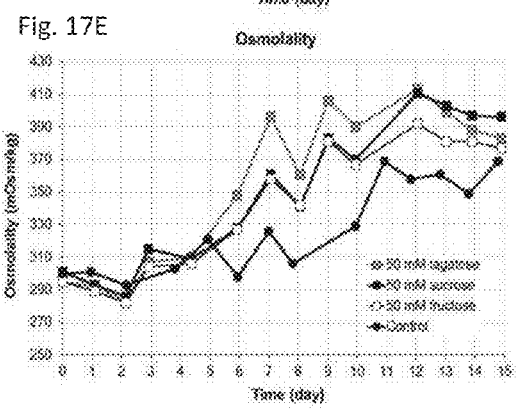
Figure 17F:
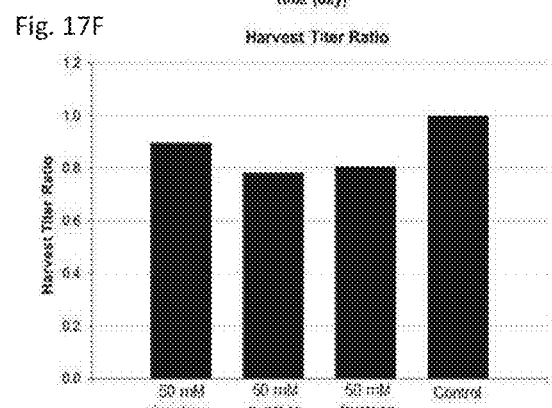

The impact of sucrose on the N-glycan oligosaccharide distribution is shown in FIG. 15D. There was a significant impact on the overall N-glycan distribution with sucrose supplementation. A concentration-dependent response was observed across all sucrose concentrations evaluated. Notably there was a 7% increase in Man 5 species and a 1% increase in Man 6 species with 50 mM sucrose supplementation of the culture. This cumulative increase of 8% in overall mannosylated N-glycans was accompanied by a 20% drop in NGA2F species, the majority of which was precluded from being formed due to the abrogation of the N-glycan biosynthetic reaction shown in FIG. 2. The data also demonstrate that the 20% decrease in NGA2F species, combined with a 1% decrease in NA1F species, and a 8% increase in NGA2F-GlcNAc species, resulted in an overall decrease in the fucosylation level of 13%. The 30 mM sucrose cultures demonstrated a similar decrease in overall fucosylation level, however the absolute percent change was lower.

Tagatose was also evaluated with Cell Line 2 to evaluate the effect on protein glycosylation. Similar to sucrose, none of the evaluated concentrations adversely impacted the viable cell density (VCD). At all concentrations evaluated, the VCD was actually slightly higher compared to the control. The cell viability results indicate that this parameter remained as high as the control through the majority of the process. After Day 8, the viability of the 30 mM and 50 mM tagatose supplemented cultures remained higher than the control, likely for the same reason as discussed above; the higher sugar concentration provided an enhanced level of nutrients that supported longer cell life. 1 mM tagatose did not adversely impact relative harvest titer, but both 30 mM and 50 mM tagatose significantly decreased harvest titer by 15% and 38%, respectively.

The impact of tagatose on the N-glycan oligosaccharide distribution of DVD 1 is shown in FIG. 16D. There was a significant impact on the overall N-glycan distribution. A concentration-dependent response was observed across all the tagatose concentrations evaluated. Notably there was a 3% increase in Man 5 species and a 1% increase in Man 6 species for the 50 mM sucrose supplementation condition. This cumulative increase of 4% in overall mannosylated N-glycans was accompanied by a 9% decrease in NGA2F species, the majority of which was precluded from being formed due to the abrogation of the N-glycan biosynthetic reaction shown in FIG. 2. The data also demonstrate that the 9% decrease in NGA2F species, combined with a 1% decrease in NA1F species, and a 5% increase in NGA2F-GlcNAc species, resulted in an overall decrease of the fucosylation level of 5%. The 30 mM tagatose cultures demonstrated a similar decrease in overall fucosylation, however the absolute percent change was lower.

Overall, sucrose and tagatose supplementation did not have as pronounced of an impact on the N-glycan profile of DVD 1 as did the supplementation on Antibody 1. The differences in the structure of these proteins contributed to the effect of sucrose or tagatose supplementation on the N-glycosylation profiles. These results demonstrate that while the absolute percentage of various N-glycan species may vary, overall, the effect of sucrose and/or tagatose supplementation on the N-glycan oligosaccharide profile is independent of the particular protein.

Impact of Sucrose and Tagatose on Protein Glycosylation Profiles is Independent of Culture Scale 3 L scale laboratory bioreactors were utilized to verify the impact of sucrose, tagatose, or fructose on protein glycosylation profiles. Concentrations of the sugars were chosen to minimize any potential adverse impacts on cell growth and productivity, but still facilitate a measurable impact on the glycoform profile. Cell culture process performance indicators were monitored and measured throughout the study. Viable cell density, cell viability, lactate, $pCO_2$, osmolality, harvest titer, and harvest N-glycan oligosaccharide data was measured and reported.

FIG. 17 shows the cell culture performance observed through the use of sucrose, tagatose, or fructose supplementation into the basal and feed medias. In laboratory-scale bioreactors there was no impact on viable cell density (VCD) or cell viability upon supplementation with 50 mM sucrose or 50 mM fructose compared to the unsupplemented control culture. Tagatose had a much more pronounced effect on viable cell density compared to the unsupplemented control. The results indicate a significant reduction in peak VCD of $11.2 \times 10^6$ cells/mL for the control versus $8.5 \times 10^6$ cells/mL for the tagatose supplemented culture. Despite this lower cell growth, cell viability remained high throughout the culture, on par with the results observed with the control. Residual media glucose and lactate production are direct measures of the metabolic activities of mammalian cells, respectively. The three sugars evaluated, all facilitated a higher relative level of residual glucose levels compared to the unsupplemented control where glucose was the only media sugar. With respect to lactate, there was no discernible difference between the various cultures. Osmolality of the sucrose, tagatose, or fructose supplemented cultures were only slightly higher compared to the control, primarily due to the additional sugar solute. Upon harvest, the final titer ratio was 0.90 for the tagatose supplemented culture, 0.78 for the sucrose supplemented culture, and 0.81 for the fructose supplemented culture.

Figure 18:
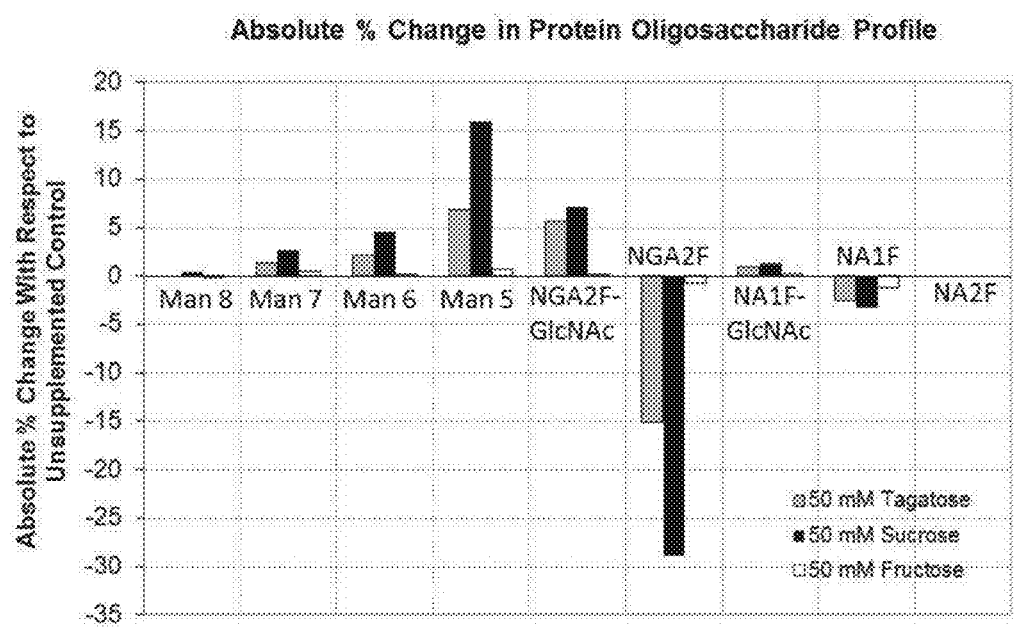
FIG. 18 depicts the absolute percent change in protein oligosaccharide profile of Cell Line 1 in laboratory-scale bioreactors with media supplemented with 50 mM sucrose, tagatose, or fructose.

After Protein A purification, the N-glycan oligosaccharide profile was measured with the results provided in FIG. 18. Similar to the shake flask results, there was a significant increase in overall mannosylation levels with sucrose supplementation. Man 7 increased 3%, Man 6 increased 5%, and Man 5 increased 16% for the sucrose supplemented culture. This 24% increase in overall mannosylation was accompanied by a 29% decrease in NGA2F species, 1% increase in NA1F-GlcNAc, 3% decrease in NA1F, 7% increase in NGA2F-GlcNAc, for an overall 24% decrease in fucosylation. The tagatose supplemented culture results were similar to those observed in the shake flasks. Man 7 increased 1%, Man 6 increased 2%, and Man 5 increased 7%. This 10% increase in overall mannosylation was accompanied by a 15% decrease in NGA2F species, 1% increase in NA1F-GlcNAc, 3% decrease in NA1F, and 6% increase in NGA2F-GlcNAc, for an overall 11% decrease in fucosylation. These changes in N-glycan oligosaccharide profile were consistent with the results obtained using the shake flasks.

The fructose supplemented culture did not facilitate any significant changes in protein glycosylation compared to the control. It is interesting that the results observed with sucrose supplementation, when glucose is already in the media, do not agree with the results observed with fructose supplementation into the cell culture media. Sucrose, which is comprised of glucose and fructose, modulates a protein glycosylation profile that does not correspond to the profile demonstrated when glucose and/or fructose are the predominant sugars in the cell culture. This indicates that the mechanism for sucrose modulation of the protein glycosylation profile (e.g., the increase in high mannose N-glycans and decrease in the fucosylation level) is not due to its constituent fructose or glucose alone. Instead, it is the complex of glucose to fructose (i.e., sucrose) that facilitates an enzymatic block at the high mannose to complex type N-glycan biosynthetic pathway (shaded areas in FIG. 2).

The cell culture process performance results in 3 L-scale bioreactors demonstrate that the effect of sucrose or tagatose supplementation on protein glycosylation is volumetric scale-independent. The significant increase in mannosylation, and resulting decrease in fucosylation, has important implications for the optimization of the production of protein therapeutics and the modulation of protein glycosylation profiles. Indeed, the selective use of sugars, such as sucrose and tagatose, increases the ability to customize the product characteristics of recombinant glycoproteins expressed in mammalian cells, and the resulting therapeutic activity, or comparability to a reference protein.

High Mannosylation/Low Fucosylation Effect on ADCC

Figure 20:
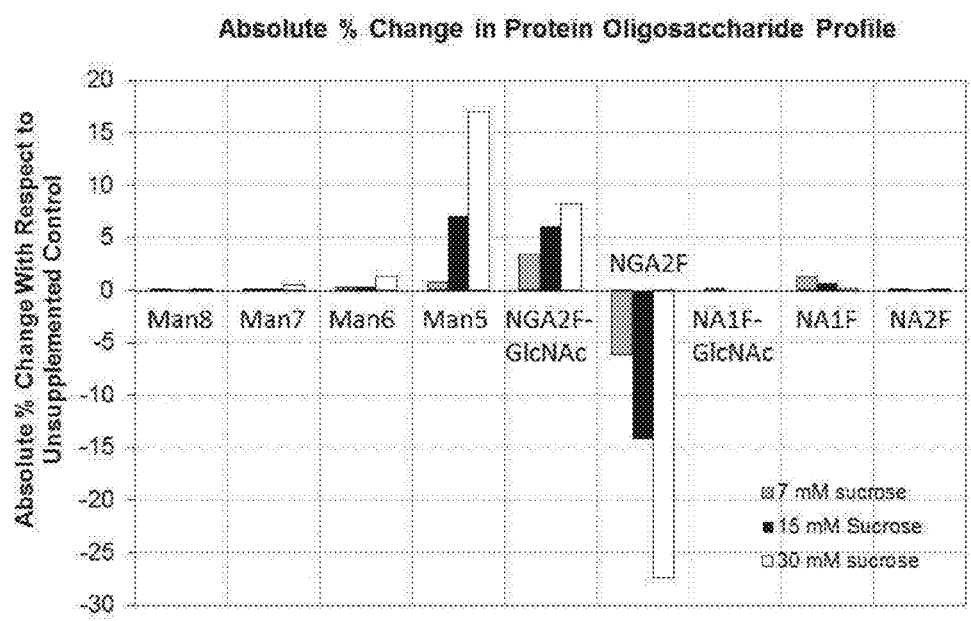
FIG. 20 depicts the absolute percent change in protein oligosaccharide profile of Cell Line 3 in shake flask cultures with media supplemented with 7 mM, 15 mM or 50 mM sucrose.
Figure 21:
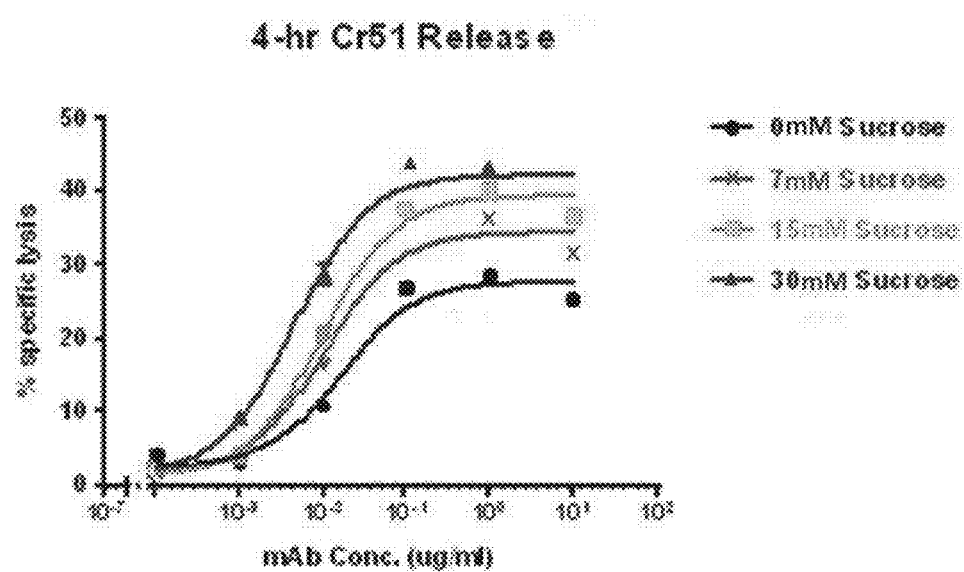
FIG. 21 depicts the Cr-51 release assay results for the measurement of antibody dependent cell cytotoxicity (ADCC) for antibodies purified from host cell cultures supplemented with 7 mM, 15 mM or 50 mM sucrose. The control was an unsupplemented culture.

Cell Line 3 was evaluated in shake flask culture in chemically defined media supplemented with 7, 15, and 30 mM sucrose. The cultures were harvested, and the N-glycan oligosaccharide profiles were measured with the results shown in FIG. 20. There was a significant increase in overall mannosylation levels, and thus a significant decrease in overall fucosylation levels. The response to sucrose was dependent on the sucrose concentration and similar to the response demonstrated in Cell Lines 1 and 2. Notably there was a 17% increase in Man 5 species, 1% increase in Man 6 species, and a 1% increase in Man 7 species for the 30 mM sucrose supplementation condition. This cumulative increase of 19% in overall mannosylated N-glycans was accompanied by a 27% drop in NGA2F species, the majority of which was precluded from being formed due to the abrogation of the N-glycan biosynthetic reaction shown in FIG. 2. The data also demonstrates that with the combined 27% decrease in NGA2F species and 8% increase in NGA2F-GlcNAc species, that the overall fucosylation level was decreased by 19%. Antibody 3, purified from the sucrose supplemented cell cultures, was tested in a Cr-51 release assay to evaluate effector function, specifically ADCC activity. This was performed to verify that the lower level of fucosylated N-glycans linked to Antibody 3 would facilitate an increase in ADCC activity. The results are shown in FIG. 21. Antibodies purified from the 30 mM sucrose supplemented culture had the highest levels of high mannose N-glycans, and lowest levels of fucosylated N-glycans. These antibodies also demonstrated the largest percent lysis of target cells, an increase of about 15% compared to the cell lysis demonstrated with the unsupplemented control. Purified antibodies from the cultures supplemented with lower sucrose concentrations of 7 mM and 15 mM also facilitated an increase in percent lysis of target cells relative to the control, though the increase was lower when compared to the increase in percent lysis produced by antibodies purified from the cultures supplemented with 30 mM sucrose. These results indicate that not only can sucrose supplementation modulate the glycosylation profile of proteins, e.g., antibodies, but the modulation has a beneficial impact on ensuring biologic comparability as well as therapeutic efficacy.

DISCUSSION

Sucrose and tagatose are two sugars found in nature. Sucrose, in particular, has been found to be the most abundant sugar in soy beans (Hou A., et al., Internat. J Agronomy (2009) Article ID 484571:8).

The data provided above demonstrate that the selective supplementation of sucrose and tagatose in host cell culture media is an effective approach for the targeted modulation of protein glycosylation profiles in cultured cell lines. In particular, supplementation of host cell culture media effectively modulated the N-glycan glycoform profile towards high mannose species, and decreased the overall level of fucosylated species. Since both sugars resulted in similar glycosylation profiles, it is likely that they modulate glycosylation via the same mechanism or pathway. Of the high mannose N-glycan species, Man 5 glycan increased the most upon exposure to either of the two sugars. Amongst the non-mannosylated N-glycan species, the largest increase was demonstrated in NGA2F-GlcNAc levels. The fact that both of Man 5 glycan and NGA2F-GlcNAc share the same UDP-GlcNAc co-substrate (FIG. 2, highlighted) suggests that their accumulation may be due to inhibition of these reactions through a diminished supply of available UDP-GlcNAc substrate. The same shifting in protein glycosylation profiles was observed across multiple sucrose and tagatose concentrations in a concentration-dependent manner and across multiple cell lines expressing recombinant proteins. At select concentrations, an adverse impact of these sugars on cell growth and productivity was minimized. The use of sucrose and/or tagatose in cell culture media provides an efficient and effective approach toward re-targeting of specific N-glycan glycoform profiles. This capability is important for ensuring biologic comparability, as well as the targeted optimization of product quality. The targeted increase in mannosylation levels, and decrease in fucosylation levels, is an important capability since for some recombinant glycoprotein therapeutics, high mannose glycans are a desired product characteristic. Furthermore, the decrease in overall fucosylation levels has been correlated with an increased ADCC response. High mannose glycans are also reported to be cleared faster from circulation (Alessandri, L., et al., (2012) mAbs Journal 4(4): 1-1210). The ability to modulate protein glycosylation through the selective use of monosaccharides and oligosaccharides (e.g., sucrose and tagatose) is critically important for achieving critical product characteristics.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols that may be cited throughout this application, the disclosures of which are incorporated herein by reference in their entireties for all purposes. The contents of all cited references, including literature references, issued patents, and published patent applications, as cited throughout this application are hereby expressly incorporated herein by reference. It should further be understood that the contents of all the figures and tables attached hereto are expressly incorporated herein by reference. The entire contents of the following applications are also expressly incorporated herein by reference: U.S. Provisional Patent Application 61/893,123, entitled "STABLE SOLID PROTEIN COMPOSITIONS AND METHODS OF MAKING SAME", filed on Oct. 18, 2013; U.S. Provisional Application Ser. No. 61/892,833, entitled "LOW ACIDIC SPECIES COMPOSITIONS AND METHODS FOR PRODUCING THE SAME USING DISPLACEMENT CHROMATOGRAPHY", filed on Oct. 18, 2013; U.S. Provisional Patent Application 61/892,710, entitled "MUTATED ANTI-TNFα ANTIBODIES AND METHODS OF THEIR USE", filed on Oct. 18, 2013; U.S. Provisional Patent Application 61/893,088, entitled "MODULATED LYSINE VARIANT SPECIES AND METHODS FOR PRODUCING AND USING THE SAME", filed on Oct. 18, 2013; U.S. Provisional Patent Application 61/893,131, entitled "PURIFICATION OF PROTEINS USING HYDROPHOBIC INTERACTION CHROMATOGRAPHY", filed on Oct. 18, 2013; and U.S. patent application Ser. No. 14/077,871, entitled "LOW ACIDIC SPECIES COMPOSITIONS AND METHODS FOR PRODUCING AND USING THE SAME", filed on Nov. 12, 2013.

We claim:

1. A method of producing a composition comprising an immunoglobulin with an increased level of mannosylated N-glycans and/or a decreased level of fucosylated N-glycans, wherein the immunoglobulin comprises a light chain variable region of SEQ ID NO:1 and a heavy chain variable region of SEQ ID NO:2, said method comprising: culturing a mammalian host cell expressing said immunoglobulin in cell culture media supplemented with 5 mM-100 mM sucrose, thereby producing said composition comprising said immunoglobulin with an increased level of mannosylated N-glycans and/or a decreased level of fucosylated N-glycans as compared to a control, wherein said control is a composition comprising the immunoglobulin produced by culturing the mammalian host cell expressing said immunoglobulin in cell culture media which is not supplemented with sucrose.

2. The method of claim 1, further comprising purifying said composition comprising said immunoglobulin with a modulated glycosylation profile.

3. The method of claim 1, wherein the immunoglobulin is an antibody or antigen-binding portion thereof.

4. The method of claim 1, wherein the immunoglobulin is adalimumab, or an antigen binding fragment thereof.

5. The method of claim 1, wherein the immunoglobulin is a dual variable domain immunoglobulin (DVD-Ig).

6. The method of claim 1, wherein the immunoglobulin is selected from the group consisting of a TVD-IG, a half-body and a RAB.

7. The method of claim 1, further comprising supplementing the cell culture media with tagatose.

8. The method of claim 7, wherein the cell culture media is supplemented with a sufficient amount of tagatose to achieve a tagatose concentration selected from the group consisting of about 1 mM, about 5 mM, about 7 mM, about 10 mM, about 20 mM, about 30 mM, about 40 mM, about 50 mM, about 60 mM, about 70 mM, about 80 mM, about 90 mM and about 100 mM.

9. The method of claim 8, wherein the tagatose concentration is 30 mM.

10. The method of claim 1 wherein the cell culture media is supplemented with a sufficient amount of sucrose to achieve a sucrose concentration selected from the group consisting of about 5 mM, about 7 mM, about 10 mM, about 20 mM, about 30 mM, about 40 mM, about 50 mM, about 60 mM, about 70 mM, about 80 mM, about 90 mM and about 100 mM.

11. The method of claim 10, wherein the sucrose concentration is 30 mM.

12. The method of claim 1, wherein the method produces a composition comprising an immunoglobulin with an overall increase in the mannosylated N-glycan level.

13. The method of claim 12, wherein the increase in the mannosylation level comprises an increase in the level of a high mannose N-glycan oligosaccharide selected from the group consisting of Man 5 glycan, Man 6 glycan, Man 7 glycan and Man 8 glycan.

14. The method of claim 1, wherein the method produces a composition comprising an immunoglobulin with an overall decrease in the fucosylated N-glycan level.

15. The method of claim 14, wherein the overall decrease in the fucosylation level comprises an increase in NGA2F-GlcNAc and NA1F-GlcNAc and a decrease in the level of NGA2F, and NA1F in said immunoglobulin.

16. The method of claim 1, wherein the decrease in the fucosylation level comprises a decrease in the level of NGA2F, and/or NA1F in said immunoglobulin.

17. The method of claim 1, wherein said host cell is a CHO cell.

18. A method of producing a composition comprising adalimumab with a modulated glycosylation profile, said method comprising: culturing a mammalian host cell expressing adalimumab in cell culture media supplemented with 5 mM-100 mM sucrose, thereby producing said composition comprising adalimumab with an increased level of mannosylated N-glycans and/or a decreased level of fucosylated N-glycans as compared to a control, wherein said control is a composition comprising adalimumab produced by culturing the mammalian host cell expressing adalimumab in cell culture media which is not supplemented with sucrose.

19. A method of producing a composition comprising an antibody, or antigen binding fragment thereof, with a modulated glycosylation profile, wherein the antibody or antigen-binding portion thereof comprises a light chain variable region of SEQ ID NO:1 and a heavy chain variable region of SEQ ID NO:2, said method comprising: culturing a mammalian host cell expressing said antibody, or antigen binding fragment thereof, in cell culture media supplemented with 5 mM-100 mM sucrose, thereby producing said composition comprising said antibody, or antigen binding fragment thereof, with an overall increase in the level of mannosylated N-glycans and an overall decrease in the level of fucosylated N-glycans as compared to a control, wherein said control is a composition comprising the antibody, or antigen binding fragment thereof, produced by culturing the mammalian host cell expressing said antibody, or antigen binding fragment thereof, in cell culture media which is not supplemented with sucrose.

20. The method of claim 19, wherein the antibody is adalimumab, or antigen binding fragment thereof.

21. A method of producing a composition comprising an antibody, or antigen binding fragment thereof, with a modulated glycosylation profile, wherein the antibody or antigen-binding portion thereof comprises a light chain variable region of SEQ ID NO:1 and a heavy chain variable region of SEQ ID NO:2, said method comprising: culturing a mammalian host cell expressing said antibody, or antigen binding fragment thereof, in cell culture media supplemented with 5 mM-100 mM sucrose, thereby producing said composition comprising said antibody, or antigen binding fragment thereof, with an increase in antibody-dependent cellular cytotoxicity (ADCC) response as compared to a control, wherein said control is a composition comprising the antibody, or antigen binding fragment thereof, produced by culturing the mammalian host cell expressing said antibody, or antigen binding fragment thereof, in cell culture media which is not supplemented with sucrose.

22. The method of claim 21, wherein the antibody is adalimumab, or antigen binding fragment thereof.

* * * * *

```
SEQUENCE LISTING

<160> NUMBER OF SEQ ID NOS: 12

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
```

```
                    50                  55                  60
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
 1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
```

```
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
 1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tgagggccg attcaccatc tccagagaca cgccaagaa ctccctgtat    240 ctgcaaatga acagtctgag agctgaggat acggccgtat attactgtgc aaagtctcg    300 taccttagca ccgcgtcctc ccttgactat tggggccaag gtaccctggt caccgtctcg    360
agt                                                                  363

<210> SEQ ID NO 11
<211> LENGTH: 214
<212> TYPE: PRT
<213> ORGANISM: Artificial Sequence
<220> FEATURE:
<223> OTHER INFORMATION: adalimumab light chain

<400> SEQUENCE: 11
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
             165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
             195                 200                 205

Phe Asn Arg Gly Glu Cys
    210

<210> SEQ ID NO 12
<211> LENGTH: 451
<212> TYPE: PRT
<213> ORGANISM: Artificial Sequence
<220> FEATURE:
<223> OTHER INFORMATION: adalimumab heavy chain

<400> SEQUENCE: 12

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
             35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
             100                 105                 110

Gln Gly Thr Leu Val Thr Val Ser Ser Ala Ser Thr Lys Gly Pro Ser
             115                 120                 125

Val Phe Pro Leu Ala Pro Ser Ser Lys Ser Thr Ser Gly Gly Thr Ala
130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```